(12) United States Patent
Pendergast

(10) Patent No.: US 9,931,342 B2
(45) Date of Patent: Apr. 3, 2018

(54) COMPOSITIONS AND METHODS FOR THE TREATMENT OF CANCER

(71) Applicant: Duke University, Durham, NC (US)

(72) Inventor: Ann Marie Pendergast, Durham, NC (US)

(*) Notice: Subject to any disclaimer, the term of this patent is extended or adjusted under 35 U.S.C. 154(b) by 0 days.

(21) Appl. No.: 15/422,725

(22) Filed: Feb. 2, 2017

(65) Prior Publication Data

US 2017/0216289 A1 Aug. 3, 2017

Related U.S. Application Data

(60) Provisional application No. 62/289,979, filed on Feb. 2, 2016.

(51) Int. Cl.
| | |
|---|---|
| *C07D 239/42* | (2006.01) |
| *A61K 31/44* | (2006.01) |
| *A61B 10/00* | (2006.01) |
| *A61K 31/506* | (2006.01) |
| *A61K 31/505* | (2006.01) |
| *A61K 31/4439* | (2006.01) |
| *C12Q 1/68* | (2018.01) |

(52) U.S. Cl.
CPC ........ *A61K 31/506* (2013.01); *A61K 31/4439* (2013.01); *A61K 31/505* (2013.01); *C12Q 1/6886* (2013.01); *C12Q 2600/118* (2013.01); *C12Q 2600/158* (2013.01)

(58) Field of Classification Search
CPC ...... C07D 401/12; C07D 401/04; A61B 10/02
USPC ................................. 514/256, 341; 600/562
See application file for complete search history.

(56) References Cited

U.S. PATENT DOCUMENTS

2013/0310395 A1 11/2013 Dodd et al.

OTHER PUBLICATIONS

Advani et al., "A.M. Bcr-Abl variants: biological and clinical aspects," *Leukemia Research*, 2002; 26:713-720.
Ara et al., "Y.A. Interleukin-6 in bone metastasis and cancer progression," *Eur. J. Cancer*, 2010, 46, 1223-1231.
Ashkenazi et al., "Targeting death and decoy receptors of the tumour-necrosis factor superfamily," *Nat. Rev. Cancer*, 2002, 2, 420-430.
Axmann et al., "Inhibition of interleukin-6 receptor directly blocks osteoclast formation in vitro and in vivo," *Arthritis Rheum.*, 2009, 60, 2747-2756.
Azzolin et al. "Role of TAZ as mediator of Wnt signaling," *Cell*, 2012, 151, 1443-1456.
Behbahani et al., "Tyrosine kinase expression profile in clear cell renal cell carcinoma," *World J. Urol.*, 2012; 30:559-565.
Bi et al., "Sphingosine-1-phosphate mediates a reciprocal signaling pathway between stellate cells and cancer cells that promotes pancreatic cancer growth," *Am. J. Path.*, 2014; 184:2791-2802.
Bicciato et al. "Genome-wide association between YAP/TAZ/TEAD and Ap-1 at enhancers drives oncogenic growth," *Nat. Cell Biol.* 17, 1218-1227 (2015).
Blanchard et al., "Geminin overexpression promotes imatinib sensitive breast cancer: A novel treatment approach for aggressive breast cancers, including a subset of triple negative," *PLOS One.* 9, e95663 (2014).
Bos et al., "Genes that mediate breast cancer metastasis to the brain," *Nature*, 2009, 459, 1005-1009.
Bradley et al., "Regulation of cell migration and morphogenesis by Abl-family kinases: Emerging mechanisms and physiological contexts," *J. Cell Sci.*, 2009, 122, 3441-3454.
Britschgi et al., "JAK2/STAT5 inhibition circumvents resistance to PI3K/ mTOR blockade: A rationale for co-targeting these pathways in metastatic breast cancer," *Cancer Cell*, 2012, 22, 796-811.
Cerami et al., "The cBio cancer genomics portal: an open platform for exploring multidimensional cancer genomics data," *Cancer Discov.*, 2012; 2:401-404.
Chevalier et al., "ABL Tyrosine Kinase Inhibition Variable Effects on the Invasive Properties of Different Triple Negative Breast Cancer Cell Lines," *PLoS One*, 2015, 10(3): e0118854.
Chislock et al., "Abl family kinases regulate endothelial barrier function in vitro and in mice," *PLOS One*, 2013, 8(12): e85231.
Chislock et al., "Abl kinases are required for vascular function, Tie2 expression, and angiopoietin-1-mediated survival," *Proc. Natl. Acad. Sci. USA*, 2013,110, 12432-12437.
Choi et al., "N. S. N-myristoylated c-Abl tyrosine kinase localizes to the endo-plasmic reticulum upon binding to an allosteric inhibitor," *J. Biol. Chem.*, 2009, 284, 29005-29014.
Cicek et al., "M., Oursler, M.J. Breast cancer bone metastasis and current small therapeutics," Cancer Metastasis Rev., 25, 2006, 635-644.
Cleary et al., "Role of Abl in airway hyper-responsiveness and airway remodeling," Respiratory Research, 2013; 14:105.
Colicelli et al., "ABL tyrosine kinases: Evolution of function, regulation, and specificity," *Sci. Signal.*, 2010, 3re6.
Cordenonsi et al., "The Hippo transducer TAZ confers cancer stem cell-related traits on breast cancer cells," *Cell*, 147, 759-772 (2011).
Cortina et al., "EphB-ephrin-B interactions suppress colorectal cancer progression by compartmentalizing tumor cells," *Nature Genetics*, 2007; 39:1376-1383.
Cristofanilli et al., "Imatinib mesylate (Gleevec) in advanced breast cancer-expressing C-Kit or PDGFR-p: Clinical activity and biological correlations," *Ann. Oncol*, 2008, 19, 1713-1719.
Crnogorac-Jurcevic et al., "Expression profiling of microdissected pancreatic adenocarcinomas," *Oncogene*, 2002; 21:4587-4594.
De Braekeleer et al., "ABL1 fusion genes in hematological malignancies: a review," *Eur. J. Haem.*, 2011; 86:361-371.
de Groot et al., "L. STAT5 activation by BCR-Abl contributes to transformation of K562 leukemia cells," *Blood*, 1999, 94, 1108-1112.
De Keersmaecker et al., "Kinase activation and transformation by NUP214-ABL1 is dependent on the context of the nuclear pore," *Molecular cell.*, 2008; 31:134-142.

(Continued)

*Primary Examiner* — Raymond J Henley, III
(74) *Attorney, Agent, or Firm* — Womble Bond Dickinson (US), LLP; Scott R. Breining

(57) ABSTRACT

The present disclosure provides compositions and methods for the treatment of cancer, relating to the specific inhibition of Abelson (ABL) kinases.

52 Claims, 21 Drawing Sheets

(56) References Cited

OTHER PUBLICATIONS

Duncan et al., "Dynamic reprogramming of the kinome in response to targeted MEK inhibition in triple-negative breast cancer," Cell, 2012, 149:307-321.
Eide et al., "T. Chronic Myeloid Leukemia: Advances in Understanding Disease Biology and Mechanisms of Resistance to Tyrosine Kinase Inhibitors," Curr. Hem. Malignancy Reports, Jun. 2015;10(2):158-66.
Ell et al., "SnapShot: Bone metastasis," Cell, 2012, 151, 690.
Ferbeyre et al., "R. The role of Stat5 transcription factors as tumor suppressors or oncogenes," Biochim. Biophys. Acta, 2011, 1815, 104-114.
Fidler et al., "The pathogenesis of cancer metastasis: the 'seed and soil' hypothesis revisited," Nat. Rev. Cancer, 2003; 3:453-458.
Fiore et al., "c-Abl and Arg induce cathepsin-mediated lysosomal degradation of the NM23-H1 metastasis suppressor in invasive cancer," Oncogene, 2014; 33:4508-4520.
Furlan et al., "Abl interconnects oncogenic Met and p53 core pathways in cancer cells," Cell Death Diff., 2011; 18:1608-1616.
Ganguly et al., "c-Abl and Arg are activated in human primary melanomas, promote melanoma cell invasion via distinct pathways, and drive metastatic progression," Oncogene, 2012; 31:1804-1816.
Ganguly et al., "Activation of Abl family kinases in solid tumors," Genes Cancer, 2012, 3, 414-425.
Genander et al., "Dissociation of EphB2 signaling pathways mediating progenitor cell proliferation and tumor suppression," Cell, 2009; 139:679-692.
Gil-Henn et al., "Arg/Abl2 promotes invasion and attenuates proliferation of breast cancer in vivo," Oncogene, 2012, 32, 2622-2630.
Gjerdrum et al., "Axl is an essential epithelial-to-mesenchymal transition-induced regulator of breast cancer metastasis and patient survival," Proc. Natl. Acad. Sci. USA. 2010, 107, 1124-1129.
Gonfloni et al., "DNA damage stress response in germ cells: role of c-Abl and clinical implications," Oncogene. 2010; 29:6193-6202.
Gonfloni et al., "Inhibition of the c-Abl-TAp63 pathway protects mouse oocytes from chemotherapy-induced death. Nature Medicine," 2009; 15:1179-1185.
Gourley et al., "Loss of dendrite stabilization by the Abl-related gene (Arg) kinase regulates behavioral flexibility and sensitivity to cocaine," Proc. Natl. Acad. Sci. USA. 2009; 106:16859-16864.
Greuber et al., "Abl Family Kinases Regulate FcγR-Mediated Phagocytosis in Murine Macrophages," J. Immunol. 2012; 189:5382-5392.
Greuber et al., "Role of ABL family kinases in cancer: From leukaemia to solid tumours," Nat. Rev. Cancer 13, 559-571 (2013).
Gu et al., "Abl family kinases modulate T cell-mediated inflammation and chemokine-induced migration through the adaptor HEF1 and the GTPase Rap1,"Sci Signal. 2012; 5:ra51.
Gu et al., "Defective T cell development and function in the absence of Abelson kinases," J. Immunol. 2007; 179:7334-7343.
Gu et al., "Inactivation of ABL kinases suppresses non-small cell lung cancer metastasis,"JCI Insight 1(21): e89647. (PMCID: PMC5161211) (2016).
Gu et al., "Stat5 promotes metastatic behavior of human prostate cancer cells in vitro and in vivo," Endocr. Relat. Cancer 17, 481-493 (2010).
Hantschel et al., "Regulation of the c-Abl and Bcr-Abl tyrosine kinases," Nat. Rev. Mol. Cell Biol. 2004; 5:33-44.
Hong et al., "AXL mediates TRAIL resistance in esophageal adenocarcinoma. Neoplasia 15," 296-304 (2013).
Iavarone et al., "Activation of the Erk8 mitogen-activated protein (MAP) kinase by RET/PTC3, a constitutively active form of the RET proto-oncogene," J. Biol. Chem. 2006; 281:10567-10576.
Jones et al., "A quantitative protein interaction network for the ErbB receptors using protein microarrays," Nature. 2006; 439:168-174.
Kang et al., "A multigenic program mediating breast cancer metastasis to bone," Cell 3, 537-549 (2003).
Kawai et al., "Functional analysis of the SEPT9-ABL1 chimeric fusion gene derived from T-prolymphocytic leukemia," Leukemia Res. 2014; 38:1451-1459.

Koleske et al., "Essential roles for the Abl and Arg tyrosine kinases in neurulation," Neuron. 1998; 21:1259-1272.
Korkaya et al., "Activation of an IL6 inflammatory loop mediates trastuzumab resistance in HER2+ breast cancer by expanding the cancer stem cell population," Mol. Cell 47, 570-584 (2012).
Kua et al., "c-Abl promotes osteoblast expansion by differentially regulating canonical and non-canonical BMP pathways and p16INK4a expression," Nat. Cell Biol. 2012; 14:727-737.
Kundu et al., "An EphB-Abl signaling pathway is associated with intestinal tumor initiation and growth," Science Trans. Med. 2015; 7:281ra244.
Levy et al., "Yap1 phosphorylation by c-Abl is a critical step in selective activation of proapoptotic genes in response to DNA damage," Mol. Cell 29, 350-361 (2008).
Li et al., "Mice deficient in Abl are osteoporotic and have defects in osteoblast maturation," Nature Genetics. 2000; 24:304-308.
Li et al., "Abl Kinases Regulate HGF/Met Signaling Required for Epithelial Cell Scattering, Tubulogenesis and Motility," PLoS One. 2015; 10:e0124960.
Lin et al., "Activated c-Abl tyrosine kinase in malignant solid tumors," Oncogene. 2008; 27:4385-4391.
Lo et al., "Inhibition of c-Abl sensitizes breast cancer cells to the dual ErbB receptor tyrosine kinase inhibitor lapatinib (GW572016)," Anticancer Research. 2011; 31:789-795.
Lu et al., "ADAMTS1 and MMP1 proteolytically engage EGF-like ligands in an osteolytic signaling cascade for bone metastasis," Genes Dev. 23,1882-1894 (2009).
Nevalainen et al., "Stat5 promotes metastatic behavior of human prostate cancer cells in vitro and in vivo," Endocr. Relat. Cancer. 17, 481-493 (2010).
Mader et al., "An EGFR-Src-Arg-cortactin pathway mediates functional maturation of invadopodia and breast cancer cell invasion," Cancer Res. 2011; 71:1730-1741.
Matei et al., "Imatinib mesylate (Gleevec) inhibits ovarian cancer cell growth through a mechanism dependent on platelet-derived growth factor receptor alpha and Akt inactivation," Clin Cancer Res. 2004; 10:681-690.
Mitsiades et al., "Ewing's sarcoma family tumors are sensitive to tumor necrosis factor-related apoptosis-inducing ligand and express death receptor 4 and death receptor 5," Cancer Res. 61, 2704-2712 (2001).
Modi et al., "A phase II trial of imatinib mesylate monotherapy in patients with metastatic breast cancer," Breast Cancer Res. Treat. 90, 157-163 (2005).
Moresco et al., "Integrin-mediated dendrite branch maintenance requires Abelson (Abl) family kinases," J. Neuroscience. 2005; 25:6105-6118.
Nagar et al., "Crystal structures of the kinase domain of c-Abl in complex with the small molecule inhibitors PD173955 and imatinib (STI-571)," Cancer Res. 2002; 62:4236-4243.
Nelson et al., "Cholesterol and breast cancer pathophysiology," Trends Endocrinol. Metab. 25, 649-655 (2014).
O'Hare et al., "Pushing the limits of targeted therapy in chronic myeloid leukemia," Nat. Rev. Cancer. 2012; 12:513-526.
Oskarsson et al. "Breast cancer cells produce tenascin C as a metastatic niche component to colonize the lungs," Nat. Med. 17, 867-874 (2011).
Packer et al., "Nilotinib and MEK inhibitors induce synthetic lethality through paradoxical activation of RAF in drug-resistant chronic myeloid leukemia," Cell. 20, 715-727 (2011).
Panjarian et al., "Structure and dynamic regulation of Abl kinases," J. Biol. Chem. 2013; 288:5443-5450.
Pemovska et al., "Axitinib effectively inhibits BCR-ABL1(T315I) with a distinct binding conformation," Nature. 2015; 519:102-105.
Pendergast, "The Abl family kinases: Mechanisms of regulation and signaling," Adv. Cancer Res. 85, 51-100 (2002).
Pietras et al., "Functions of paracrine PDGF signaling in the proangiogenic tumor stroma revealed by pharmacological targeting," PLoS Medicine. 2008; 5:e19.
Plattner et al., "A new link between the c-Abl tyrosine kinase and phosphoinositide signaling through PLC-gammal," Nat. Cell Biol. 2003; 5:309-319.

(56) References Cited

OTHER PUBLICATIONS

Puls et al., "Current status of SRC inhibitors in solid tumor malignancies," The Oncologist. 2011; 16:566-578.
Qiu et al., "c-Abl tyrosine kinase regulates cardiac growth and development," Proc. Natl. Acad. Sci. USA. 2010; 107:1136-1141.
Raimondi et al., "Imatinib inhibits VEGF-independent angiogenesis by targeting neuropilin 1-dependent ABL1 activation in endothelial cells," J. Exp. Med. 2014; 211:1167-1183.
Ren "Mechanisms of BCR-ABL in the pathogenesis of chronic myelogenous leukemia," Nat Rev. Cancer. 2005; 5:172-183.
Ren et al., "Loss of Stat5a delays mammary cancer progression in a mouse model," Oncogene. 21, 4335-4339 (2002).
Rhodes et al., "Oncomine 3.0: Genes, pathways, and networks in a collection of 18,000 cancer gene expression profiles," Neoplasia. 9, 166-180 (2007).
Roberts et al., "Targetable kinase-activating lesions in Ph-like acute lymphoblastic leukemia," N. Engl. J. Med. 2014; 371:1005-1015.
Roodman, "Mechanisms of bone metastasis," N. Engl. J. Med. 350, 1655-1664 (2004).
Salgado et al., "Circulating interleukin-6 predicts survival in patients with metastatic breast cancer," Int. J. Cancer 103, 642-646 (2003).
Schwartzberg et al., "Mice homozygous for the ablml mutation show poor viability and depletion of selected B and T cell populations," Cell 1991; 65:1165-1175.
Sethi et al., "Tumor-derived Jagged1 promotes osteolytic bone metastasis of breast cancer by engaging notch signaling in bone cells," Cell 19, 192-205 (2011).
Simonet et al., "Osteoprotegerin: A novel secreted protein involved in the regulation of bone density," Cell. 89, 309-319 (1997).
Simpson et al., "Renal medullary carcinoma and ABL gene amplification," J. Urol. 2005; 173:1883-1888.
Sims et al., "Imatinib reverses doxorubicin resistance by affecting activation of STAT3-dependent NF-kappaB and HSP27/p38/AKT pathways and by inhibiting ABCB1," PLoS One. 2013; 8:e55509.
Sims et al., "STI571 sensitizes breast cancer cells to 5-fluorouracil, cisplatin and camptothecin in a cell type-specific manner," Biochem. Pharm. 2009; 78:249-260.
Sirvent et al. "The tyrosine kinase Abl is required for Src-transforming activity in mouse fibroblasts and human breast cancer cells," Oncogene. 26, 7313-7323 (2007).
Sirvent et al., "Cytoplasmic signalling by the c-Abl tyrosine kinase in normal and cancer cells," Biology of the Cell. 2008; 100:617-631.
Smith-Pearson et al., "Abl kinases are required for invadopodia formation and chemokine-induced invasion," J. Biol. Chem. 285, 40201-40211 (2010).
Sonoshita et al., "Promotion of colorectal cancer invasion and metastasis through activation of NOTCH-DAB1-ABL-RHOGEF protein TRIO," Cancer Discov. 2015; 5:198-211.
Sos et al., "Predicting drug susceptibility of non-small cell lung cancers based on genetic lesions," J. Clin. Invest. 2009; 119:1727-1740.
Sourbier et al., "Targeting ABL1-Mediated Oxidative Stress Adaptation in Fumarate Hydratase-Deficient Cancer," Cell. 2014; 26:840-850.
Srinivasan et al., "Activation of Abl tyrosine kinases promotes invasion of aggressive breast cancer cells," Cancer Res. 2006; 66:5648-5655.
Srinivasan et al., "Aggressive breast cancer cells are dependent on activated Abl kinases for proliferation, anchorage-independent growth and survival," Oncogene. 27, 1095-1105 (2008).
Stahtea et al., "Imatinib inhibits colorectal cancer cell growth and suppresses stromal-induced growth stimulation, MT1-MMP expression and pro-MMP2 activation,"Int. J. Cancer. 2007; 121:2808-2814.
Stuhlmiller et al., "Inhibition of Lapatinib-Induced Kinome Reprogramming in ERBB2-Positive Breast Cancer by Targeting BET Family Bromodomains," Cell Reports. 2015; 11:390-404.

Subramanian et al., "Gene set en-richment analysis: A knowledge-based approach for interpreting genome-wide ex-pression profiles," Proc. Natl. Acad. Sci. USA. 102, 15545-15550 (2005).
Sun et al., "Abl interactor 1 regulates Src-Idl-matrix metalloproteinase 9 axis and is required for invadopodia formation, extracellular matrix degradation and tumor growth of human breast cancer cells," Carcinogenesis. 2009; 30:2109-2116.
Sun et al., "Activation of the cytoplasmic c-Abl tyrosine kinase by reactive oxygen species," J. Biol. Chem. 2000; 275:17237-17240.
Tamura et al., Soluble interleukin-6 receptor triggers osteoclast formation by interleukin 6. Proc. Natl. Acad. Sci. USA. 90, 11924-11928 (1993).
Tawakkol et al., "Activation of an IL6 inflammatory loop mediates trastuzumab resistance in HER2+ breast cancer by expanding the cancer stem cell population," Mol. Cell 47, 570-584 (2012).
"The Cancer Genome Atlas Network. Comprehensive molecular portraits of human breast tumours," Nature, 2012; 490:61-70.
Trampont et al., "ShcA Regulates Thymocyte Proliferation through Specific Transcription Factors and a c-Abl-Dependent Signaling Axis," Mol. Cell. Biol. 2015; 35:1462-1476.
Tybulewicz et al., "Neonatal lethality and lymphopenia in mice with a homozygous disruption of the c-abl proto-oncogene," Cell. 1991; 65:1153-1163.
Udagawa et al., "Interleukin (IL)-6 induction of osteoclast differentiation depends on IL-6 receptors expressed on osteoblastic cells but not on osteoclast progenitors," J. Exp. Med. 182, 1461-1468 (1995).
Vashisht et al., "An approach for the identification of targets specific to bone metastasis using cancer genes interactome and gene ontology analysis," PLOS One. 7, e49401 (2012).
Wang et al., "The emerging role of ABL kinases in solid tumors," Trends Cancer 1, 110-123 (2015).
Wang et al., "ABL kinases promote breast cancer osteolytic metastasis by modulating tumor-bone interactions through TAZ and STAT5 signaling," Science Signaling 9 (issue 413): ra12. Cover article. (PMCID: PMC4991033).
Waning et al., "Molecular mechanisms of bone metastasis and associated muscle weakness," Clin. Cancer Res. 20, 3071-3077 (2014).
Weigel et al., "Preclinical and clinical studies of estrogen deprivation support the PDGF/Abl pathway as a novel therapeutic target for overcoming endocrine resistance in breast cancer," Breast Cancer Res. 2012; 14:R78.
Weilbaecher et al., "Cancer to bone: A fatal attraction," Nat. Rev. Cancer 11, 411-425 (2011).
Wetzel et al., "The Abl and Arg kinases mediate distinct modes of phagocytosis and are required for maximal Leishmania infection," Mol. Cell. Biol. 2012; 32:3176-3186.
Wong et al., "The BCR-ABL story: Bench to bedside and back," Ann. Rev. Immunol. 22, 247-306 (2004).
Wu et al., "Arg tyrosine kinase expression in human gastric adenocarcinoma is associated with vessel invasion," Anticancer Research. 2003; 23:205-210.
Wu et al., "AXL kinase as a novel target for cancer therapy," Oncotarget. 5, 9546-9563 (2014).
Yang et al., "Metabolic reprogramming for producing energy and reducing power in fumarate hydratase null cells from hereditary leiomyomatosis renal cell carcinoma," PLoS One. 2013; 8:e72179.
Yaqoob et al., "Neuropilin-1 stimulates tumor growth by increasing fibronectin fibril assembly in the tumor microenvironment," Cancer Res. 2012; 72:4047-4059.
Yin et al., "Mechanisms of cancer metastasis to the bone," Cell Res.15, 57-62 (2005).
Yuen et al., "TAZ expression as a prognostic indicator in colorectal cancer," PLOS One. 8, e54211 (2013).
Zanconato et al., "Genome-wide association between YAP/TAZ/TEAD and AP-1 at enhancers drives oncogenic growth," Nat. Cell Biol. 17, 1218-1227 (2015).
Zhang et al., "Targeting Bcr-Abl by combining allosteric with ATP-binding-site inhibitors," Nature. 463, 501-506 (2010).
Zhang et al., "Latent bone metastasis in breast cancer tied to Src-dependent survival signals," Cell. 16, 67-78 (2009).

(56) References Cited

OTHER PUBLICATIONS

Zhao et al., "Overcoming resistance to fulvestrant (ICI182, 780) by downregulating the c-ABL proto-oncogene in breast cancer," Mol. Carcinogenesis. 2011; 50:383-389.

Zheng et al., "PKD1 phosphorylation-dependent degradation of SNAIL by SCF-FBXO11 regulates epithelial-mesenchymal transition and metastasis," Cell. 2014; 26:358-373.

SEQUENCE LISTING

```
<160> NUMBER OF SEQ ID NOS: 34

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide

<400> SEQUENCE: 1
ttgcacacct caccatca                                                   18

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide

<400> SEQUENCE: 2
tacgcttccc gatgtttc                                                   18
```

```
<210> SEQ ID NO 3
<211> LENGTH: 18
<212> TYPE: DNA
<213> ORGANISM: Artificial Sequence
<220> FEATURE:
<223> OTHER INFORMATION: oligonucleotide

<400> SEQUENCE: 3
cactcgaacc tcaccaca                                                  18

<210> SEQ ID NO 4
<211> LENGTH: 18
<212> TYPE: DNA
<213> ORGANISM: Artificial Sequence
<220> FEATURE:
<223> OTHER INFORMATION: oligonucleotide

<400> SEQUENCE: 4
caagtgcttg agggcata                                                  18

<210> SEQ ID NO 5
<211> LENGTH: 20
<212> TYPE: DNA
<213> ORGANISM: Artificial Sequence
<220> FEATURE:
<223> OTHER INFORMATION: oligonucleotide

<400> SEQUENCE: 5
ctcatgacca cagtccatgc                                                20

<210> SEQ ID NO 6
<211> LENGTH: 20
<212> TYPE: DNA
<213> ORGANISM: Artificial Sequence
<220> FEATURE:
<223> OTHER INFORMATION: oligonucleotide

<400> SEQUENCE: 6
acacattggg ggtaggaaca                                                20

<210> SEQ ID NO 7
<211> LENGTH: 20
<212> TYPE: DNA
<213> ORGANISM: Artificial Sequence
<220> FEATURE:
<223> OTHER INFORMATION: oligonucleotide

<400> SEQUENCE: 7
ggctgtgagt accttgctgc                                                20

<210> SEQ ID NO 8
<211> LENGTH: 21
<212> TYPE: DNA
<213> ORGANISM: Artificial Sequence
<220> FEATURE:
<223> OTHER INFORMATION: oligonucleotide

<400> SEQUENCE: 8
ggcgctcatc ttcattcagg c                                              21

<210> SEQ ID NO 9
<211> LENGTH: 19
<212> TYPE: DNA
<213> ORGANISM: Artificial Sequence
<220> FEATURE:
<223> OTHER INFORMATION: oligonucleotide
```

<400> SEQUENCE: 9
ccagctactc ccgaggctg                                                19

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
cttgatccca cagggtgaag                                               20

<210> SEQ ID NO 11
<211> LENGTH: 21
<212> TYPE: DNA
<213> ORGANISM: Artificial Sequence
<220> FEATURE:
<223> OTHER INFORMATION: oligonucleotide

<400> SEQUENCE: 11
ggctctccag aacatcatcc c                                             21

<210> SEQ ID NO 12
<211> LENGTH: 21
<212> TYPE: DNA
<213> ORGANISM: Artificial Sequence
<220> FEATURE:
<223> OTHER INFORMATION: oligonucleotide

<400> SEQUENCE: 12
gggtgtcgct gttgaagtca g                                             21

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
ggtctctgag ggtcaagcag                                               20

<210> SEQ ID NO 14
<211> LENGTH: 17
<212> TYPE: DNA
<213> ORGANISM: Artificial Sequence
<220> FEATURE:
<223> OTHER INFORMATION: oligonucleotide

<400> SEQUENCE: 14
agttcatgag caacacg                                                  17

<210> SEQ ID NO 15
<211> LENGTH: 20
<212> TYPE: DNA
<213> ORGANISM: Artificial Sequence
<220> FEATURE:
<223> OTHER INFORMATION: oligonucleotide

<400> SEQUENCE: 15
agacagccac tcacctcttc                                               20

<210> SEQ ID NO 16
<211> LENGTH: 20

```
<212> TYPE: DNA
<213> ORGANISM: Artificial Sequence
<220> FEATURE:
<223> OTHER INFORMATION: oligonucleotide

<400> SEQUENCE: 16
tttcaccagg caagtctcct                                                20

<210> SEQ ID NO 17
<211> LENGTH: 20
<212> TYPE: DNA
<213> ORGANISM: Artificial Sequence
<220> FEATURE:
<223> OTHER INFORMATION: oligonucleotide

<400> SEQUENCE: 17
ccctacgggt tcacagtttc                                                20

<210> SEQ ID NO 18
<211> LENGTH: 21
<212> TYPE: DNA
<213> ORGANISM: Artificial Sequence
<220> FEATURE:
<223> OTHER INFORMATION: oligonucleotide

<400> SEQUENCE: 18
ttccggttcg gcttctgtaa c                                              21

<210> SEQ ID NO 19
<211> LENGTH: 20
<212> TYPE: DNA
<213> ORGANISM: Artificial Sequence
<220> FEATURE:
<223> OTHER INFORMATION: oligonucleotide

<400> SEQUENCE: 19
atcagacctt cgtgtcccag                                                20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide

<400> SEQUENCE: 20
atgtcttgtt cagccctgga                                                20

<210> SEQ ID NO 21
<211> LENGTH: 20
<212> TYPE: DNA
<213> ORGANISM: Artificial Sequence
<220> FEATURE:
<223> OTHER INFORMATION: oligonucleotide

<400> SEQUENCE: 21
ggctgggaga tgaccttcac                                                20

<210> SEQ ID NO 22
<211> LENGTH: 21
<212> TYPE: DNA
<213> ORGANISM: Artificial Sequence
<220> FEATURE:
<223> OTHER INFORMATION: oligonucleotide

<400> SEQUENCE: 22
```
aggcactggt gtggaactga c          21

<210> SEQ ID NO 23
<211> LENGTH: 20
<212> TYPE: DNA
<213> ORGANISM: Artificial Sequence
<220> FEATURE:
<223> OTHER INFORMATION: oligonucleotide

<400> SEQUENCE: 23
atgaactcgg cttcagccat          20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide

<400> SEQUENCE: 24
accatcctgc tccagtgttg          20

<210> SEQ ID NO 25
<211> LENGTH: 20
<212> TYPE: DNA
<213> ORGANISM: Artificial Sequence
<220> FEATURE:
<223> OTHER INFORMATION: oligonucleotide

<400> SEQUENCE: 25
cagcctcctc ctcacagaca          20

<210> SEQ ID NO 26
<211> LENGTH: 20
<212> TYPE: DNA
<213> ORGANISM: Artificial Sequence
<220> FEATURE:
<223> OTHER INFORMATION: oligonucleotide

<400> SEQUENCE: 26
gagccctgat cattccactg          20

<210> SEQ ID NO 27
<211> LENGTH: 22
<212> TYPE: DNA
<213> ORGANISM: Artificial Sequence
<220> FEATURE:
<223> OTHER INFORMATION: oligonucleotide

<400> SEQUENCE: 27
aaggaaagag tgtgggggta gg          22

<210> SEQ ID NO 28
<211> LENGTH: 20
<212> TYPE: DNA
<213> ORGANISM: Artificial Sequence
<220> FEATURE:
<223> OTHER INFORMATION: oligonucleotide

<400> SEQUENCE: 28
acgctgggaa caaagtcacg          20

<210> SEQ ID NO 29
<211> LENGTH: 21
<212> TYPE: DNA
<213> ORGANISM: Artificial Sequence

```
<220> FEATURE:
<223> OTHER INFORMATION: oligonucleotide

<400> SEQUENCE: 29
tgccaggaat gtgagagttt c                                              21

<210> SEQ ID NO 30
<211> LENGTH: 18
<212> TYPE: DNA
<213> ORGANISM: Artificial Sequence
<220> FEATURE:
<223> OTHER INFORMATION: oligonucleotide

<400> SEQUENCE: 30
aggagggagc gggagaag                                                  18

<210> SEQ ID NO 31
<211> LENGTH: 19
<212> TYPE: DNA
<213> ORGANISM: Artificial Sequence
<220> FEATURE:
<223> OTHER INFORMATION: oligonucleotide

<400> SEQUENCE: 31
gcagcgccgt ctccttcct                                                 19

<210> SEQ ID NO 32
<211> LENGTH: 21
<212> TYPE: DNA
<213> ORGANISM: Artificial Sequence
<220> FEATURE:
<223> OTHER INFORMATION: oligonucleotide

<400> SEQUENCE: 32
gcggcggagg aatgtaagct c                                              21

<210> SEQ ID NO 33
<211> LENGTH: 22
<212> TYPE: DNA
<213> ORGANISM: Artificial Sequence
<220> FEATURE:
<223> OTHER INFORMATION: oligonucleotide

<400> SEQUENCE: 33
catctctgaa aaggtagctc ag                                             22

<210> SEQ ID NO 34
<211> LENGTH: 19
<212> TYPE: DNA
<213> ORGANISM: Artificial Sequence
<220> FEATURE:
<223> OTHER INFORMATION: oligonucleotide

<400> SEQUENCE: 34
ctggagtcat ggaacattg                                                 19
```

COMPOSITIONS AND METHODS FOR THE TREATMENT OF CANCER

CROSS-REFERENCE TO RELATED APPLICATIONS

This application claims priority to U.S. Provisional Patent Application No. 62/289,979, filed Feb. 2, 2016, the entirety of which is hereby incorporated by reference.

STATEMENT REGARDING FEDERALLY SPONSORED RESEARCH OR DEVELOPMENT

This invention was made with Government Support under Federal Grant Nos. RO1 CA70940 and RO1 CA155160 awarded by the NIH. The Federal Government has certain rights in this invention.

FIELD OF THE INVENTION

The present disclosure provides, in part, new insight on the role of ABL kinases in breast and lung cancer progression and metastasis; provides allosteric inhibitors specific for the ABL kinases that are effective in the treatment of breast and lung tumor progression and metastasis; identifies molecules that regulate the ability of breast and lung cancer cells to metastasize to the bone, brain and other sites; provides new strategies for treatment of therapy-refractory breast and lung cancer; and provides new combination strategies for the treatment of breast and lung tumors.

BACKGROUND OF THE INVENTION

ABL Kinases

The ABL family of non-receptor tyrosine kinases, ABL1 (also known as cABL) and ABL2 (also known as Arg), links diverse extracellular stimuli to signaling pathways that control cell growth, survival, adhesion, migration, and invasion (Bradley et al., *J. Cell Sci.*, 2009; Colicelli, *Sci. Signal.*, 2010; Pendergast, *Adv. Cancer Res.*, 2002). ABL1 was first discovered as the oncogene in the Abelson murine leukemia virus (v-ABL) and was subsequently identified as an oncogene associated with chromosome translocations in BCR-ABL1-positive human leukemias. ABL tyrosine kinases play an oncogenic role in human leukemias (Wong, et al., *Ann. Rev. Immunol.*, 2004; Greuber et al., *Nat. Rev. Cancer*, 2013) and promote the progression of solid tumors (Greuber et al., *Nat. Rev. Cancer*, 2013; Ganguly et al., *Genes Cancer*, 2012). ABL kinases elicit pro-tumorigenic or anti-tumorigenic effects in breast cancer cells and promote cancer cell invasion (Blanchard et al., *PLOS One*, 2014; Gil-Henn et al., *Oncogene*, 2012; Sirvent et al., *Oncogene*, 2007; Srinivasan et al., *Oncogene*, 2008).

Pioneering studies on the ABL tyrosine kinases opened the door to seminal discoveries of the molecular basis of cancer. Among these was the finding that structural alterations of the cellular ABL (c-ABL, ABLI) tyrosine kinase as a consequence of viral fusion (Gag-ABL) and chromosomal translocation (BCR-ABL1) events promote leukemia in mice and humans, respectively (Wong et al., *Ann Rev. Immunology,* 2004). The Gag-ABL and BCR-ABL1 fusion proteins are constitutively active and drive cellular transformation. By contrast, the kinase activities of ABL1 and ABL2 are tightly regulated by intra- and intermolecular interactions as well as by phosphorylation (Colicelli et al., *Sci. Signal.,* 2010; Panjarian et al., *J. Biol. Chem.,* 2013).

Studies of the cell of origin of BCR-ABL-positive chronic myeloid leukemia (CML) demonstrated its presence in hematopoietic stem cells (HSCs). The recognition that small-molecule tyrosine kinase inhibitors (TKIs) could effectively treat human CML ushered in the era of targeted cancer therapies (Eide et al., *Curr. Hem. Malignancy Reports,* 2015). Subsequently, the emergence of resistance to ATP-competitive inhibitors of the BCR-ABL1 kinase led to the identification of diverse drug resistance mechanisms and provided a road-map for the development of alternative therapies in the treatment of leukemias and other malignancies.

ABL Structural Domains and Enzymatic Regulation

ABL1 and ABL2 share N-terminal regulatory and catalytic domains that are over 90% identical and include the Src homology 3 (SH3), SH2, and SH1 (tyrosine kinase) domains (FIG. 1). The C-terminus of both ABL kinases contains a conserved filamentous (F) actin-binding domain. ABL1 contains a G-actin (globular actin)-binding domain upstream of the F-actin-binding domain, whereas ABL2 has a second internal F-actin-binding domain and a microtubule-binding domain which are not found in ABL1 (FIG. 1). The ABL kinases share conserved PXXP motifs that mediate binding to SH3 domain-containing proteins. ABL1 has three nuclear localization signal (NLS) motifs and one nuclear export signal (NES) in its C-terminus, which mediates its nuclear-cytoplasmic shuttling.

By contrast, ABL2, which lacks the NLS motifs, localizes primarily to the cytoplasm and preferentially accumulates at F-actin-rich sites in the cell periphery, focal adhesions, adherens junctions, invadopodia, and phagocytic cups (Bradley et al., *J. Cell Sci.,* 2009). Alternative splicing of the first exons produces various ABL1 and ABL2 isoforms with distinct N-terminal sequences (FIG. 1). The 1b isoforms of both ABL kinases contain an N-terminal glycine that is myristoylated, while the 1a variants lack this site and the corresponding modification.

Multiple intramolecular interactions mediate ABL auto-inhibition and include the binding of the SH3 domain to the polyproline-containing linker sequence connecting the SH2 and kinase domains, as well as interactions of the SH2 domain with the C-terminal lobe of the kinase domain (SH1), leading to the formation of a SH3-SH2-SH1 clamp structure (Hantschel et al., *Nature Rev. Mol. Cell Bio.,* 2004). The auto-inhibited conformation of ABL kinases is stabilized by the binding of the myristoylated residue in the ABL N-terminus to a hydrophobic pocket within the C-lobe of the kinase domain in the myristoylated 1b isoform of the ABL kinases (FIG. 1). In addition, intermolecular interactions with distinct binding partners can negatively or positively regulate ABL kinase activity (Colicelli et al., *Sci. Signal.,* 2010). Intermolecular interactions that disrupt auto-inhibitory interactions result in stabilization of the active conformation of the ABL kinases and increased enzymatic activity. By contrast, intermolecular interactions that stabilize the inactive conformation of the ABL kinases inhibit enzymatic activity and downstream signaling. The activity of the ABL kinases can also be modulated by interactions with lipids such as phosphatidylinositol 4,5-bisphosphate (PIP2), which inhibits the ABL kinases in vitro and in cells; experimentally decreasing cellular PIP2 levels stimulates ABL kinase activity (Plattner et al., *Nat. Cell Biol.,* 2003).

The enzymatic activity of the ABL kinases can also be regulated by tyrosine phosphorylation (Colicelli et al., *Sci. Signal.,* 2010). This modification occurs in trans for both ABL1 and ABL2, and it is referred to as 'auto-phosphorylation.' ABL family kinases are also phosphorylated by SRC family kinases and receptor tyrosine kinases such as the platelet-derived growth factor receptor (PDGFR). Phosphorylation of key residues in the activation loop located at the interface between the small and large lobes of the catalytic domain of protein tyrosine kinases is necessary to achieve high catalytic activity. Among the tyrosine residues phosphorylated on ABL1 are Y412 in the activation loop (corresponds to ABL2 Y439) and Y245 in the SH2-kinase domain linker (corresponds to ABL2 Y272) (FIG. 1). Phosphorylation of these sites stabilizes the active ABL conformation, leading to enhanced signaling.

The presence of common and unique domains in ABL1 and ABL2 suggests that these kinases may exhibit overlapping as well as unique functions. The unique domains present in ABL1 and ABL2 control their differential subcellular localization and/or association with distinct protein complexes, leading to diverse functional roles for these kinases in various cell types.

Physiological Roles of Murine ABL Kinases

ABL1 and ABL2 function redundantly in some cellular contexts, but also have unique roles during mouse development and physiology in the adult. Analysis of mice with tissue-specific deletion of ABL1 and/or ABL2 revealed dependence of role on the cell type (Greuber et al., *J. Immunology*, 2012; Gu et al., *J. Immunology*, 2007; Chislock et al., *Proc. Natl. Acad. Sci. USA*, 2013; Wetzel et al., *Mol. Cell. Biol.*, 2012). Consistent with redundant roles for the murine ABL kinases, mice with global inactivation of both ABL1 and ABL2 die before embryonic day 11 (Koleske et al., *Neuron*, 1998). ABL1 single-knockout mice are viable or exhibit perinatal lethality, depending on the strain, and display phenotypes distinct from those presented by ABL2 global knockout mice (Schwartzberg et al., *Cell*, 1991; Tybulewicz et al., *Cell*, 1991; Qiu et al., *Proc. Natl. Acad. Sci. USA*, 2010; Moresco et al., *J. Neurosci.*, 2005; Li et al., *Nature Genetics*, 2000; Kua et al., *Nat. Cell Biol.*, 2012; Gourley et al., *Proc. Natl. Acad. Sci. USA*, 2009). Disruption of murine ABL1 on a mixed (129/SvEv and C57BL/6J) genetic background resulted in neonatal lethality in about 50% of the mice, a phenotype that was more severe on the C57BL/6J genetic background (Schwartzberg et al., *Cell*, 1991; Tybulewicz et al., *Cell* 1991). ABL1 knockout mice exhibit splenic and thymic atrophy, reduced numbers of B- and T-cells, cardiac abnormalities, and osteoporosis linked to defective osteoblast proliferation and premature senescence (Schwartzberg et al., Cell, 1991; Tybulewicz et al., *Cell*, 1991; Qiu et al., *Proc. Natl. Acad. Sci. USA*, 2010; Li et al., *Nature Genetics*, 2000; Kua et al., *Nat. Cell Biol.*, 2012). By contrast, ABL2 (Arg) knockout mice are viable and exhibit neuronal defects that include age-related dendrite destabilization and regression (Koleske et al., *Neuron*, 1998; Moresco et al., *J. Neurosci.*, 2005; Gourley et al., *Proc. Natl. Acad. Sci. USA*, 2009; Zheng et al., *Cancer Cell*, 2014). Conditional knockout mice with tissue-specific deletion of the ABL kinases revealed unique and overlapping roles for these kinases in neuronal cells, immune cells (T cells and myeloid cells), smooth muscle cells, and in cardiovascular development and function (Koleske et al., *Neuron*, 1998; Greuber et al., *J. Immunology*, 2012; Chislock et al., *Proc. Natl. Acad. Sci. USA*, 2013; Wetzel et al., *Mol. Cell. Bio.*, 2012; Gu et al., *Sci. Signal.* 2012; Cleary et al., *Resp. Res.*, 2013). For example, ABL kinases have redundant roles in mature T cells because a deletion of both ABL1 and ABL2 was necessary to inhibit TCR induced proliferation and cytokine production, as well as chemokine-induced migration (Gu et al., *J. Immunol.*, 2007; Gu et al., *Sci. Signal.*, 2012; Trampont et al., *Mol. Cell. Bio.*, 2015). ABL1 has a unique role in airway smooth muscle because disruption of ABL1 in these cells attenuated airway hyper-responsiveness and remodeling in a mouse model of allergen-induced asthma (Cleary et al., *Resp. Res.*, 2013). Distinct cellular functions of ABL1 and ABL2 might be mediated by their unique domains, differential subcellular localization, and/or association with distinct protein complexes.

ABL Activation in Leukemias and Development of Targeted Therapies

Chromosomal translocations are the hallmark of oncogenic activation of the ABL kinases in human leukemias (Ren et al., *Nat. Rev. Cancer*, 2005). Disruption of inhibitory ABL1 intramolecular interactions in Philadelphia positive (Ph+) human leukemias occurs as a consequence of the t(9; 22)(q34; q11) chromosome translocation that generates BCR-ABL1 fusion proteins with constitutive tyrosine kinase activity (FIG. 1). Chronic myelogenous leukemia (CML) begins with a chronic phase (CP-CML) that is characterized by expansion of the myeloid lineage and retention of hematopoietic differentiation (Wong et al., *Ann. Rev. Immun.*, 2004). This early phase can progress to a blastic phase (BP-CML) characterized by reduced cellular differentiation and displacement of mature cells with immature blasts. The majority of BP-CML patients harbor several genetic alterations in addition to BCR-ABL1. Three different BCR-ABL1 proteins have been identified that differ in the amount of BCR sequences retained in the fusion protein, leading to distinct types of leukemia: P210 BCR-ABL1 is causal in chronic myelogenous leukemia (CML); P185 BCR-ABL1 is found in 20-30% of adult and 3-5% of childhood B-cell acute lymphocytic leukemia (B-ALL); and P230 BCR-ABL1 is associated with neutrophilic CML and rare cases of CML (Advani et al., *Leukemia Res*, 2002). Oncogenic activation of ABL1 in the BCR-ABL1 fusion protein is dependent on the presence of the BCR N-terminal coiled-coil (CC) oligomerization domain. Multiple signaling pathways have been identified that function to mediate the oncogenic activity of BCR-ABL1, and include the RAS, NF-kB, PI3K/AKT, JUN, b-catenin, and STAT signaling pathways (Ren et al., *Nat. Rev. Cancer*, 2005).

Oncogenic activation of the ABL kinases via chromosomal translocations has also been shown to occur in Ph-negative human leukemias (Roberts et al., *N. Engl. J. Med.*, 2014; Kawai et al., *Leukemia Res.*, 2014; De Braekeleer et al., *Eur. J. Haem.*, 2011). ABL1 has been identified as a fusion partner with a number of genes in T cell acute lymphoblastic leukemia (T-ALL), B-ALL, AML, and other leukemias (FIG. 1). The ABL kinase fusions identified in a precursor B-ALL subtype lacking the BCR-ABL1 fusion (designated Ph-like ALL) are associated with poor outcome among children and adolescents (Roberts et al., *N. Engl. J. Med.*, 2014). Similarly to BCR-ABL1, several translocations retain the ABL1 SH3 and SH2 domains. Among these are the N-terminal fusion partners: ETV6 (TEL), EML1, NUP214, ZMIZ1, and SEPT9 (Roberts et al., *N. Engl. J. Med.*, 2014; Kawai et al., *Leukemia Res.*, 2014; De Braekeleer et al., *Eur. J. Haem.*, 2011). Other translocations fuse N-terminal sequences present in RCSD1, SFPQ, FOXP1, and SNX2 to the ABL1 SH2 domain and lack the SH3 domain (FIG. 1). Chimeric fusions involving the ABL2 gene have also been identified in rare leukemias. ETV6 and ZC3HAV1 are fused to ABL2 sequences upstream of the SH3 and SH2 domains, while RCSD1 and PAG1 are fused to the ABL2 SH2 domain (FIG. 1). Some fusion partners encode proteins that contain coiled-coil or helix-loop-helix motifs that promote oligomerization of the resulting chimeric proteins, leading to enhanced ABL kinase activity. However, the NUP-ABL1 fusion requires localization to the nuclear pore complex rather than oligomerization for enhanced transforming activity (De Keersmaecker et al., *Mol. Cell,* 2008).

Therapeutic Activity of ABL Kinases

The most successful example of molecular targeted therapy to date has been the development of tyrosine kinase inhibitors (TKIs) against BCR-ABL1 for the treatment of CML in the chronic phase (Table 1).

TABLE 1

Selective and Non-selective ABL Kinase Inhibitors

| Name | Alternative Name | Targets | Inhibitor Type | Regulatory Status | Year of Approval | Company |
|---|---|---|---|---|---|---|
| Imatinib | Gleevec/STI571 | ABL1, ABL2, BCR-ABL1, CSF1R, DDR1, KIT, NQO2, PDGFR1 | ATP-site, Type II | FDA approved for CML, Ph+ ALL, MDS/MPD, ASM, HES/CEL, DFSP, GIST | 2001 | Novartis |
| Dasatinib | Sprycel/BMS-354825 | ABL1, ABL2, BCR-ABL1, BLK, BTK, CSK, CSR1R, DDR1, DDR2, EGFR, ERBB2, FGR, FRK, FYN, GAK, GCK, HCK, ILK, KIT, LCK, LIMK1, LIMK2, LYN, MAP2K, MAP2K, MAP4K, PDGFR, RIPK2, SLK, SRC, SYK, TEC, TYK2, YES1 | ATP-competitive, Type I | FDA approved for CML, Ph+ ALL | 2006 | Bristol-Myers Squibb Company |
| Nilotinib | Tasigna/AMN107 | ABL1, ABL2, BCR-ABL1, CSF1R, DDR1, DDR2, KIT, NQO2, PDGFR | ATP-site, Type II | FDA approved for CML | 2007 | Novartis |
| Bosutimb | Bosulif/SKI-606 | ABL1, ABL2, BCR-ABL1, CAMK2G, CDK2, HCK, LYN, MAPKK1, MAPKK2, MAPKKK2, SRC | ATP-competitive, Type I | FDA approved for CML | 2012 | Pfizer Inc. |
| Ponatinib | Iclusing/AP24534 | ABL1, ABL2, BCR-ABL1, BLK, CSFR1, DDR1, DDR2, EPHRs, FGFR1, FGFR2, FGR, FLT2, FRK, FYN, HCK, LCK, LYN, RET, SRC, TEK, TIE2, TRKA, TRKB, TRKC, PDGFR, VEGFR1, VEGFR2, VEGFR3, YES1 | ATP-site, Type II | FDA approved for CML, Ph+ ALL | 2012 | Ariad Pharmaceuticals Inc. |
| Axitinib | Inlyta/AG013736 | BCR-ABL1 (T3151), KIT, PDGFR, VEGFR1, VEGFR2, VEGFR3 | ATP-competitive, Type I | FDA approved for Renal Cell Carcinoma | 2012 | Pfizer Inc. |
| Vandetanib | Caprelsa/ZD-6474 | ABL1, EGFR, RET, VEGFR | ATP-site, Type II | Thyroid Cancer | 2011 | AstraZeneca |

TABLE 1-continued

Selective and Non-selective ABL Kinase Inhibitors

| Name | Alternative Name | Targets | Inhibitor Type | Regulatory Status | Year of Approval | Company |
|---|---|---|---|---|---|---|
| GNF2, GNF5 | | ABL1, ABL2, BCR-ABL1 | Allosteric | Not FDA approved | | Novartis |
| ABL001 | | ABL1, ABL2, BCR-ABL1 | Allosteric | Phase I Trial for CML and Ph+ ALL | | Novartis |

The majority of CP-CML patients treated with the BCR-ABL1 inhibitor imatinib (Gleevec; STI571) as first-line therapy have durable remissions with five-year overall and progression free-survival rates approaching 90% (O'Hare et al., Nat. Rev. Cancer, 2012). However, imatinib is less effective for the treatment of blast crisis CML and Ph+ B-ALL patients. Several second- and third-generation TKIs targeting BCR-ABL1 have been approved or are under development for CML patients who are resistant or intolerant to imatinib (Table 1). Among these are dasatinib and nilotinib, which have been FDA- and European Medicines Agency (EMA)-approved as both frontline and second-line therapies, and bosutinib and ponatinib which have been FDA- and EMA-approved for second-line therapy to treat Ph+ leukemia patients with BCR-ABL1 kinase domain mutations (Eide et al., Curr. Hem. Malignancy Reports, 2015). Recently, axitinib, a vascular endothelial growth factor receptor (VEGFR) kinase inhibitor approved for second-line therapy of refractory renal cell carcinoma, was reported to potently inhibit the BCR-ABL1 (T315I) gatekeeper mutation, which confers resistance to imatinib, dasatinib and nilotinib (Pemovska et al., Nature, 2015). Threonine (T) 315 is known as the gatekeeper residue because it is found at the periphery of the nucleotide-binding site of the ABL1 kinase within the hinge region of the enzymatic cleft (Nagar et al., Cancer Res., 2002). T315 stabilizes the binding of imatinib, dasatinib and nilotinib through a hydrophobic pocket in the active site, and thus the T315I mutation elicits complete insensitivity to these ATP-competitive inhibitors. Interestingly, axitinib preferentially inhibits the BCR-ABL1 (T315I) mutant over wild-type BCR-ABL1 (Pemovska et al., Nature 2015). Thus, axitinib might be useful for the treatment of BCR-ABL1 (T315I)-driven CML and Ph+ B-ALL. Ponatinib also inhibits the BCR-ABL1 (T315I) mutant. The effectiveness of the ABL TKIs for the treatment of Ph-negative leukemias associated with multiple ABL fusion partners remains to be established.

ABL TKIs can be classified into three main classes based on their mechanism of action. The ATP-competitive inhibitors can be sub-classified into type 1 inhibitors targeting the active conformation of the kinase domain (dasatinib, bosutinib), and type 2 inhibitors targeting the inactive conformation of the kinase domain (imatinib, nilotinib, ponatinib). The third main class includes the allosteric inhibitors which do not target the ATP-binding pocket, but instead bind to regulatory domains to inhibit kinase activity.

Notably, the ATP-competitive kinase inhibitors imatinib, dasatinib, nilotinib, bosutinib, and ponatinib have broad target specificity and inhibit multiple tyrosine kinases in addition to ABL kinases (Table 1). Axitinib has a more restricted target specificity compared to other FDA-approved ATP-competitive inhibitors because it only targets KIT, PDGFRα, and VEGFRs in addition to the BCR-ABL1 (T315I) mutant kinase.

Among allosteric TKIs targeting ABL are GNF2 and GNF5, which bind to the myristoyl-binding pocket in the C-lobe of the ABL kinase domain (Table 1) (Zhang et al., Nature, 2010). In contrast to ATP-competitive inhibitors that target multiple kinases, the allosteric inhibitors are highly selective for the ABL kinases. These allosteric inhibitors were shown to inhibit BCR-ABL1-driven leukemogenesis in mice and sensitize mutant BCR-ABL1 to inhibition by ATP-competitive TKIs (Zhang et al., Nature, 2010). A Phase I, multicenter clinical trial with a novel allosteric inhibitor of BCR-ABL1 (ABL001; U.S. Patent App. Pub. No. 2013/0310395) that targets the myristoyl-binding pocket is currently ongoing for patients with refractory CML or Ph+ B-ALL (http://clinicaltrials.gov/show/NCT02081378) (Table 1).

Several studies have reported inhibitory and, in some cases, stimulatory effects of imatinib, nilotinib, dasatinib, and other TKIs on cancer cell proliferation, survival, and motility (Ganguly et al., Oncogene, 2012; Matei et al., Clin. Cancer Res., 2004; Stahtea et al., Int. J. Cancer, 2007). However, the cellular responses to these compounds cannot be solely attributed to inhibition of the ABL kinases because these compounds target numerous kinases and some non-kinase enzymes. Furthermore, TKIs such as nilotinib, imatinib and dasatinib were shown to have off-target effects leading to the formation of BRAF/RAF1 dimers and ERK activation in several cancer cell types (Packer et al., Cancer Cell, 2011). By contrast, paradoxical activation of RAF-ERK signaling was not induced by treatment of these cancer cells with allosteric inhibitors targeting the unique myristate-binding site in the ABL kinase domain.

ABL Kinases in Solid Tumors

Recently, the ABL family kinases, ABL1 and ABL2 have been shown to play a role in the progression of several solid tumors through activation mechanisms distinct from those involved in the generation of ABL-induced leukemias. Preclinical studies on small-molecule inhibitors of the ABL kinases suggest that their use may be of benefit in the treatment of selected solid tumors.

Activation of ABL kinases in solid tumors is not linked to chromosome translocation events as found in human leukemias, but instead is driven by enhanced ABL1 or ABL2 expression and/or activation due to amplification, increased gene expression, enhanced protein expression, and/or increased enzymatic activity in response to stimulation by oncogenic tyrosine kinases, chemokine receptors, oxidative stress, metabolic stress, and/or inactivation of negative regulatory proteins (Lin et al., Oncogene, 2008; Ganguly et al., Oncogene, 2012; Nature, 2012; Cerami et al., Cancer Discov., 2012; Sos et al., J. Clin. Invest., 2009; Simpson et al., J. Urol., 2005; Behbahani et al., World J. Urology, 2012).

The Cancer Genome Atlas (TCGA) and other large-scale sequencing projects report ABL amplification, somatic mutations, and/or increased mRNA expression in multiple solid tumors (www.cbioportal.org). These genomic alterations are more common in ABL2 than ABL1, with ABL2 alterations being observed in 24% of liver hepatocellular carcinomas, and to a lesser extent in uterine endometrioid carcinoma (20%), breast invasive carcinoma (19%), lung adenocarcinoma (15%), lung squamous cell carcinoma (12%), and kidney renal clear cell carcinoma (6%) (www.cbioportal.org). These findings are consistent with reports of elevated ABL2 expression in advanced high-grade breast, colorectal, pancreatic, renal, and gastric tumors (*Nature* 2012; Simpson et al., *J. Urol.*, 2005; Behbahani et al., *World J. Urology*, 2012; Crnogorac-Jurcevic et al., *Oncogene*, 2002; Wu et al., *Anticancer Research*, 2003). While ABL2 amplification and increased mRNA levels are genomic alterations found in a subset of human cancers, somatic mutations of ABL1 and ABL2 in solid tumors are rare, but have been reported in lung cancer and uterine corpus endometrioid carcinoma among other cancers (www.cbioportal.org). The role of these mutations in regulating ABL oncogenic activity remains to be determined.

Enhanced activation of the ABL kinases downstream of multiple receptor tyrosine kinases (RTKs), including the PDGFR, the ErbB family member EGF receptor (EGFR), and the hepatocyte growth factor receptor (MET), has been reported by multiple groups (Greuber et al., *Nat. Rev. Cancer*, 2013; Li et al., *PLoS One*, 2015; Fiore et al., *Oncogene*, 2014). Cancer cells expressing activated ErbB receptors exhibited rapid EGF-induced ABL kinase stimulation (Jones et al. *Nature*, 2006). Subsequent studies demonstrated that ABL kinases are tyrosine phosphorylated and activated in breast, lung, colorectal, gastric, renal, and prostate cancer cells, as well as in melanoma (Greuber et al., *Nat. Rev. Cancer*, 2013; Ganguly et al., *Oncogene*, 2012). The catalytic activity of the ABL kinases can be upregulated by ligand-dependent and ligand-independent activation of RTKs in cancer cells. Activation of ABL kinases in breast cancer cells has been reported to occur downstream of the EGFR, Her2 (ERBB2), insulin-like growth factor receptor (IGFR), and the CXCR4 chemokine receptor (Greuber et al., *Nat. Rev. Cancer*, 2013; Ganguly et al., *Oncogene*, 2012). ABL1 activation downstream of ligand-activated MET was shown in gastric carcinoma and hepatocellular carcinoma cells (Furlan et al., *Cell Death Diff.*, 2011), and ABL1 activation in human anaplastic thyroid carcinoma cells was induced by a constitutively active form of the receptor tyrosine kinase RET (Iavarone et al., *J. Biol. Chem.*, 2006).

ABL-Dependent Regulation of Cancer Cell Proliferation

The EPHB2 receptor tyrosine kinase can function as an oncogene during adenoma development and as a tumor suppressor in the progression of invasive colorectal cancer (Genander et al., *Cell*, 2009; Cortina et al., *Nature Genetics*, 2007). Genetic studies with ABL1-null mice showed that ABL1 is required for EPHB2-mediated proliferation in the small intestine and epithelium because deletion of ABL1 reduced the number of proliferating cells in these tissues (Genander et al., *Cell*, 2009). Inactivation of ABL1 in the Apc$^{min/+}$ mouse model of intestinal adenoma impaired EPHB2-mediated tumor promotion without affecting its tumor suppressor function (Genander et al., *Cell*, 2009; Kundu et al., *Science Trans. Med.*, 2015). Further, ABL1 inactivation inhibited tumor initiation by intestinal stem cells, decreased tumor load, and extended the lifespan of Apc$^{min/+}$ mice (Kundu et al., *Science Trans. Med.*, 2015). Interestingly, ABL1 knockdown or pharmacological inhibition in some human colon carcinoma cell lines expressing low levels of EPHB2 resulted in decreased levels of cyclin D1 and impaired cell proliferation (FIG. 2). Thus, ABL activity and function may become dissociated from EPHB2 signaling at later stages of adenocarcinoma progression.

ABL1 and ABL2 may have distinct roles in the regulation of breast cancer cell proliferation. Pharmacological inhibition or knockdown of ABL1 alone in MDA-MB-231 breast cancer cells and human mammary epithelial cells overexpressing nuclear geminin, a protein implicated in the regulation of chromosomal integrity, markedly decreased the growth of orthotopic mammary tumors (Blanchard et al., *PLoS One*, 2014). By contrast, knockdown of ABL2 alone in MDA-MB-231 breast cancer cells increased primary tumor size owing to enhanced cell proliferation (Gil-Henn et al., *Oncogene*, 2012). These results suggest that ABL1 and ABL2 may have opposing effects in the regulation of cell proliferation in some breast tumor types.

ABL-Mediated Metabolism and Oxidative Stress in Cancer

A recent breakthrough study revealed a crucial role for ABL1 in an aggressive form of hereditary kidney cancer (Sourbier et al., *Cancer Cell*, 2014). Patients with a germline mutation in fumarate hydratase (FH) are susceptible to the development of hereditary leimyomatosis and renal cell carcinoma (HLRCC). FH-deficient renal tumors are highly glycolytic, accumulate high levels of fumarate, lactate, and hypoxia stimulated transcription factor (HIF1α), and have decreased activity of AMP-activated kinase (AMPK) (Yang et al. *PLoS One*, 2013). The ABL1 kinase was found to be hyperactive in FH-deficient renal cancer cells in response to high fumarate levels (FIG. 2). Mechanistically, activation of ABL1 in HLRCC functions to promote aerobic glycolysis through activation of the mTOR-HIF1α pathway and also induces nuclear localization of the antioxidant response transcription factor NRF2 (FIG. 2). Thus, high ABL1 activity enables these tumors to simultaneously meet their high energetic needs and to neutralize the elevated levels of oxidative stress generated by excess fumarate accumulation in HLRCC. Importantly, ABL1 knockdown or inhibition with either imatinib or vandetanib (an inhibitor that also targets EGFR, RET, and VEGFR; Table 1), was cytotoxic to FH-deficient HLRCC (Sourbier et al., *Cancer Cell*, 2014). The anti-tumor activity of vandetanib in these cells was shown to be ABL1-dependent. Moreover, vandetanib was shown to potently inhibit the ABL1 kinase (IC$_{50}$=15 nM) in vitro and in cells. Vandetanib alone markedly inhibited the growth of HLRCC xenografts, and a combination of low-dose vandetanib with the AMPK activator metformin induced complete regression of the HLRCC tumors in 100% of the treated mice (Sourbier et al., *Cancer Cell*, 2014). ABL kinases have been shown to be activated in response to oxidative stress and reactive oxygen species (ROS) (Sun et al., *J. Biol. Chem.*, 2000). Elevated levels of ROS are a feature characteristic of many solid tumors, and are also an inevitable byproduct of cellular metabolism. Thus, the data on the role for ABL1 in HLRCC suggest that ABL1 kinase inhibitors could be developed for the treatment of FH-deficient tumors and other cancers with high levels of oxidative and metabolic stress.

Role of ABL Kinases in Cancer Cell Invasion and Metastasis

The progression of solid tumors requires invasion of primary tumor cells into the surrounding tissue, followed by intravasation, migration, extravasation, and formation of metastases at distant sites (Fidler, *Nat. Rev. Cancer*, 2003). The various steps in the metastatic cascade require dynamic remodeling of the actin cytoskeleton. ABL kinases have been shown to engage the actin polymerization machinery to promote formation of membrane protrusions, morphological changes, altered cell adhesion, migration, and invasion of diverse cell types (Bradley et al., *J. Cell Sci.*, 2009). Among the various functions of the ABL kinases, regulation of cell motility has been shown to be a predominant and evolutionarily conserved role for these kinases. A requirement for ABL kinases in cancer cell motility and invasion was shown downstream of IGF-1, EGF, serum, and chemokines (Greuber et al., *Nat. Rev. Cancer*, 2013). This requirement is consistent with the localization of ABL2 to invadopodia, which are actin-rich, protrusive membrane structures that promote remodeling of the extracellular matrix during tumor invasion (Smith-Pearson et al., *J. Biol. Chem.*, 2010; Mader et al., *Cancer Res.*, 2011). ABL kinases promote maturation of invadopodia and are required for matrix degradation and invasion in some but not all breast cancer types (Smith-Pearson et al., *J. Biol. Chem.*, 2010; Made et al., *Cancer Res.*, 2011; Chevalier et al., *PLoS One*, 2015). Among the actin cytoskeleton regulatory proteins targeted by ABL kinases at invadopodia are cortactin, N-WASP, WAVE, and the ABL interactor 1 (ABI1) adaptor protein (FIG. 2). Importantly, ABL kinases regulate the expression, localization, and activity of matrix metalloproteinase (MMP) during invadopodia maturation. Active ABL2 interacts with and promotes phosphorylation of the membrane type 1-matrix metalloproteinase (MT1-MMP, MMP14), and is required for its localization and function at invadopodia (Smith-Pearson et al., *J. Biol. Chem.*, 2010). Both ABL1 and ABL2 kinases were shown to regulate MMPs expression through STAT3-dependent and -independent pathways in melanoma cells (Ganguly et al., *Oncogene*, 2012). Knockdown of ABL2 alone decreased cancer cell invasion and intravasation following implantation of MDA-MB-231 cells in the mammary fat pad (Gil-Henn et al., *Oncogene*, 2012). A requirement for ABL kinases for invasion and metastasis of melanoma cells was also shown, which may be mediated in part by the NM23-H1 metastasis suppressor (Fiore et al., *Oncogene*, 2014). Active ABL kinases induced cathepsin-dependent lysosomal degradation of NM23-H1 in melanoma and breast cancer cells.

Role of ABL Kinases in Lung Cancer

Lung cancer is the leading cause of cancer mortality worldwide with a five-year survival rate of only ~10 to 15%, and often results in metastasis to the brain, bone and other organs. Among major drivers of lung cancer are activating mutations in RTKs and KRAS (V-Ki-ras2 Kirsten rat sarcoma viral oncogene homolog) as well as loss of tumor suppressors such as TP53, PTEN and LKB1/STK11. Unfortunately, targeted therapies against oncogenic RTKs have shown limited efficacy in the treatment of lung cancer patients due to intrinsic or acquired resistance. Similarly, patients with KRAS-mutant lung cancer exhibit poor outcome and have few tractable therapeutic options.

Role of ABL Kinases in Colorectal Cancer

A recent report demonstrated a novel role for ABL kinases in promoting colorectal cancer cell invasion and metastasis by linking the activation of Notch to the phosphorylation of TRIO (pY2681), leading to enhanced TRIO Rho-GEF activity and a corresponding increase of Rho-GTP levels (Sonoshita et al., *Cancer Discov.*, 2015). Activation of Notch by homozygous deletion of Aes (amino-terminal enhancer of split) in the intestinal epithelium of $Apc^{+/\Delta 716}$ polyposis mice resulted in enhanced RBPJ-mediated transcription, leading to increased levels of DAB1, a substrate and activator of the ABL kinases. Activated ABL in colorectal cancer cells induced tyrosine phosphorylation of TRIO on Y2681, leading to enhanced TRIO Rho-GEF activity (FIG. 2). Rho activation in colorectal cancer cells promoted invasion, extravasation and metastasis. Importantly, inhibition of ABL kinases in Apc/Aes compound knockout mice dramatically suppressed both invasion and intravasation incidence without affecting tumor size. These findings suggest that ABL kinases may function to link activation of other cell surface receptors to Rho signaling in different tumors. In this regard, it has also recently been shown that ABL kinases link the ligand-activated MET receptor tyrosine kinase to Rho activation that is required for cell scattering, tubulogenesis, migration, and invasion (Li et al., *PLoS One*, 2015).

Role of ABL Kinases in Metastatic Breast Cancer

Bone metastases occur in up to 70% of patients with advanced breast cancer and are associated with high mortality and morbidity (Weilbaecher et al., *Nat. Rev. Cancer*, 2011; Waning et al., *Clin. Cancer Res.*, 2014). Whereas the mechanisms that drive tumor cell homing, invasion, and colonization to the bone are poorly understood, it is increasingly apparent that bone metastasis requires interactions between tumor and stromal cells in the bone microenvironment (Cicek et al., *Cancer Metastasis Rev.*, 2006). For most patients with breast cancer, bone metastases are predominantly osteolytic. When breast cancer cells invade the bone microenvironment, they produce molecules that activate osteoclastic bone resorption, leading to the release of growth factors stored in the bone matrix to promote tumor growth. Currently, there are no available therapies to cure breast cancer metastasis. Thus, there is a need to identify molecules that could be targeted simultaneously in tumor and bone to disrupt the tumor cell-stromal cell interactions that drive metastasis.

Role for ABL Kinases in Cancer Drug Resistance

Enhanced activation of the ABL kinases has been reported in some cancers that have intrinsic or acquired resistance to chemotherapy. Hyper activation of both ABL1 and PDGFR was detected in aromatase inhibitor (AI)-resistant breast cancer patient specimens (Weigel et al., *Breast Cancer Res.*, 2012). ABL1 expression increased at the point of relapse in AI-treated patients, and correlated with increased expression of the Ki67 proliferation marker. In vitro studies showed that estrogen deprivation of MCF7 breast cancer cells, which became AI-resistant, was accompanied by up-regulation of PDGFR and ABL1 signaling (Weigel et al., *Breast Cancer Res.*, 2012). Treatment of these cells with nilotinib, a PDGFR and ABL inhibitor, suppressed proliferation and estrogen receptor (ER)-mediated transcription, in part by destabilizing the ER protein. Down regulation of ABL1 in some human breast cancer cell lines by RNA interference or imatinib treatment was reported to overcome resistance to fulvestrant, a compound that down regulates ERα levels and activity (Zhao et al., *Mol. Carcinogenesis*, 2011). Furthermore, in vitro studies using breast cancer cells resistant to lapatinib, an EGFR and ErbB2 inhibitor, showed that imatinib treatment or ABL1 depletion restored lapatinib sensitivity to these breast cancer cells (Lo et al., *Anticancer Research*, 2011). These studies suggest that inhibition of the ABL kinases may be effective in overcoming cancer cell resistance to diverse therapeutic agents.

A role for ABL kinase inhibitors in reversing resistance to doxorubicin in breast cancer (BT-549 and MDA-MB-468) and melanoma (WM3248) cell lines has been linked to at least two pathways (Sims et al., *PLoS One*, 2013). Imatinib blocked intrinsic resistance to doxorubicin by inhibiting STAT3-mediated cell survival and repressing NF-kB target gene expression. In addition, imatinib prevented acquired resistance by inhibiting the increased expression of the ABCB1 drug transporter, which mediates efflux of chemotherapeutic compounds such as doxorubicin. Similar to imatinib, other ATP-competitive inhibitors (nilotinib and dasatinib) have been reported to sensitize cancer cells to cytotoxic chemotherapies and targeted TKI therapies. However, the majority of these studies was carried out with ABL TKIs, and did not evaluate whether these effects were mediated specifically by inactivation of the ABL1 and/or ABL2 kinases in the cancer cells or in associated cells in the tumor microenvironment.

Targeting ABL Kinases in Endothelial Cells and Fibroblasts

Endothelial cells (ECs) and cancer-associated fibroblasts contribute to tumor progression and metastasis. TKIs such as imatinib have anti-angiogenic activity. For example, imatinib treatment of a mouse model of cervical cancer impaired angiogenesis in part by blocking the function of cancer-associated fibroblasts (Raimondi et al., *J. Ex. Med.*, 2014). The anti-angiogenic effects of imatinib have been largely attributed to inhibition of the PDGFR. However, ABL kinases, which are also targeted by imatinib, regulate diverse cellular processes in both ECs and fibroblasts. Conditional deletion of ABL1 in ECs in ABL2-null mice resulted in late-stage embryonic and perinatal lethality (Chislock et al., *Proc. Natl. Acad. Sci. USA*, 2013). Loss of ABL kinases led to increased endothelial cell apoptosis. ABL kinases play a dual role in angiopoietin (Angpt)/Tie2 signaling by regulating both Tie2 expression and activation of Tie2-mediated pathways required for cell survival. ABL kinases are also required for induction of endothelial permeability by VEGF and other factors (Sirvent et al., *Biology of the Cell*, 2008). Inactivation of the ABL kinases with pharmacological inhibitors or genetic inactivation in mice impaired VEGF-induced vascular permeability. Recently, ABL1 was shown to interact with neuropolin (NRP1) in human dermal microvascular ECs and link fibronectin-dependent activation of NRP1 to paxilin phosphorylation, actin remodeling, and EC mobility (Bi et al., *Am. J. Path.*, 2014). Moreover, ABL kinases regulate signaling downstream of multiple cell surface receptors in fibroblasts. ABL kinases are activated by ligand-activated PDGF receptor, leading to fibroblast proliferation and mobility (Yaqoob et al., *Cancer Res.*, 2012). ABL1 can also be activated downstream of the lipid second-messenger sphingosine 1 phosphate (S1P) and its receptor, leading to RAC activation and cytoskeletal remodeling required for fibroblast migration and invasion. ABL1 promotes S1P-dependent reciprocal signaling between stellateate cells and pancreatic cancer cells that is required for NF-κB activation and MMP9 production (Sun et al., *Carcinogenesis*, 2009). ABL1 also functions downstream of NRP1 in stromal myofibroblasts to induce integrin activation and fibronectin fibril assembly in the tumor microenvironment (Srinivasan et al., *Cancer Res.*, 2006). Thus, pharmacological inhibitors target ABL signaling not only the in tumor cells but also in the various cell types populating the tumor stroma, including ECs and fibroblasts, and may function to blunt angiogenesis through multiple pathways.

While imatinib sensitizes some breast cancer cells to apoptosis by treatment with cisplatin and other chemotherapeutic agents (Sims et al., *Biochem. Pharm.*, 2009), imatinib or GNF2 treatment was reported to protect mouse oocytes against cisplatin-induced cell death (Gonfloni et al., *Nat. Med.*, 2009). The disparate responses by germ cells versus cancer cells to DNA-damaging agents in the presence of ABL kinase inhibitors may be due to differential roles for ABL1 in the regulation of double-strand breaks and DNA damage signaling (Gonfloni, *Oncogene*, 2010). Further, different cellular responses may be elicited depending on the status of TP53 or its homolog TAp63, ABL1 enzymatic activity levels, ABL1 nuclear versus cytoplasmic localization, and the extent of DNA damage.

Therapeutic Potential for Tyrosine Kinase Inhibitors in Solid Tumors

The development of TKIs to treat patients with BCR-ABL1-positive leukemias is the best example of the successful application of targeted therapy. In contrast to the success of ATP-competitive inhibitors imatinib, nilotinib, and dasatinib in treating BCR-ABL1-induced leukemias, treatment of diverse solid tumors with these compounds has not achieved similar success (Ganguly et al., *Genes & Cancer*, 2012; Puls et al., *The Oncologist*, 2011). Drugs such as imatinib and nilotinib, shown to inhibit ABL kinases, have demonstrated mixed effectiveness for the treatment of solid tumors. The variable clinical responses to these TKIs may be due to the lack of the relevant oncogenic target, the presence of additional mutations driving the tumor, tumor heterogeneity, and/or dynamic reprogramming of signaling networks in response to TKI treatment (Stuhlmiller, et al., *Cell Rep.*, 2014; Duncan et al., *Cell*, 2012).

An alternative mechanism that underlies the poor response to TKI therapy is the paradoxical activation of proliferative pathways as a result of unintended targeting of other kinases. Imatinib, dasatinib and nilotinib, which have multiple cellular targets, drive the paradoxical activation of BRAF/C-RAF complexes leading to enhanced activation of the MEK-ERK pathway. This was demonstrated by the activation of BRAF/RAF1 complexes leading to enhanced activation of the MEK-ERK pathway by nilotinib, imatinib, and dasatinib in melanoma, lung, colorectal, pancreatic carcinoma cells, and BCR-ABL1 TKI-resistant leukemic cells expressing activated RAS (Packer et al., *Cancer Cell*, 2011). It is clear that the use ATP-competitive inhibitor drugs is inadequate for the treatment of solid tumors as monotherapies owing to the complexity of mutations even in early-stage tumors, and the potential for inappropriate activation (rather than inhibition) of proliferative pathways by some TKIs with multiple protein targets. In contrast to the ABL-targeted ATP-competitive TKIs, the ABL allosteric inhibitors GNF2 and GNF5, targeting the unique myristate binding site in the ABL kinase domain, do not induce the formation of BRAF/RAF1 dimers, and fail to elicit paradoxical activation of RAF-ERK signaling (Packer et al., *Cancer Cell*, 2011; and FIG. 14, respectively, for GNF2 and GNF5). To date no studies appear to have directly evaluated the consequences of specifically targeting the ABL kinases with selective kinase inhibitors in solid tumors including breast cancer.

Cancer cell types with hyper-activation of the ABL kinases as a consequence of amplification, enhanced expression, and/or elevated kinase activity would be more likely to rely on ABL signaling for tumor progression and metastasis. Thus, these cancer subtypes might benefit from treatment with ABL-selective TKIs such as the new allosteric inhibitors, resulting in the inhibition of ABL-dependent pathways in the tumor and associated stromal cells including endothelial cells, fibroblasts, and infiltrating myeloid cells.

The use of specific ABL-dependent signatures (genomic, transcriptional, or phospho-proteomic) in various tumors and associated stroma may be useful for the identification of those solid tumor types that might benefit from the use of ABL TKIs, in combination with other agents, to impair metastatic progression and block the development of chemoresistance. Thus, it may be important to identify those tumors that may benefit from therapies with selective ABL TKIs in combinations to prevent the emergence of therapy resistance.

SUMMARY OF THE INVENTION

Accordingly, in one aspect the invention relates to a method of treating cancer in a subject suffering from cancer, comprising inhibiting ABL kinase activity by administering an ABL-specific inhibitor, provided that no non-specific ABL inhibitor is administered to the subject.

In another aspect, the invention relates to a method of treating breast cancer in a subject suffering from breast cancer, comprising inhibiting ABL kinase activity by administering an ABL-specific inhibitor.

In another aspect, the invention relates to a method of reducing bone metastasis associated with cancer in a subject suffering from cancer, comprising administering an ABL-specific inhibitor.

In another aspect, the invention relates to a method of reducing tumor-induced osteolysis associated with breast cancer in a subject suffering from breast cancer, comprising administering an ABL-specific inhibitor.

In another aspect, the invention relates to a method of determining whether a subject suffering from breast cancer is likely to develop related bone metastasis, comprising: determining expression levels of at least one gene selected from the group consisting of ABL2, TAZ, AXL, STAT5A, STAT5B, TNC, MMP1, CTGF, and IL6 in a biological sample, wherein a level of expression of the at least one gene at least 3-fold greater than normal tissue indicates that the subject has an increased risk of developing breast cancer-related bone metastasis.

In another aspect, the invention relates to a method of treating breast cancer in a subject suffering from breast cancer, comprising: ordering a test which determines expression levels of at least one gene selected from the group consisting of ABL2, TAZ, AXL, STAT5A, STAT5B, TNC, MMP1, CTGF, and IL6 in a biological sample; selecting subjects having a level of expression of the at least one gene wherein a level of expression of the at least one gene at least 3-fold greater than normal tissue; and, administering an ABL-specific inhibitor to the selected subjects.

In another aspect, the invention relates to a method of reducing bone metastasis associated with cancer in a subject suffering from cancer, comprising: ordering a test which determines expression levels of at least one gene selected from the group consisting of ABL2, TAZ, AXL, STAT5A, STAT5B, TNC, MMP1, CTGF, and IL6 in a biological sample; selecting subjects having a level of expression of the at least one gene at least 3-fold greater than normal tissue; and, administering an ABL-specific inhibitor to the subjects.

*P<0.05, **P<0.01, two-way ANOVA followed by Tukey's post hoc test. n=3 biological replicates unless otherwise indicated.

Figure 8:
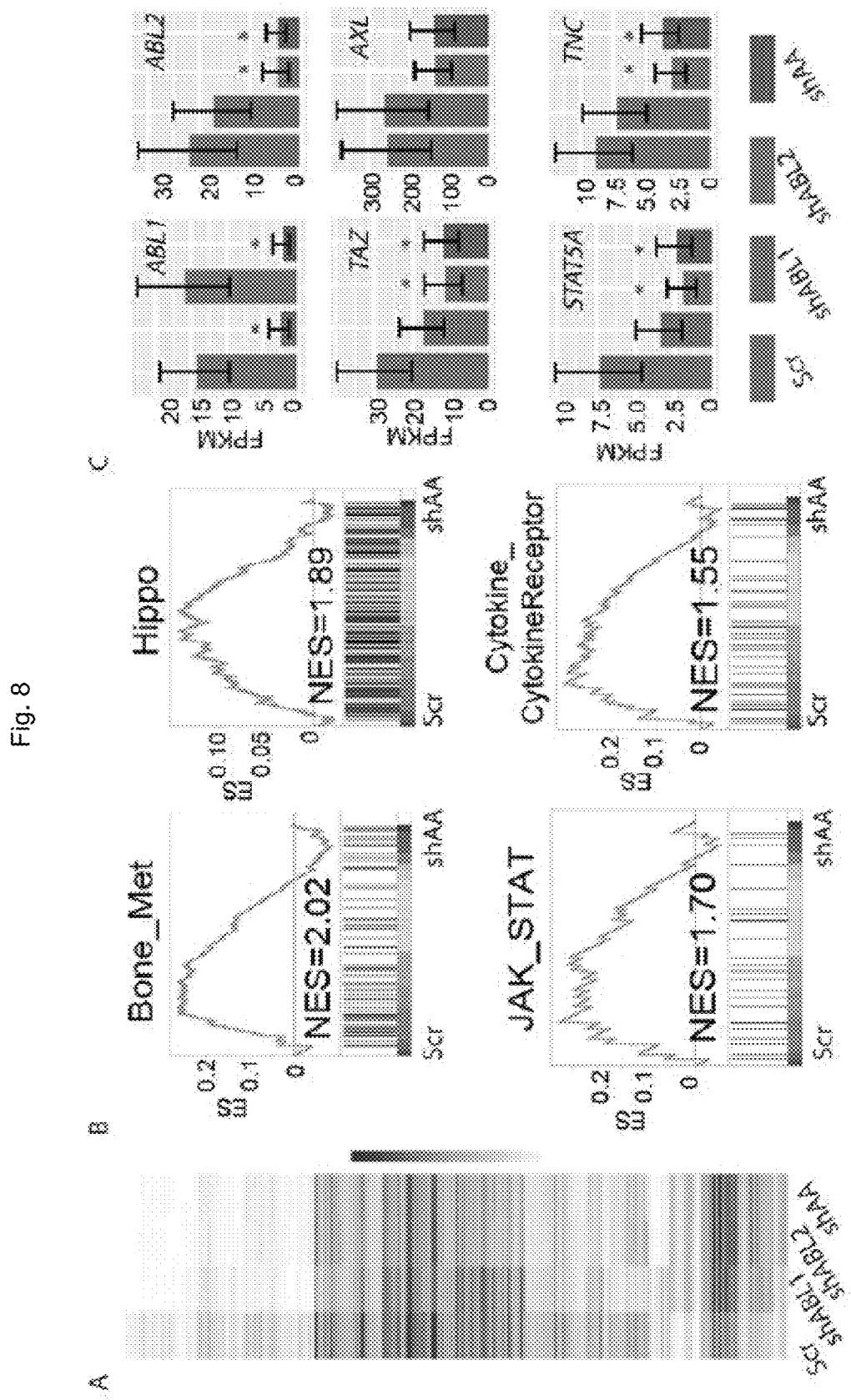

FIG. 8 demonstrates that ABL kinases regulate the expression of genes in the JAK/STAT and Hippo pathway signatures in metastatic breast cancer cells. (A) CummeRbund heat map of genes that were differentially expressed in control and single and double ABL1 and ABL2 knockdown cells. (B) GSEA analysis of the indicated gene signatures in ABL1/ABL2 knockdown cells compared with control cells (Scr). NES, normalized enrichment score. (C) Expression of the indicated genes in control, ABL1 or ABL2 single-knockdown, and ABL1/ABL2 double-knockdown cells quantified using Cufflinks CuffDiff. *Significantly different from control cells (P<0.05 after Benjamini-Hochberg correction by multiple testing). Error bars represent SD. n=3 biological replicates for (A) and (C).

Figure 9:
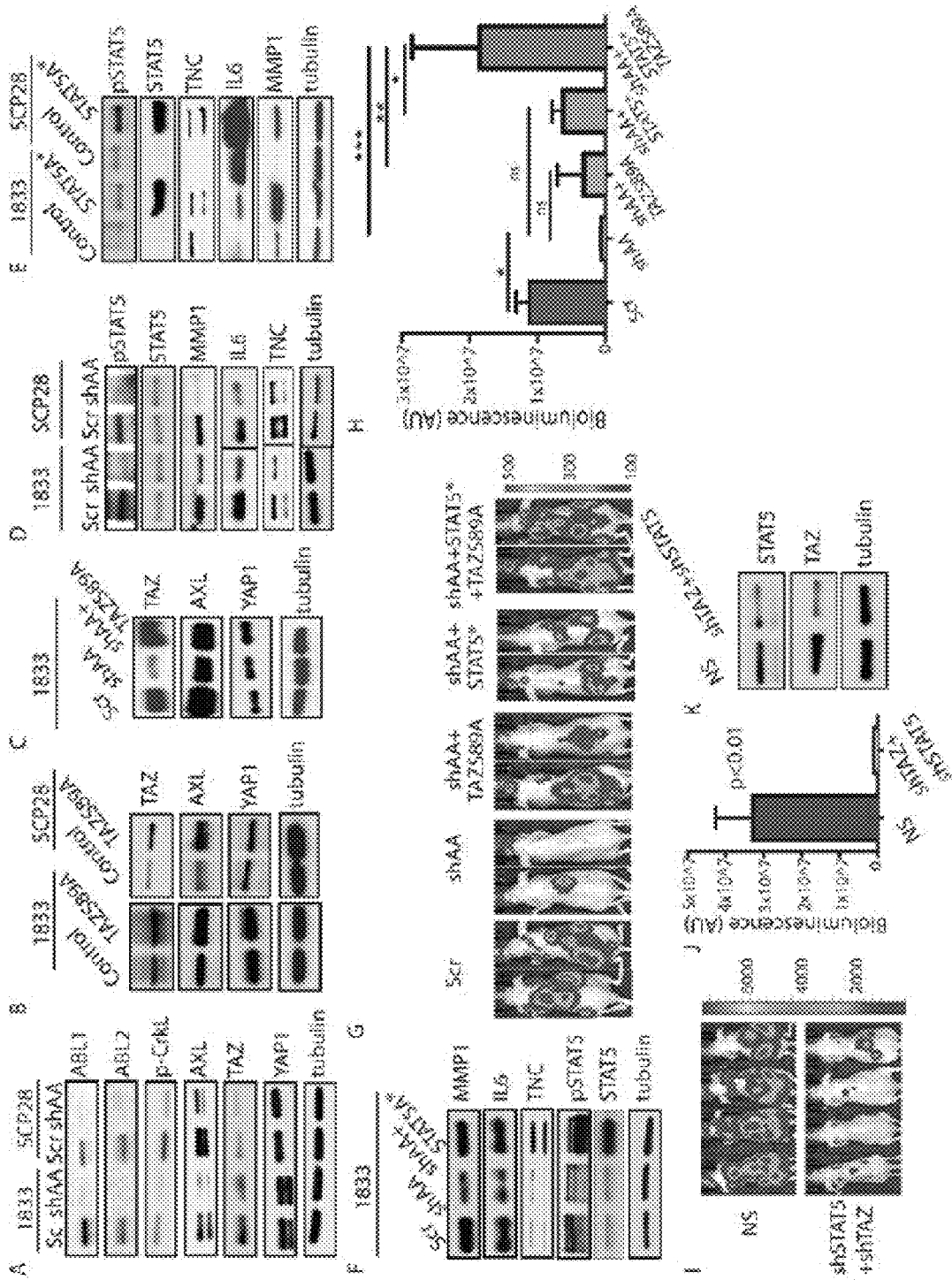

FIG. 9 shows that ABL kinases are required for TAZ and STAT5 signaling in breast cancer cells. (A to C) immunoblots with the indicated antibodies were performed on whole-cell lysates of 1833 and SCP28 cells. (D) immunoblots were performed on whole-cell lysates (pSTAT5, STAT5 and tubulin) or conditioned medium (MMP1, IL-6 and TNC). (E) Immunoblots were performed on whole-cell lysates (pSTAT5, STAT5, and tubulin) or conditioned medium (MMP1, IL-6 and TNC) of parental 1833 and SCP28 cells. (F) Immunoblotting with the indicated antibodies were performed on whole-cell lysates (pSTAT5, STAT5, and tubulin) or conditioned medium (MMP1, IL-6 and TNC) of 1833 cells. For (A) to (F), n=3 blots. (G) Bioluminescent images of representative mice at day 25 after intra-cardiac injection of 1833 cells. (H) quantification of bone metastasis. n=5 mice per group. *P<0.05; P<0.01, *P<0.001 one-way ANOVA followed by Tukey's post hoc test. (I and J) Bioluminescent images (I) and quantification (J) of bone metastasis from representative mice at day 25 after intra-cardiac injection of 1833 cells transfected with control (NS) or shRNAs against STAT5 and TAZ (shSTAT5/shTAZ). n=8 mice per group. (K) Immunoblots were performed on whole-cell lysates n=3 blots. NS—Nonspecific.

Figure 10:
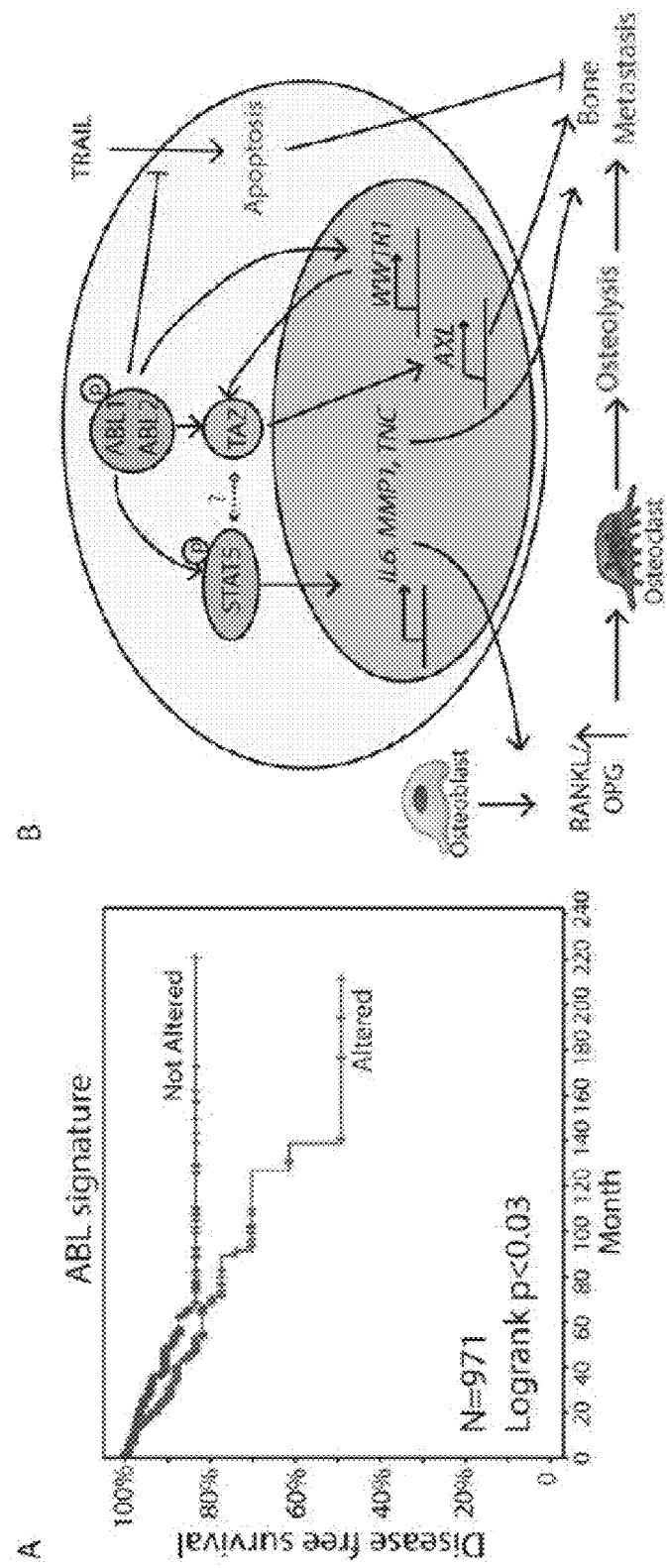

FIG. 10 demonstrates that ABL kinases activate the TAZ and STAT5 pathways to promote breast cancer bone metastasis. (A) Kaplan-Meier representation of the probability of cumulative overall disease-free survival in TOGA data set with 971 invasive breast cancer patients according to whether the ABL signature (ABL2, TAZ, AXL, CTGF, STAT5A, STAT5B, TNC, IL6, and MMP1) was altered or not. P value was derived by the log-rank test. (B) Model for the role of ABL kinases in the regulation of breast cancer bone metastasis.

Figure 11:
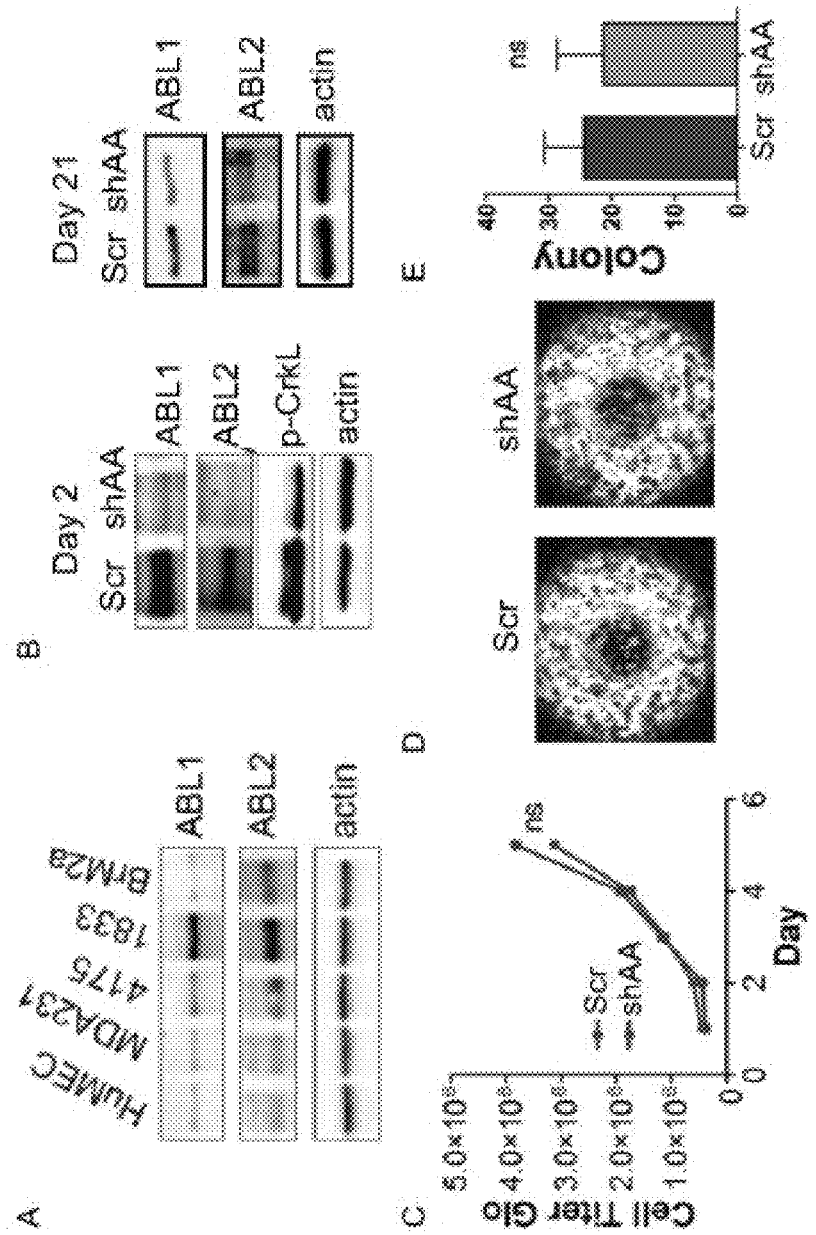

FIG. 11 demonstrates that ABL family protein abundance is increased in breast cancer cells with enhanced bone metastatic activity and ABL1/ABL2 depletion does not affect proliferation in vitro. (A) Immunoblotting with the indicated antibodies was performed on whole-cell lysates from human mammary epithelial cells (HuMEC), MDA-MB-231 (parental) and MDA-MB-231 derived breast cancer cell lines: 4175 (lung metastasis), 1833 (bone metastasis), and BrM2a (brain metastasis); n=3 blots. (B) Immunoblotting with the indicated antibodies was performed on whole-cell lysates from 1833 control (Scr) and ABL1/ABL2 knockdown cells (shAA) at 2 or 21 days after knockdown; n=2 blots. (C) Control and knockdown 1833 breast cancer cells were seeded onto 96-well plates and cell proliferation and survival were analyzed daily using CellTiter-Glo (days 1-5). n=3 biological replicates. (D-E) Control and knockdown breast cancer cells were seeded in matrigel (D) and colony formation was quantified (E) on day 21. n=3 biological replicates.

Figure 12:
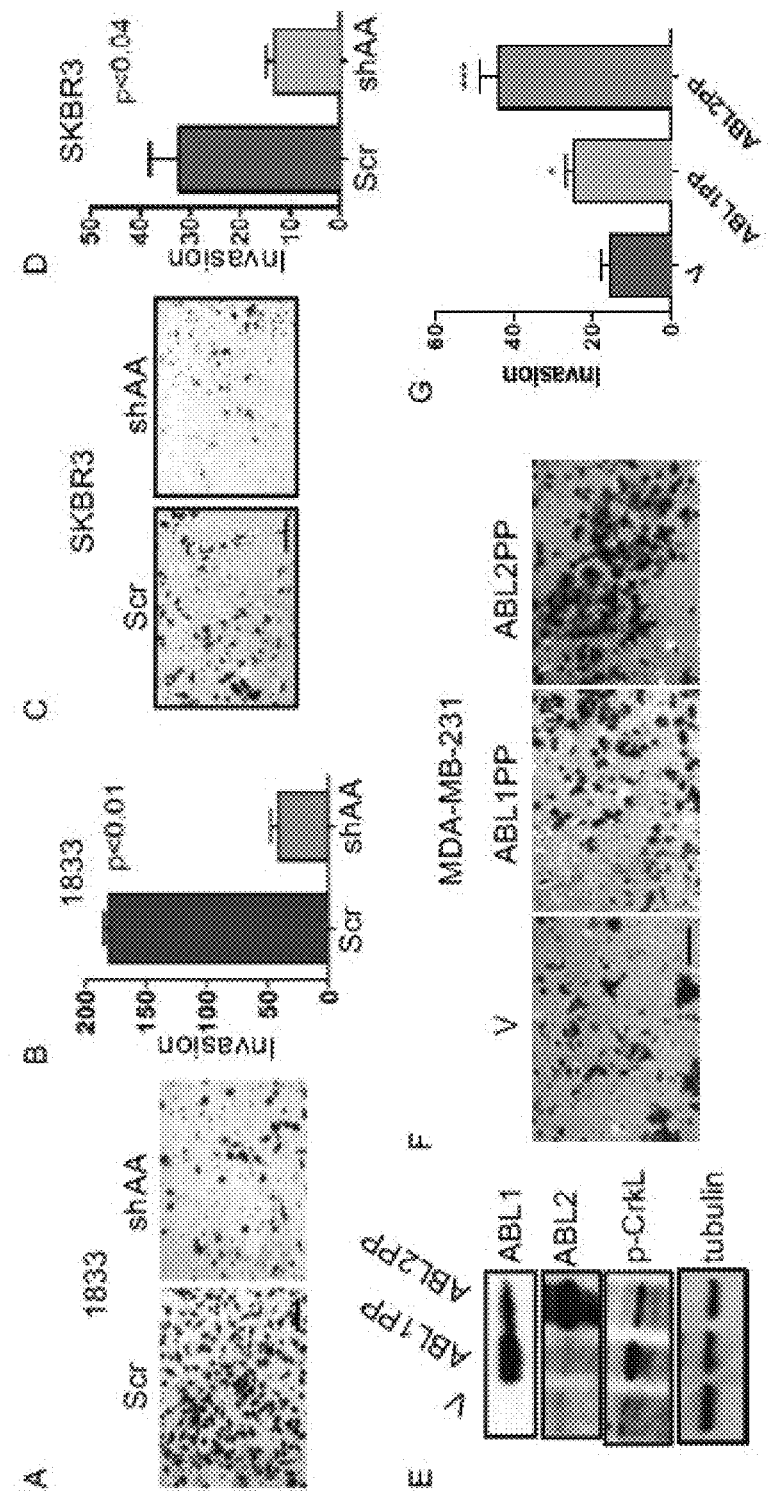

FIG. 12 demonstrates that ABL kinases promote breast cancer cell invasion. (A-D) Control (Scr) and ABL1/ABL2 knockdown (shAA) 1833 (A, B) and SKBR3 (C, D) breast cancer cells were plated on the upper wells of matrigel chambers; cells on the under surface of the matrigel membrane were stained (A, C) and quantified (B, D). n=3 biological replicates. (E) Representative immunoblots of whole cell lysates from MDA-MB-231 cells transduced with retroviruses encoding control vector (V), constitutively active ABL1 (ABL1PP), and constitutively active ABL2 (ABL2PP); n=2 blots. (F, G) Cells transduced with the indicated retroviruses were plated on the upper wells of matrigel chambers; cells on the under surface of the matrigel membrane were stained (F) and quantified (G). Scale bar=100 µM. n=3 biological replicates.

Figure 13:
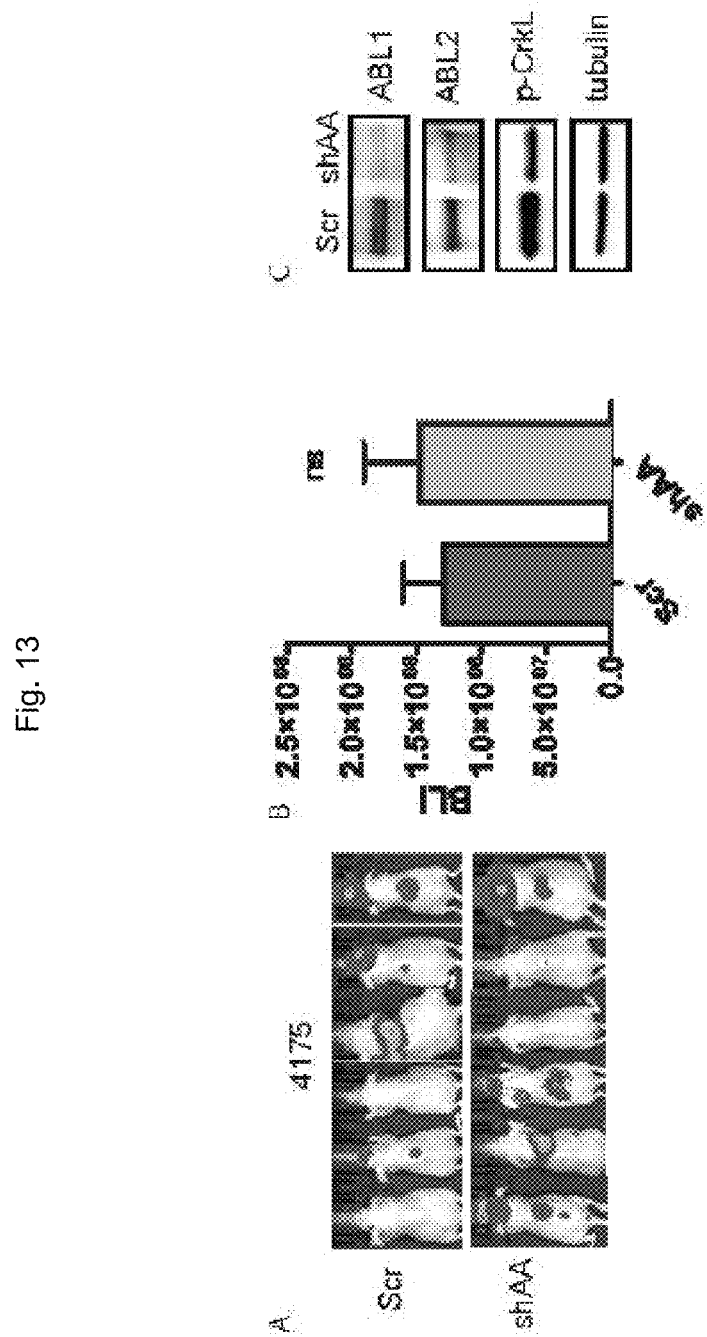

FIG. 13 demonstrates that depletion of ABL kinases does not inhibit metastasis of 4175 breast cancer cells, which show tropism to the lung. (A-B) Bioluminescent images (A) of bone metastases from representative mice in each group at day 22 after inoculation of control (Scr) and ABL1/ABL2 knockdown (shAA) 4175 breast cancer cells, and quantification (B) of bone metastases; N=8 mice/group. (C) Representative immunoblots of whole-cell lysates from 4175 cells transduced with control shRNA (Scr) and ABL1/ABL2 shRNAs (shAA) and blotted with the indicated antibodies; n=3 blots.

Figure 14:
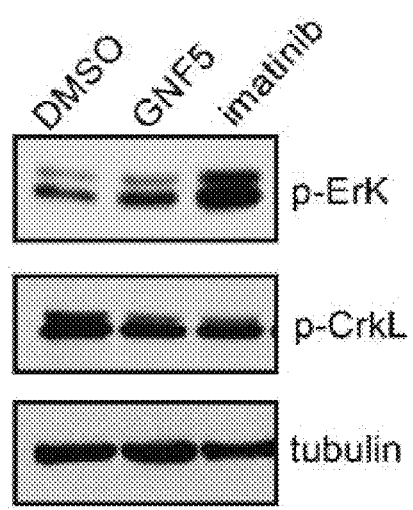

FIG. 14 demonstrates that treatment of breast cancer cells with imatinib, but not GNF5, promotes ERK activation. Triple-negative 1833 breast cancer cells were treated with vehicle (DMSO), 10 µM imatinib (STI571), and 10 µM GNF5 for 3 hours; Western blots with antibodies against phospho-Erk (p-Erk), phospho-CrkL (p-CrkL) and tubulin (loading control) were performed on whole cell lysates; n=3 blots.

Figure 15:
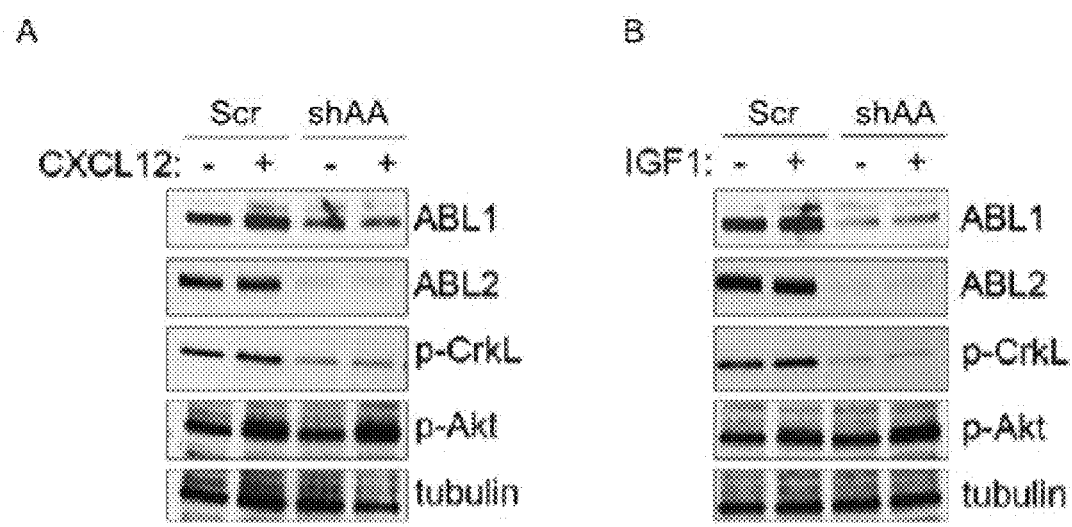

FIG. 15 demonstrates that CXCL12- and IGF1-mediated survival pathways are independent of ABL kinases. (A) Control and ABL1/ABL2 knockdown 1833 breast cancer cells were incubated with or without CXCL12 (300 ng/mL) for 30 min; immunoblotting using the indicated antibodies was performed on whole-cell lysates. n=2 blots. (B) Control and ABL1/ABL2 knockdown 1833 cells were incubated with or without IGF1 (10 ng/mL) for 30 min; immunoblots using the indicated antibodies were performed on whole-cell lysates. n=3 blots.

Figure 16:
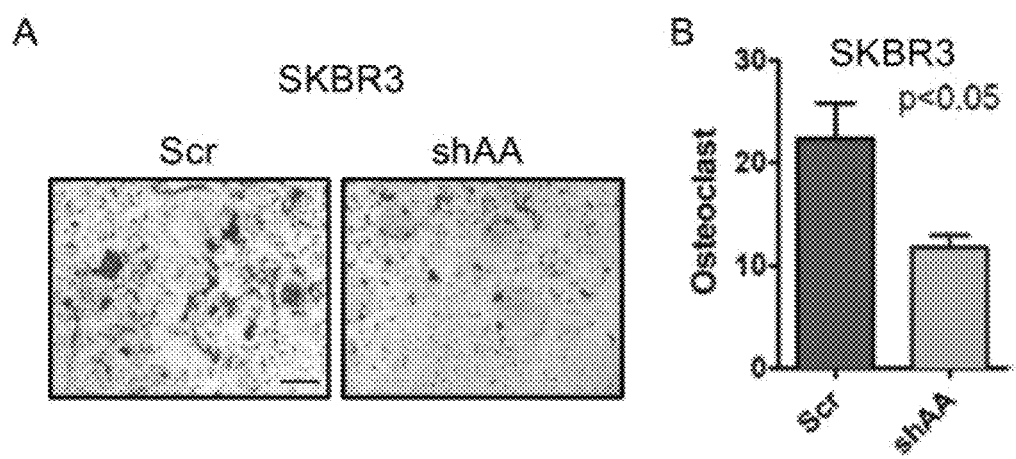

FIG. 16 demonstrates that depletion of ABL kinases in SKBR3 breast cancer cells decreases tumor-induced osteoclast activation. (A) TRAP staining of bone marrow cells treated with conditioned medium harvested from control (Scr) and ABL1/ABL2 (shAA) knockdown SKBR3 breast cancer cells. Scale bar=200 µM. (C) Quantification of TRAP+ bone marrow cells in (A). n=3 biological replicates.

Figure 17:
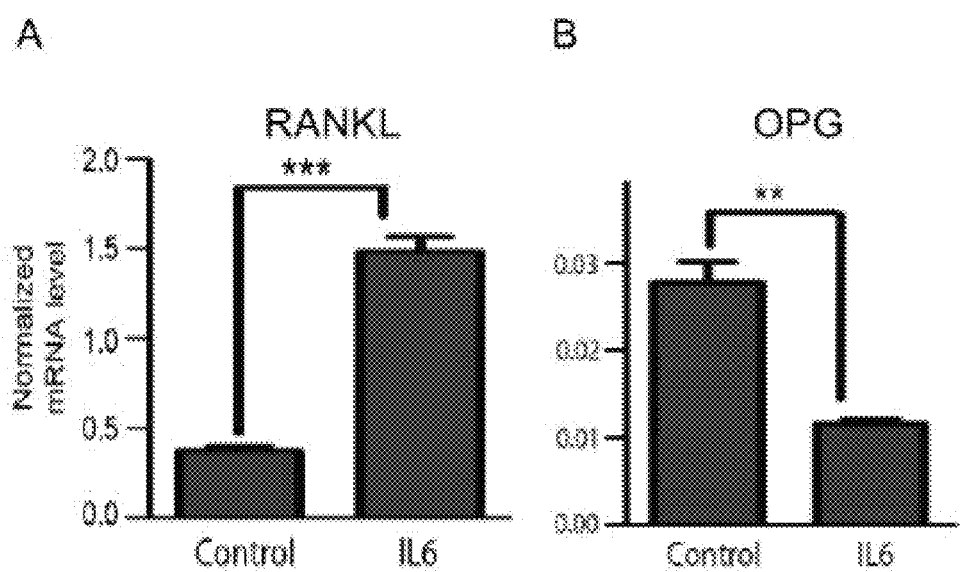

FIG. 17 demonstrates that 1L6 affects RANKL and OPG expression in osteoblasts. (A) Murine 7F2 osteoblasts were treated with or without IL6 (0.1 ng/mL) for 24 h and RANKL mRNA expression was detected by RT-PCR. (B) 7F2 osteoblasts were treated with or without IL6 (0.1 ng/mL) for 24 h and OPG mRNA expression was detected by RT-PCR. n=3 biological replicates. *p<0.05; p<0.01; *p<0.001.

Figure 18:
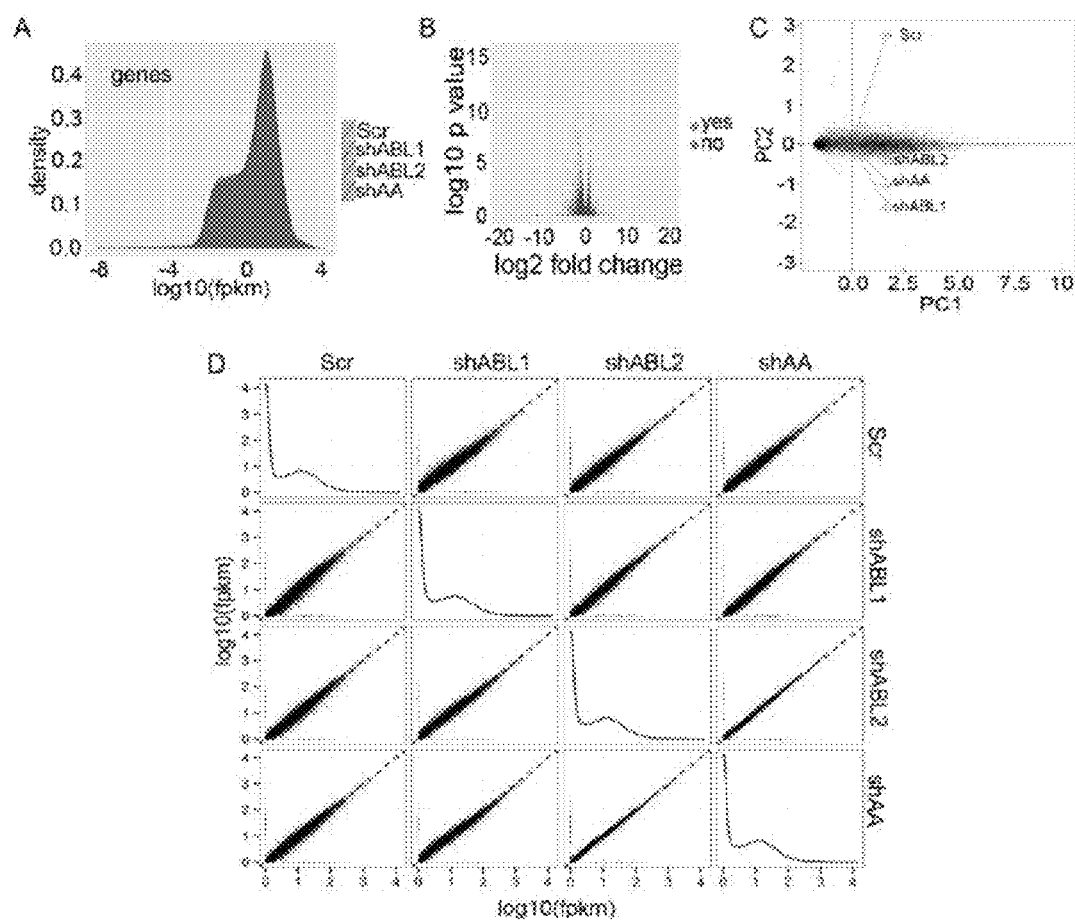

FIG. 18 illustrates quality control and global statistics of RNAseq analysis for transcriptome comparison of control versus ABL1/ABL2 knockdown breast cancer cells. (A) Distribution of the expression of genes from the indicated samples. (B) CummeRbund volcano plot reveals genes that differ significantly between control (Scr) and ABL1/ABL2 knockdown (shAA) samples. (C) Principal component analysis reveals that the control sample has a different gene expression pattern compared with single or double ABL1/ABL2 knockdown samples. (D) Scatter plots highlight general similarities and specific outliers between indicated conditions.

Figure 19:
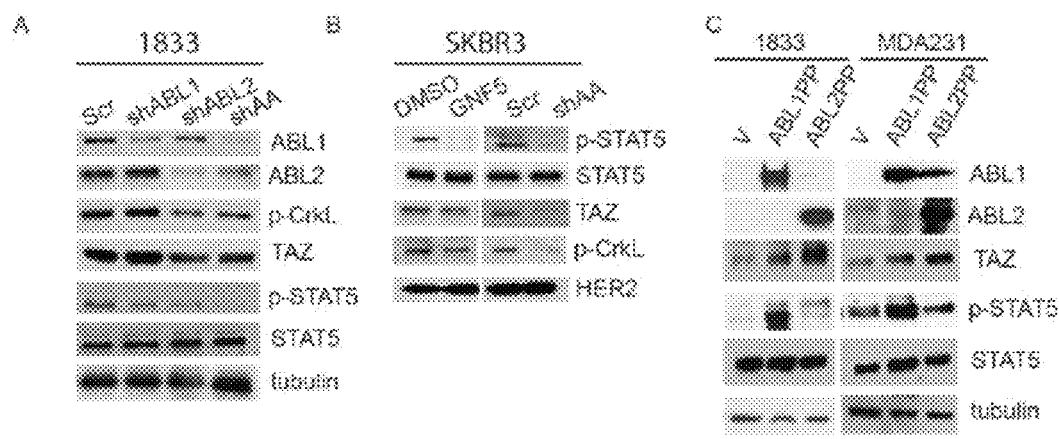

FIG. 19 demonstrates that ABL kinases increase TAZ protein abundance and STAT5 phosphorylation. (A-C). Immunoblotting with indicated antibodies was performed on whole cell lysates. (A, B) Depletion or pharmacological inactivation of the ABL kinases decreases TAZ abundance and STAT5 phosphorylation (p-STAT5) in 1833 and SKBR3 breast cancer cells. (C) Activated ABL kinases increases TAZ protein abundance and STAT5 phosphorylation (p-STAT5) in 1833 and MDA-MB-231 (MDA231) breast cancer cells. n=3 blots for (A) to (C).

Figure 20:
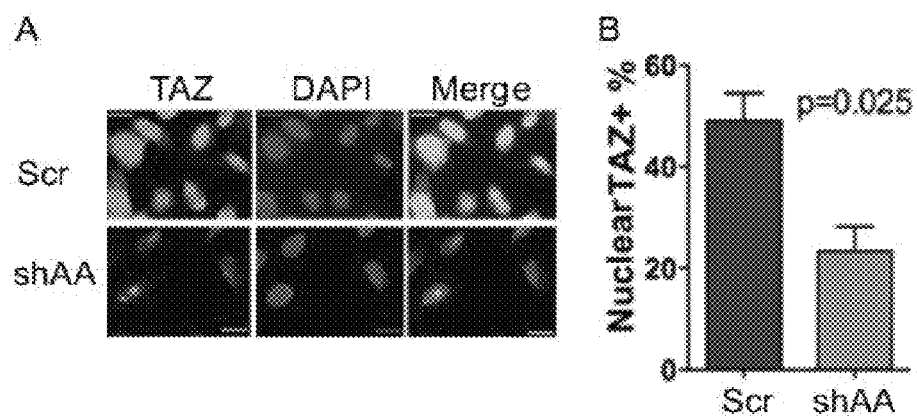

FIG. 20 demonstrates that depletion of ABL kinases reduces the abundance of TAZ in the nucleus. (A) 1833 cells were transduced lentiviruses encoding control shRNA (Scr) or shRNAs against ABL1/ABL2 (shAA). TAZ protein abundance and subcellular localization were analyzed by immunofluorescence staining for endogenous TAZ (green); DAPI (blue) was used to stain cell nuclei. Scale bar=20 µM. (B) Quantification of the percentage of nuclear TAZ-positive cells in (A). n=3 biological replicates.

Figure 21:
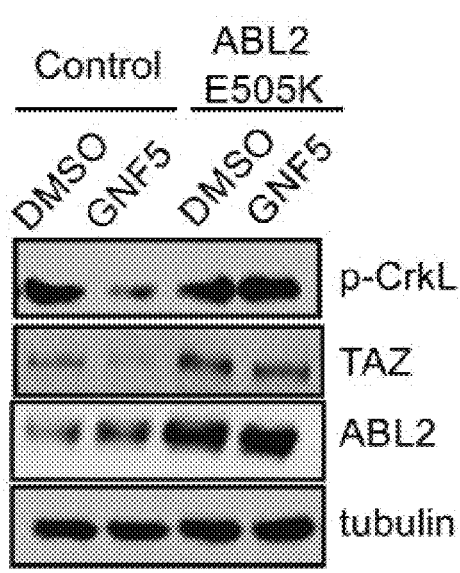

FIG. 21 demonstrates that allosteric inhibition of ABL kinases activity decreases TAZ protein abundance. Control 1833 cells or 1833 cells expressing murine Ab12-E505K mutant protein were plated ($3 \times 10^5$ cells per group) in six well plates. Cells were then treated with vehicle (DMSO) or GNF5 (20 µM) for 24 hours and immunoblotted with the indicated antibodies. n=3 blots.

Figure 22:
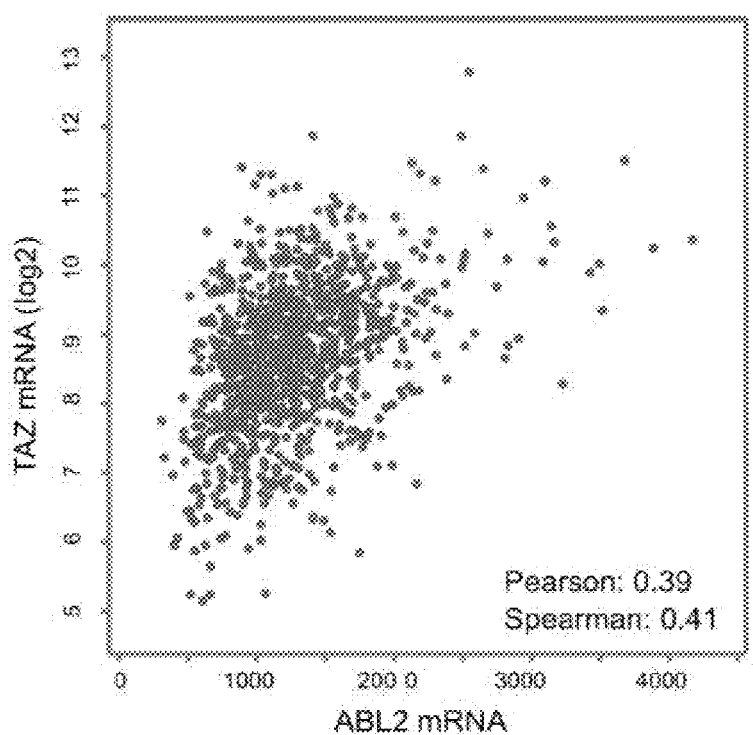

FIG. 22 shows that ABL2 mRNA expression positively correlates with TAZ mRNA expression in invasive breast cancer patients. Co-expression analysis was performed for the Breast Invasive Carcinoma dataset (N=971 patients) (TCGA) using www.cbioportal.org.

Figure 23:
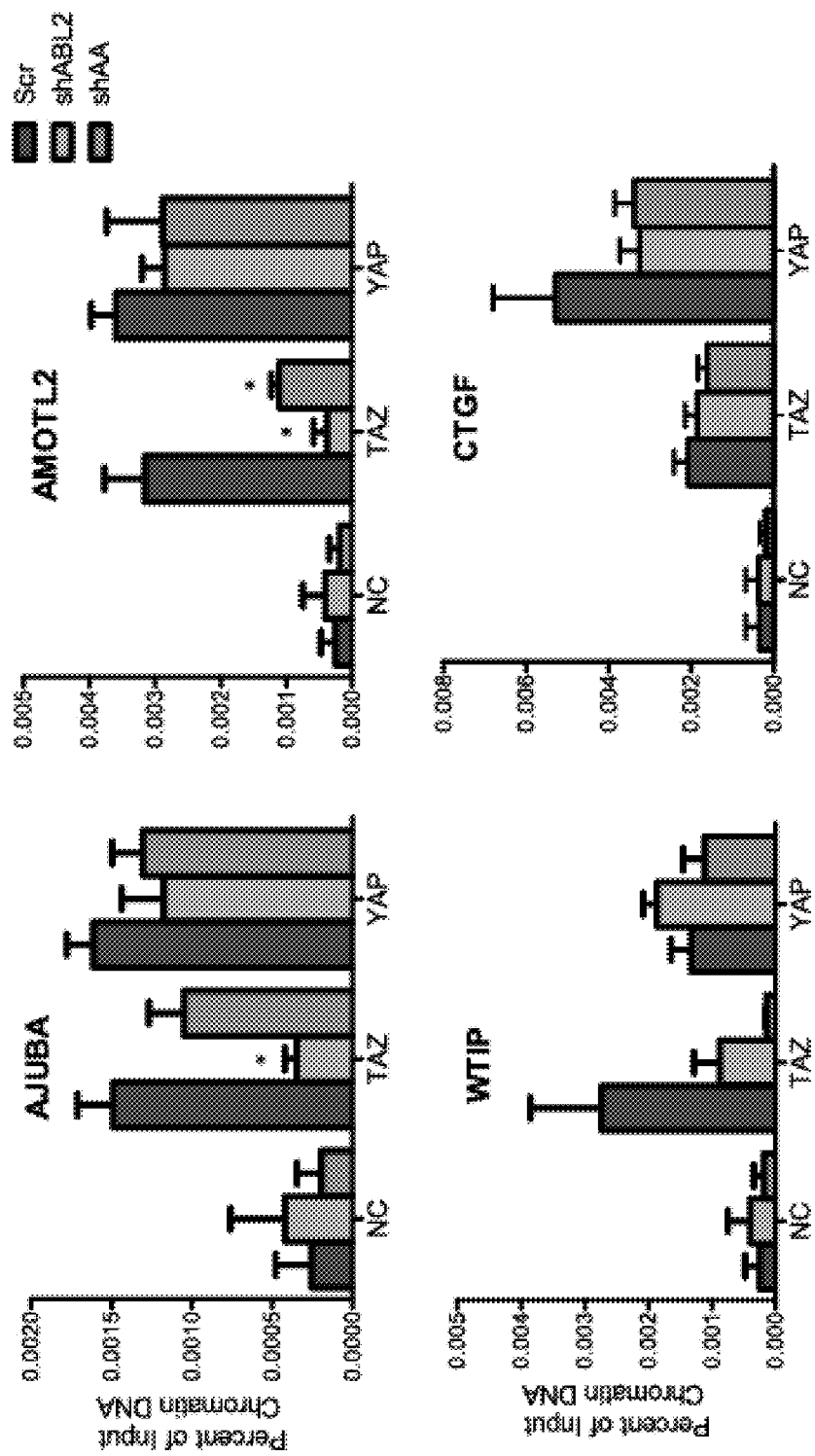

FIG. 23 demonstrates that depletion of ABL kinases decreases the binding of TAZ to target genes. Breast cancer cells (1833) were transduced with lentiviruses encoding control (Scr), ABL2 single (shABL2), or ABL1/ABL2 double (shAA) knockdown shRNAs, and cultured in 15 cm culture dishes to 90% confluence; $4 \times 10^6$ cells were harvested for each ChIP sample using negative control IgG (NC), anti-TAZ and anti-YAP1 antibody. QPCR was formed with primers for the indicated TAZ and YAP1 targets; y axis corresponds to the percent of total input chromatin DNA. *p<0.05, calculated using One-Way ANOVA followed by Tukey's HSD. N=3 biological replicates.

Figure 24:
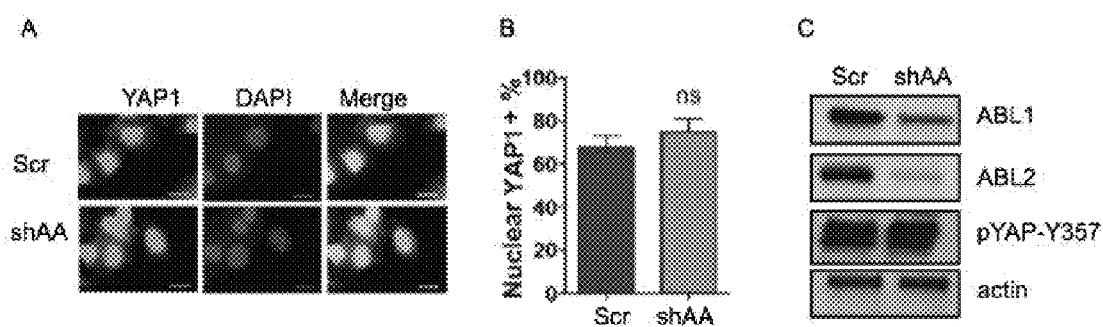

FIG. 24 demonstrates that depletion of ABL kinases does not affect YAP1 protein abundance, localization, or tyrosine phosphorylation in breast cancer cells. (A) Control and ABL1/ABL2 double knockdown (shAA) 1833 cells were analyzed for YAP1 protein abundance and subcellular localization by immunofluorescence staining for endogenous YAP1 (green); DAPI (blue) was used to stain cell nuclei. Scale bar=20 µM. (B) Quantification of the percentage of nuclear YAP1-positive cells in (A). n=3 biological replicates. (C) Immunoblotting with the indicated antibodies was performed on whole cell lysates from control and ABL1/ABL2 knockdown cells. n=2 blots.

Figure 25:
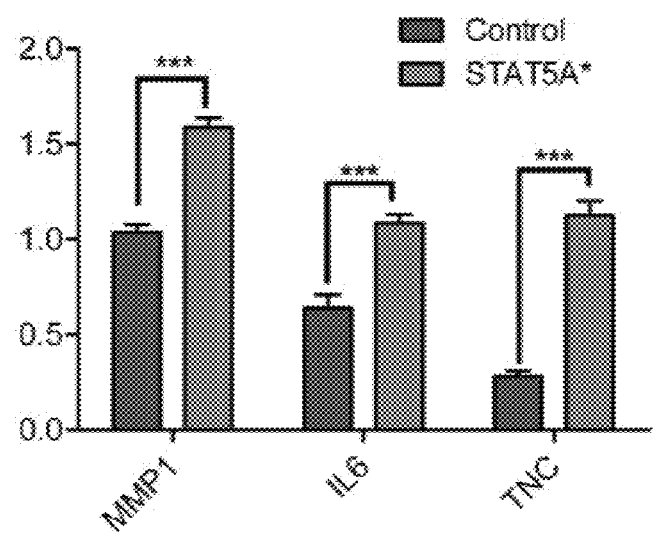

FIG. 25 demonstrates that expression of a constitutively active STAT5 mutant increases mRNA expression of MMPI, IL6, and TNC. The mRNA expression of the indicated genes was detected using RT-PCR of control cells and cells transfected with constitutively active STAT5A*; *p<0.05; p<0.01; *p<0.001. N=3 biological replicates.

Figure 26:
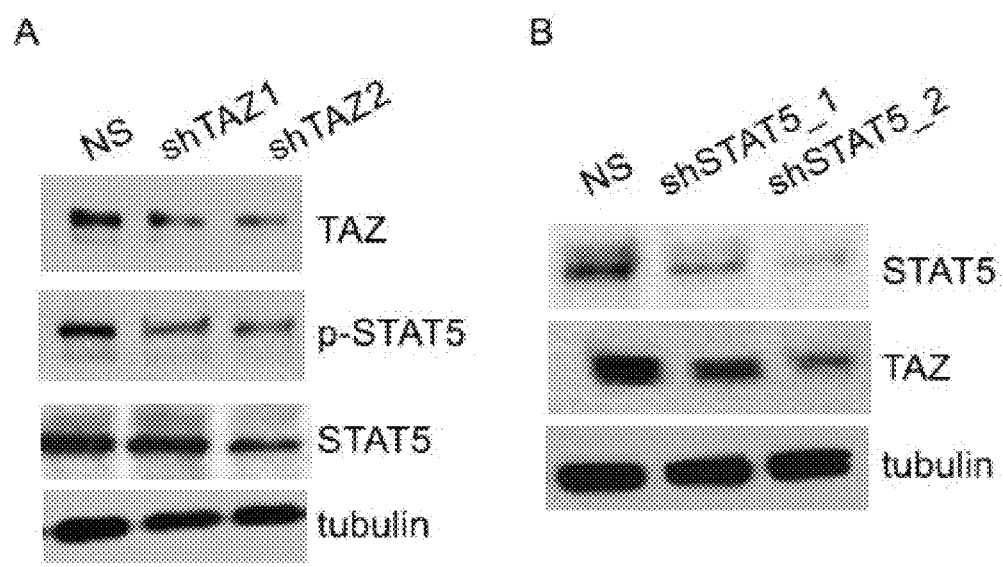

FIG. 26 shows the potential interdependence of TAZ and STAT5 in breast cancer cells. (A) 1833 cells were transduced with lentiviruses encoding vector control (NS) or two different shRNAs against TAZ (shTAZ1, shTAZ2). Immunoblots were performed on whole cell lysates with the indicated antibodies. n=2 blots. (B) 1833 cells were transduced with retroviruses encoding control (NS) or two different shRNAs against STAT5 (shSTAT5_1, shSTAT5_2). Immunoblots were performed on whole cell lysates with the indicated antibodies. n=2 blots.

DETAILED DESCRIPTION OF THE INVENTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control. Unless otherwise defined, all technical terms used herein have the same meaning as commonly understood by one of ordinary skill in the art to which this disclosure belongs.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The term "ABL1 and/or ABL2 kinase inhibitor" refers to any compound or composition that is capable of inhibiting the expression and or function of the ABL1 and/or ABL2 kinase or is capable of disrupting or inhibiting the ABL1 and/or ABL2 kinase pathway. Examples include, but are not limited to, imatinib, nilotinib, ABL001 and combinations thereof.

The term "inhibitor," as used herein, refers to a molecule, which diminishes, inhibits, or prevents the action of another molecule or the activity of an enzyme.

Type I inhibitors are ATP-competitive compounds that bind to the ATP binding site and hydrogen bond with the hinge region of the kinase. Competitive inhibitors reversibly bind at the ATP site, but without activating the kinase.

Type II inhibitors are compounds which bind partially in the ATP binding site and extend past the gatekeeper and into an adjacent allosteric site that is present only in the inactive kinase conformation.

"Allosteric inhibitors" do not compete with ATP for binding. Allosteric inhibitors bind to a distinctly separate binding site from ATP on the kinase, exerting their action to that kinase via the other binding site. For example, compounds GNF2 and GNF5 bind to the myristoyl-binding pocket in the C-lobe of the ABL kinase domain. The bound inhibitor may result in a decreased affinity of ATP, or alternatively may prevent conformational changes in the kinase required for activation after the ATP binds.

As is known in the art, a "cancer" is generally considered as uncontrolled cell growth. The methods disclosed herein can be used to treat any cancer, and any metastases thereof, including, but not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma and peripheral neuroepithelioma. In certain embodiments, the cancer comprises breast cancer. In other certain embodiments, the cancer comprises lung cancer.

The term "disease" as used herein includes, but is not limited to, any abnormal condition and/or disorder of a structure or a function that affects a part of an organism. It may be caused by an external factor, such as an infectious disease, or by internal dysfunctions, such as cancer, autoimmune diseases and the like.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient that is suffering from cancer (e.g., breast or lung cancer).

As used herein, "treatment" or "treating" refers to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

Accordingly, in one aspect the invention relates to a method of treating cancer in a subject suffering from cancer, comprising inhibiting ABL kinase activity by administering an ABL-specific inhibitor, provided that no non-specific ABL inhibitor is administered to the subject.

In one embodiment, the ABL-specific inhibitor is an allosteric inhibitor. In one embodiment, the allosteric inhibitor binds to ABL1 and/or ABL2 kinases at the myristoyl binding site. In one embodiment, the allosteric inhibitor of ABL1 and ABL2 kinases is GNF5 or ABL001.

In one embodiment, the non-specific ABL inhibitor is an ATP-competitive inhibitor. In one embodiment, the non-specific ABL inhibitor is imatinib, dasatinib, or nilotinib.

In one embodiment, the cancer is characterized by solid tumors. In one embodiment, the cancer is breast cancer. In one embodiment, the breast cancer is HER2-positive or basal-like.

In another aspect, the invention relates to a method of treating breast cancer in a subject suffering from breast cancer, comprising inhibiting ABL kinase activity by administering an ABL-specific inhibitor.

In one embodiment, the ABL-specific inhibitor is an allosteric inhibitor. In one embodiment, the allosteric inhibitor binds to ABL1 and/or ABL2 kinases at the myristate binding site. In one embodiment, the allosteric inhibitor is GNF5 or ABL001.

In another aspect, the invention relates to a method of reducing bone metastasis associated with cancer in a subject suffering from cancer, comprising administering an ABL-specific inhibitor.

In one embodiment, the ABL-specific inhibitor is an allosteric inhibitor. In one embodiment, the allosteric inhibitor binds to ABL1 and/or ABL2 kinases at the myristate binding site. In one embodiment, the allosteric inhibitor is GNF5 or ABL001.

In one embodiment, the cancer is breast cancer. In one embodiment, the breast cancer is HER2-positive or basal-like.

In another aspect, the invention relates to a method of reducing tumor-induced osteolysis associated with breast cancer in a subject suffering from breast cancer, comprising administering an ABL-specific inhibitor.

In one embodiment, the ABL-specific inhibitor is an allosteric inhibitor. In one embodiment, the allosteric inhibitor binds to ABL1 and/or ABL2 kinases at the myristoyl binding site. In one embodiment, the allosteric inhibitor is GNF5 or ABL001.

In one embodiment, no non-specific ABL inhibitor is administered. In one embodiment, the non-specific ABL inhibitor is a ATP-competitive inhibitor. In one embodiment, the ATP-competitive inhibitor is imatinib, dasatinib, or nilotinib.

In another aspect, the invention relates to a method of determining whether a subject suffering from breast cancer is likely to develop related bone metastasis, comprising: determining expression levels of at least one gene selected from the group consisting of ABL2, TAZ, AXL, STAT5A, STAT5B, TNC, MMP1, CTGF, and IL6 in a biological sample, wherein a level of expression of the at least one gene at least 3-fold greater than normal tissue indicates that the subject has an increased risk of developing breast cancer-related bone metastasis.

In one embodiment, expression levels of at least four genes selected from the group consisting of ABL2, TAZ, AXL, STAT5A, STAT5B, TNC, MMP1, CTGF, and IL6 are determined.

In one embodiment, the at least one gene is selected from the group consisting of ABL2, TAZ, AXL, STAT5A, and TNC. In one embodiment, the at least one gene comprises ABL2, TAZ, and AXL.

In one embodiment, the expression levels are determined by rtPCR.

In another aspect, the invention relates to a method of treating breast cancer in a subject suffering from breast cancer, comprising: ordering a test which determines expression levels of at least one gene selected from the group consisting of ABL2, TAZ, AXL, STAT5A, STAT5B, TNC, MMP1, CTGF, and IL6 in a biological sample; selecting subjects having a level of expression of the at least one gene at least 3-fold greater than normal tissue; and, administering an ABL-specific inhibitor to the selected subjects.

In one embodiment, expression levels of at least four genes selected from the group consisting of ABL2, TAZ, AXL, STAT5A, STAT5B, TNC, MMP1, CTGF, and IL6 are determined.

In one embodiment, the at least one gene is selected from the group consisting of ABL2, TAZ, AXL, STAT5A, and TNC.

In one embodiment, the at least one gene comprises ABL2, TAZ, and AXL.

In one embodiment, the ABL-specific inhibitor is an allosteric inhibitor. In one embodiment, the allosteric inhibitor binds to ABL1 and/or ABL2 kinases at the myristoyl binding site. In one embodiment, the allosteric inhibitor is GNF5 or ABL001.

In one embodiment, no non-specific ABL inhibitor is administered. In one embodiment, the non-specific ABL inhibitor is a ATP-competitive inhibitor. In one embodiment, the ATP-competitive inhibitor is imatinib, dasatinib, or nilotinib.

In another aspect, the invention relates to a method of reducing bone metastasis associated with cancer in a subject suffering from cancer, comprising: ordering a test which determines expression levels of at least one gene selected from the group consisting of ABL2, TAZ, AXL, STAT5A, STAT5B, TNC, MMP1, CTGF, and IL6 in a biological sample; selecting subjects having a level of expression of the at least one gene at least 3-fold greater than normal tissue; and, administering an ABL-specific inhibitor to the subjects.

In one embodiment, expression levels of at least four genes selected from the group consisting of ABL2, TAZ, AXL, STAT5A, STAT5B, TNC, MMP1, CTGF, and IL6 are determined.

In one embodiment, the at least one gene is selected from the group consisting of ABL2, TAZ, AXL, STAT5A, and TNC. In one embodiment, the at least one gene comprises ABL2, TAZ, and AXL.

In one embodiment, the ABL-specific inhibitor is an allosteric inhibitor. In one embodiment, the allosteric inhibitor binds to ABL1 and/or ABL2 kinases at the myristoyl binding site. In one embodiment, the allosteric inhibitor is GNF5 or ABL001.

In one embodiment, the cancer is breast cancer. In one embodiment, the breast cancer is HER2-positive or basal-like.

EXAMPLES

General Experimental
Materials and Methods
Cell Culture:

The human breast carcinoma cell line MDA-MB-231 was purchased from the American Type Culture Collection (ATCC). The 1833 (bone metastasis), 4175 (lung metastasis), and BrM2a (brain metastasis) sublines were derived from the parental cell line MDA-MB-231 (Kang et al., *Cancer Cell*, 2003) and were gifts from J. Massague (Memorial Sloan-Kettering Cancer Center). The SCP28 (bone metastasis) subline was provided by Y. Kang (Princeton University). MDA-MB-231, their derivative sublines, and genetically modified versions were maintained in Dulbecco's modified Eagle's medium (DMEM; Life Technologies) supplemented with 10% fetal bovine serum (FBS; Life Technologies), antibiotics, and appropriate selection drugs for transfected plasmids. Human embryonic kidney (HEK) 293T cells, a packaging cell line for lentivirus production, and the preosteoclast cell line RAW264.7 (ATCC) were maintained in DMEM supplemented with 10% FBS and antibiotics. The murine osteoblast cell line 7F2 (ATCC) was cultured in a-MEM with 10% FBS. The human mammary epithelial cell line (HuMEC) was maintained in human basal serum-free medium (Life Technologies) with the HuMEC kit (Life Technologies). The human breast cancer cell line SKBR3 was purchased from the Duke University Cell Culture Facility and was maintained in McCoy's 5A medium (Life Technologies) supplemented with 10% FBS (Life Technologies) and antibiotics. All cultures were maintained at 37° C. in humidified air containing 5% CO2.

Antibodies:

Antibodies used for Western blotting included cleaved caspase-3, phosphorylated CrkL (Y207), phosphorylated Akt (Ser473), Akt, TAZ, YAP1, phosphorylated STAT5 (Tyr694), STAT5, and ERBB2 from Cell Signaling; b-tubulin and actin from Sigma-Aldrich; ABL2 (9H5) from Santa Cruz Biotechnology; ABL1 (8E9) from BD Biosciences; IL-6, TNC, and phosphorylated YAP1 (Tyr357) from Abcam; and MMP1 from Calbiochem. Antibodies used for immunofluorescence staining included YAP1 from Cell Signaling and TAZ from BD Biosciences. Antibodies used for the ChIP assays were TAZ (V386) and YAP1 (D8H1X) from Cell Signaling.

Tumor Xenografts and Analysis:

Procedures involving mice were approved and performed following the guidelines of the Institutional Animal Care and Use Committee (IACUC) of Duke University Division of Laboratory Animal Resources (DLAR). Age-matched female athymic NCr nu/nu mice (5 to 6 weeks old) were used for xenograft experiments. For intra-cardiac injections, cells were harvested from sub-confluent culture plates, washed with phosphate-buffered saline (PBS), and resuspended at 106/ml (1833) or 5×106/ml (SCP28) in PBS; 0.1 ml of the suspended cells was injected into the left cardiac ventricle using 30-gauge needles. Mice were anesthetized with isoflurane before injection and imaged by bioluminescence imaging. For intra-tibial injections, mice were anesthetized using a mixture of ketamine (100 mg/kg) and xylazine (10 mg/kg). The injection site was cleaned with a 70% alcohol wipe. Single-cell suspensions (1×105 cells) in a final volume of 10 ml were injected into the upper half of the tibia medullary cavity, as felt by a lack of resistance when pushing cells into the cavity. Bioluminescence imaging was used to confirm successful cancer cell inoculation and progression of metastatic bone lesions. The allosteric inhibitor GNF5 was synthesized by the Duke University Small Molecule Synthesis Facility. For drug treatment, the mice were dosed daily with GNF5 in DMSO/peanut oil (1:9) at 50 mg/kg by intraperitoneal injection.

Bone μCT Analysis:

Hind limb bones were excised, fixed in 10% neutral-buffered formalin, and imaged using a μCT scanner (SkyScan 1176, Bruker Corp.) at 17-mm resolution and 180° scanning with a rotation step of 0.7° per image, 242-ms exposure time, 55-kV photon energy, and 455-mA current. The images were reconstructed using NReconServer, and bone volume was analyzed by CT analysis software (CTAn, Bruker Corp.).

In Vitro Osteoclastogenesis Assay:

Bone marrow cells were flushed out from the femora and tibia of 6-week-old C57BL/6 mice and plated in basal culture medium (a-MEM supplemented with 10% FBS and antibiotics) overnight. Osteoclastogenesis assay and TRAP staining were conducted as described previously (Lu et al., Genes Dev., 2009). Tumor cells were plated at 2×10$^5$ per well in 12-well plates to obtain conditioned medium for incubation with either bone marrow cells or RAW264.7 cells. RAW264.7 pre-osteoclasts were plated at 4×10$^5$ per well in 24-well plates overnight. RAW264.7 medium was replaced by conditioned medium harvested from tumor cells and supplemented with recombinant murine sRANKL (50 ng/ml). The medium was changed every 3 days, and TRAP staining was performed on day 6 following the manufacturer's instructions (Sigma).

RNAseq Analysis:

For RNAseq analysis, 3×10$^6$ breast cancer cells were plated in a 10-cm petri dish in triplicate in complete medium for 24 hours. Cells were harvested, and RNA was isolated using the RNeasy kit (Qiagen); 1 mg of total RNA input was used for each sample. The libraries were sequenced on an Illumina HiSeq 2000 sequencing system using 50-base pair single-ended reads. RNAseq data were mapped to reference genome (HG19) using Bowtie/TopHat. The reads were counted, and the differential expression between distinct experimental groups was quantified using Cuffdiff. Significant genes were extracted using R CummeRbund.

Viral Transduction:

HEK293T cells were transfected with the following retroviral or lentiviral constructs, with their packaging vectors indicated, using FuGENE 6 reagent (Promega): pMX-puro-STAT5A* (provided by T. Kitamura, University of Tokyo; pCMV-Gag-Pol and pCMV-VSV-G); pLenti-EF-FH-TAZS89A (psPAX2 and pVSV-G); PLKO-NS and shTAZ lentiviral construct (provided by C. Linardic, Duke University; pCMV-Rev, pCVM-VSVG; pMDL). Retroviral or lentiviral supernatants were collected and filtered 24 and 48 hours after transfection. 1833 cells were incubated 48 hours with retroviral or lentiviral medium in the presence of Polybrene (8 mg/ml). Cells were cultured at least 3 days in puromycin (3 mg/ml) or blasticidin (5 mg/ml) for selection. Lentiviral shRNA-mediated knockdown of ABL1/ABL2 and expression of mouse ABL1/ABL2 were conducted as described previously (Chislock et al., Proc. Natl. Acad. Sci., 2013; Smith-Pearson et al., J. Biol. Chem., 2010; Chislock et al., PLOS One, 2013). Lentiviral shRNA-mediated knockdown of STAT5A and STAT5B was conducted following the manufacturer's instructions (Dharmacon RHS4531-EG6776, EG6777).

Immunoblotting:

Cells were lysed in radio-immunoprecipitation assay buffer with protease and phosphatase inhibitors. Cell debris was removed by microcentrifugation, and protein was quantified. Alternatively, equal cell numbers were plated onto six-well plates, and 24 hours later, conditioned medium was harvested and concentrated using Amicon Ultra Centrifugal Filters (Millipore). Equal amounts of protein or conditioned medium were separated by SDS-polyacrylamide gel electrophoresis and transferred onto nitrocellulose membranes and probed with the indicated antibodies.

Real-Time RT-PCT:

RNA was isolated from cancer cells using the RNeasy RNA isolation kit (Qiagen), and complementary DNA was synthesized using oligo(dT) primers and Moloney murine leukemia virus reverse transcriptase (Invitrogen). Real-time PCR was performed using iQ SYBR Green Supermix (Bio-Rad). The primers used were as follows: mouse RANKL, 5'-TTGCACACCTCACCATCA (forward; SEQ ID NO: 1) and 5'-TACGCTTCCCGATGTTTC (reverse; SEQ ID NO: 2); mouse OPG, 5'-CACTCGAACCTCACCACA (forward; SEQ ID NO: 3) and 5'-CAAGTGCTTGAGGGCATA (reverse; SEQ ID NO: 4); mouse GAPDH, 5'-CTCATGAC-CACAGTCCATGC (forward; SEQ ID NO: 5) and 5'-ACA-CATTGGGGGTAGGAACA (reverse; SEQ ID NO: 6); human ABL1, 5'-GGCTGTGAGTACCTTGCTGC (forward; SEQ ID NO: 7) and 5'-GGCGCTCATCTTCATTCA-GGC (reverse; SEQ ID NO: 8); human ABL2, 5'-CCAGC-TACTCCCGAGGCTG (forward; SEQ ID NO: 9) and 5'-CTTGATCCCACAGGGTGAAG (reverse; SEQ ID NO:10); human GAPDH, 5'-GGCTCTCCAGAACAT-CATCCC (forward; SEQ ID NO: 11) and 5'-GGGT-GTCGCTGTTGAAGTCAG (reverse; SEQ ID NO: 12); human MMP1, 5'-GGTCTCTGAGGGTCAAGCAG (forward; SEQ ID NO: 13) and 5'-AGTTCATGAGCAACACG (reverse; SEQ ID NO: 14); human IL6, 5'-AGACAGC-CACTCACCTCTTC (forward; SEQ ID NO: 15) and 5'-TTTCACCAGGCAAGTCTCCT (reverse; SEQ ID NO: 16); human TNC, 5'-CCCTACGGGTTCACAGTTTC (forward; SEQ ID NO: 17) and 5'-TTCCGGTTCGGCTTCTG-TAAC (reverse; SEQ ID NO: 18); human AXL, 5'-ATCA-GACCTTCGTGTCCCAG (forward; SEQ ID NO: 19) and 5'-ATGTCTTGTTCAGCCCTGGA (reverse; SEQ ID NO: 20); human WWTR1, 5'-GGCTGGGAGATGACCTTCAC (forward; SEQ ID NO: 21) and 5'-AGGCACTGGTGTG-GAACTGAC (reverse; SEQ ID NO: 22); human YAP1, 5'-ATGAACTCGGCTTCAGCCAT (forward; SEQ ID NO: 23) and 5'-ACCATCCTGCTCCAGTGTTG (reverse; SEQ ID NO: 24). Analysis was performed using a Bio-Rad CFX384 real-time machine and CFX Manager software. PCR assays were performed in triplicate. The expression of each gene was normalized to that of the GAPDH gene.

Histological Analysis:

Hind limb bones were excised, fixed in 10% neutral-buffered formalin, decalcified, and embedded in paraffin for H&E staining (Zhang et al., *Cancer Cell*, 2009).

TUNEL Staining:

For TUNEL staining, $2 \times 10^4$ cells were seeded onto each single chamber of a four-chamber slide in complete medium. The next day, the medium was replaced with serum-free medium containing TRAIL (2 ng/ml). After 3 days, cells were fixed with 4% paraformaldehyde and permeabilized with 0.1% Triton X-100. TUNEL staining was performed following the manufacturer's protocol (Roche Applied Science).

ELISA and Cytokine Array:

Conditioned medium was collected, after 24 hours of incubation, from confluent cells and was applied to the Human Cytokine Antibody Array C1000 (RayBiotech) or the IL-6 ELISA kit (R&D) following the manufacturer's instructions.

Invasion Assay:

Invasion was evaluated by plating 25,000 cells in the upper chambers of matrigel chambers (8.0-mm pore size; BD Biosciences) in serum-free medium. Cells were allowed to invade for up to 48 hours in the presence of serum-containing medium in the bottom chamber. Afterward, the remaining cells, medium, and matrigel were removed from the upper chambers, and cells on the undersurface of the membrane were fixed, stained with DiffQuik (Dade Behring), and quantified by microscopy.

In Vitro Cell Growth Assays:

For 2D cell growth, 3000 cells were seeded onto each well of a 96-well plate. Cell growth was measured daily from days 1 to 5 using Cell Titer-Glo (Promega) following the manufacturer's protocol. For 3D cell growth, 75 ml of matrigel (BD Bioscience) was plated onto each well of a 96-well plate. A single-cell suspension (50 ml) containing 1500 cells was mixed with matrigel (1:1) and plated on top of the matrigel base onto wells of a 96-well plate; 50 ml of complete medium was added, and the cells were cultured for 14 days. Colonies were analyzed and counted using a microscope.

ChIP-qPCR Analysis:

CHIP-quantitative real-time fluorescence PCR (qPCR) was performed using Cell Signaling SimpleChIP Plus Enzymatic Chromatin IP Kit (#9005) according to the manufacturer's instructions. SimpleChIP human CTGF promoter primers were from Cell Signaling (#14927). Validated TAZ/YAP primers, as well as previously validated primers for AJUBA, AMOTL2, and WTIP were used for the qPCR analysis (F. Zanconato et al., *Nat. Cell Biol.*, 2015). Antibodies used for ChIP assays were anti-TAZ (V386) and anti-YAP1 (D8H1X) from Cell Signaling. The primers used were as follows: AXL forward, 5'-CAGCCTCCTCCT-CACAGACA (SEQ ID NO: 25); AXL reverse, 5'-GAGC-CCTGATCATTCCACTG (SEQ ID NO: 26); AJUBA forward, 5'-AAGGAAAGAGTGTGGGGGTAGG (SEQ ID NO: 27); AJUBA reverse, 5'-ACGCTGGGAACAAAGT-CACG (SEQ ID NO: 28); AMOTL2 forward, 5'-TGCCA-GGAATGTGAGAGTTTC (SEQ ID NO: 29); AMOTL2 reverse, 5'-AGGAGGGAGCGGGAGAAG (SEQ ID NO: 30); WTIP forward, 5'-GCAGCGCCGTCTCCTTCCT (SEQ ID NO: 31); WTIP reverse, 5'-GCGGCGGAGGAAT-GTAAGCTC (SEQ ID NO: 32).

Mutagenesis:

ABL2 E505K mutagenesis was conducted on pBabe-puro-mABL2 construct using the Q5 Site-Directed Mutagenesis Kit (NEB, E0554S) according to the manufacturer's instructions. The primers used were as follows: ABL2 forward, 5'-CATCTCTGAAAAGGTAGCTCAG (SEQ ID NO: 33); ABL2 reverse, 5'-CTGGAGTCATGGAACATTG (SEQ ID NO: 34).

Statistical Analysis:

Statistical analyses were performed using GraphPad Prism 6, JMP Pro, and R 3.2. Comparisons of two groups were performed using Student's t tests (two-tailed). Comparisons involving multiple groups were evaluated using one-way or two-way ANOVA, followed by Tukey's post hoc test. For all tests, $p<0.05$ was considered statistically significant. For all figures, the p value was calculated using Student's t test unless otherwise indicated. Data shown represent averages±SEM unless otherwise indicated.

EXAMPLES

Figure 1:
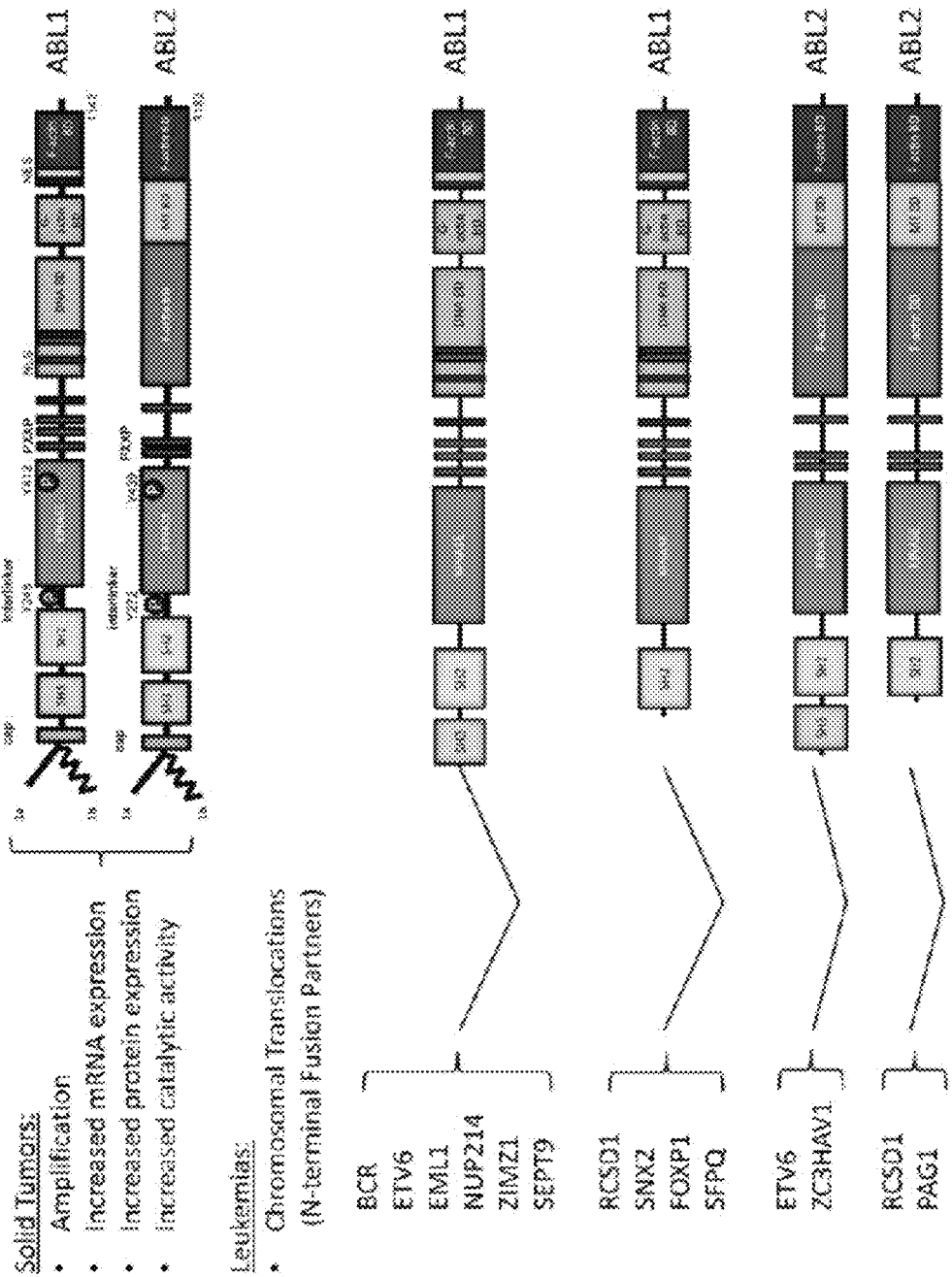
FIG. 1 illustrates mechanisms for activation of ABL family kinases in leukemia and solid tumors, affording schematic representation of ABL1, ABL2, and the various ABL1 and ABL2 fusion proteins that arise as a consequence of chromosome translocations in leukemias. In solid tumors, ABL kinases are upregulated through various mechanisms including amplification, increased mRNA expression, enhanced protein expression, and/or hyper-activation of catalytic activity. In leukemia, ABL kinases are activated mainly through chromosomal transaction events. Various N terminal fusion partners generate chimeric proteins that retain both the SH3 and SH2 domains, or only the SH2 domain, of ABL1 and ABL2 as indicated. The distinct partner sequences fused to the N terminus of the ABL kinases promote enhanced kinase and transforming activities by disrupting inhibitory intramolecular interactions, providing sequences that facilitate oligomerization, enhancing tyrosine phosphorylation and/or by recruiting the chimeric kinases to distinct subcellular sites and protein complexes.
Figure 2:
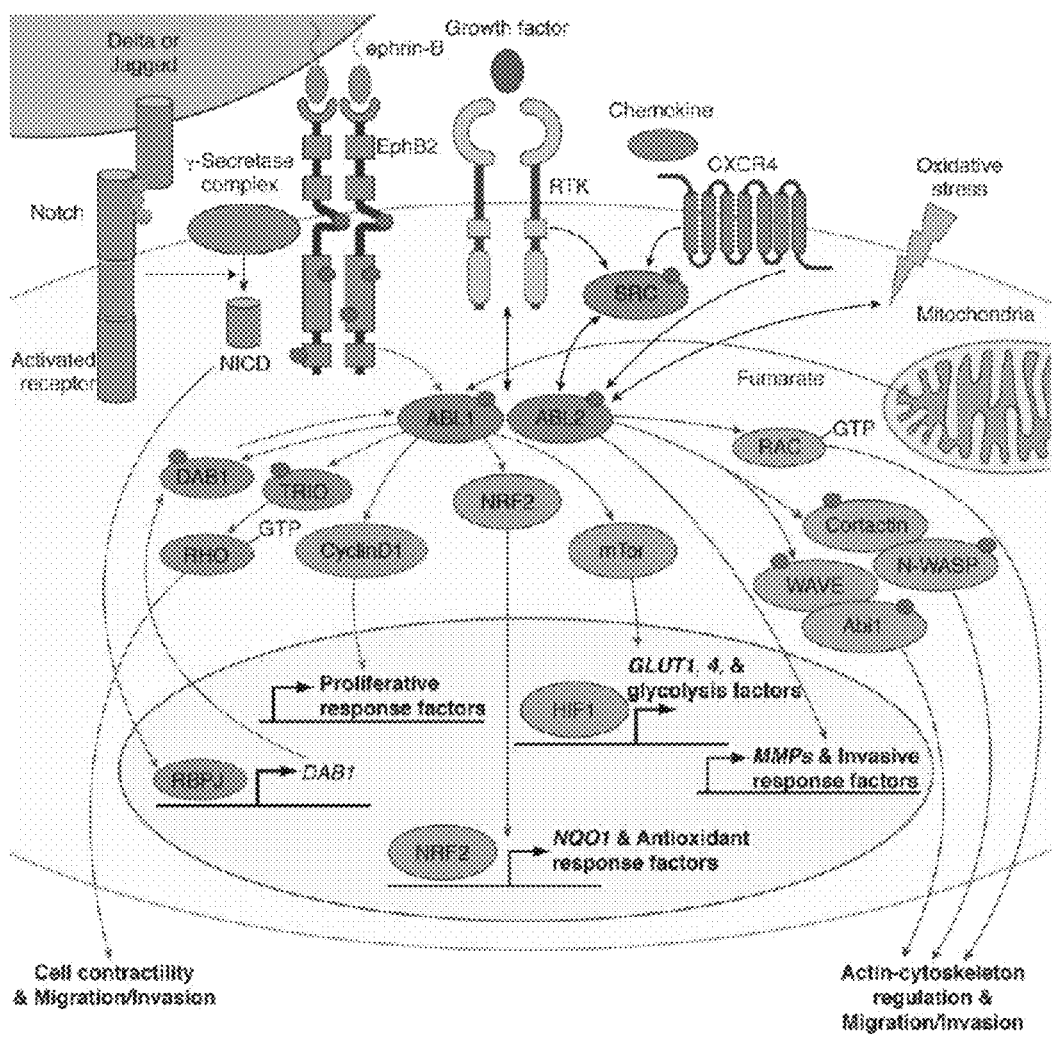
FIG. 2 shows the pathway for kinase activation and signaling of ABL kinases in solid tumors. ABL kinases are activated downstream of hyperactive receptor tyrosine kinases (RTKs), chemokine receptors and SRC family kinases, or in response to oxidative and metabolic stress pathways. The activated ABL kinases promote cancer cell migration and invasion by activating multiple MMPs and actin-regulatory proteins such as Rac, cortactin, N-WASP, ABL interactor 1 (ABI1) and WAVE (Mader et al., *Cancer Res.*, 2011; Gu et al., *Sci. Signal.*, 2012; Sun et al., *Carcinogenesis*, 2009; Srinivasan et al., *Cancer Res.*, 2006) (orange pathways). ABL1 functions downstream of the EphB2 receptor to regulate CyclinD1 signaling to promote activation of proliferative response factors in intestinal epithelium and adenomas (Genander et al., *Cell*, 2009; Kundu et al., *Science Trans. Med.*, 2015) (blue pathway). The ABL1 kinase is hyperactive in FH-deficient renal cancer cells (HLRCC) in response to high fumarate levels; the activated ABL1 promotes aerobic glycolysis through activation of the mTOR-HIF1α pathway and also induces nuclear localization of the transcription factor NRF2 to induce expression of NQO1 and other antioxidant response factors in HLRCC (Yang et al., *PLoS One*, 2013) (purple pathway). Activation of Notch in the intestinal epithelium of $Apc^{+/\Delta 716}$ polyposis mice promoted RBPJ-mediated transcription leading to increased levels of DAB1, a substrate and activator of the ABL kinases; the activated ABL in colorectal cancer cells induced tyrosine phosphorylation of TRIO on Y2681, leading to enhanced TRIO Rho-GEF activity (Sonoshita et al., *Cancer Discov.*, 2015) (green pathway).
Figure 3:
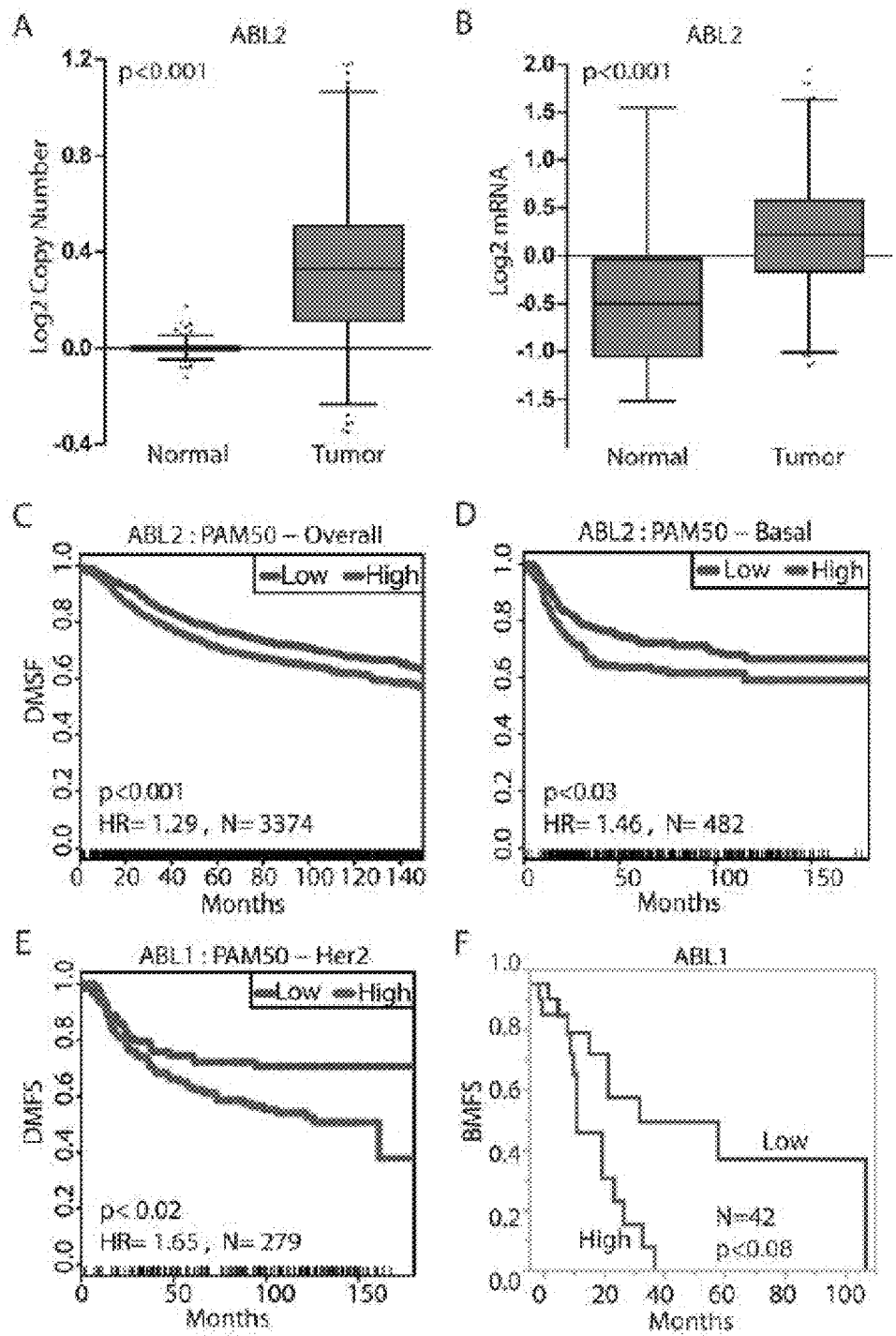
FIG. 3 demonstrates that increased expression of ABL genes in invasive breast cancer is associated with metastasis. (A) ABL2 copy number in 813 normal samples compared with 789 invasive breast tumor samples in the TOGA database. (B) ABL2 mRNA abundance in 61 normal samples compared with 532 invasive breast tumor samples in the TOGA database. Results shown in (A) and (B) are based on the data generated by the TOGA Research Network (http://cancergenome.nih.gov); whiskers represent 1st and 99th percentile. (C and D) Kaplan-Meier representation of the probability of cumulative overall distant metastasis-free survival (DMFS) in 2830 breast cancer cases (C) or 482 basal breast cancer cases (D) according to ABL2 expression. (E) Kaplan-Meier representation of the probability of cumulative overall distant metastasis-free survival in 279 HER2-enriched breast cancer cases according to ABL1 expression. (F) Kaplan-Meier representation of the probability of cumulative bone metastasis-free survival (BMFS) in 42 breast cancer cases according to ABL1 expression. P values (log-rank test) and hazard ratios (HR) are shown in the graph.

Example 1: Increased Expression of ABL Kinase-Encoding Genes Correlates with Breast Cancer Metastasis To evaluate whether altered expression of the ABL genes is associated with breast cancer progression and metastasis, the expression of ABL1 and ABL2 in normal and invasive breast tumor specimens was examined using published TCGA (The Cancer Genome Atlas) data sets (Cerami et al., *Cancer Discov.*, 2012; Rhodes et al., *Neoplasia*, 2007; *Nature*, 2012). ABL2 DNA and RNA abundance was significantly increased in breast tumor specimens (FIGS. 3, A and B). To further evaluate the importance of enhanced ABL abundance in the context of metastasis, an integrative database assembled from 22 publicly available data sets containing information on metastasis-related relapse (Nelson et al., *Trends Endocrinol. Metab.*, 2014) was analyzed. Increased ABL2 mRNA abundance correlated with metastasis across all subtypes of breast cancer, primarily the basal type (FIGS. 3, C and D), whereas high ABL1 mRNA abundance significantly correlated with metastasis in human epidermal growth factor (EGF) receptor 2 (HER2)-enriched breast cancer but not in other breast cancer subtypes (FIG. 3E). Furthermore, high ABL1 mRNA was associated with bone metastasis in a microarray data set reporting organ-specific metastasis (FIG. 3F) (Bos et al., Nature, 2009). These findings support a link between increased expression of the ABL genes and increased breast cancer metastasis.

Example 2: ABL Family Protein Kinases are Required for Bone Metastasis

To directly evaluate the relationship between ABL family kinases and metastasis, ABL1 and ABL2 protein abundance in MDA-MB-231-derived breast cancer cell lines with different organ metastasis tropisms (Kang et al., Cancer Cell, 2003) was analyzed. The MDA-MB-231-derived 1833 cell line, which is characterized by enhanced bone-specific metastasis compared to the parental cell line or cell lines with increased tropism to lung and brain, showed increased abundance of ABL1 and ABL2 (FIG. 11A). To examine the functional role of ABL kinases in these cells, endogenous ABL kinases were depleted with previously characterized short hairpin RNAs (shRNAs) specific against ABL1 and ABL2 (Chislock et al., Proc. Natl. Acad. Sci. USA, 2013). The lentivirus-encoded shRNAs decreased the abundance of ABL1 and ABL2 by 80% at day 2 after viral transduction, but ABL1 abundance was slightly increased by day 21 after viral transduction (FIG. 11B). Depletion of ABL kinases did not affect cell growth in monolayers or colony formation in matrigel (FIG. 11, C to E) but decreased cell invasion in both 1833 triple-negative and HER2-positive SKBR3 breast cancer cells (FIG. 12, A to D). Conversely, overexpression of constitutively active forms of ABL1 (ABL1PP) and ABL2 (ABL2PP) enhanced the invasiveness of the parental MDA-MB-231 cells (FIG. 12, E to G).

Figure 4:
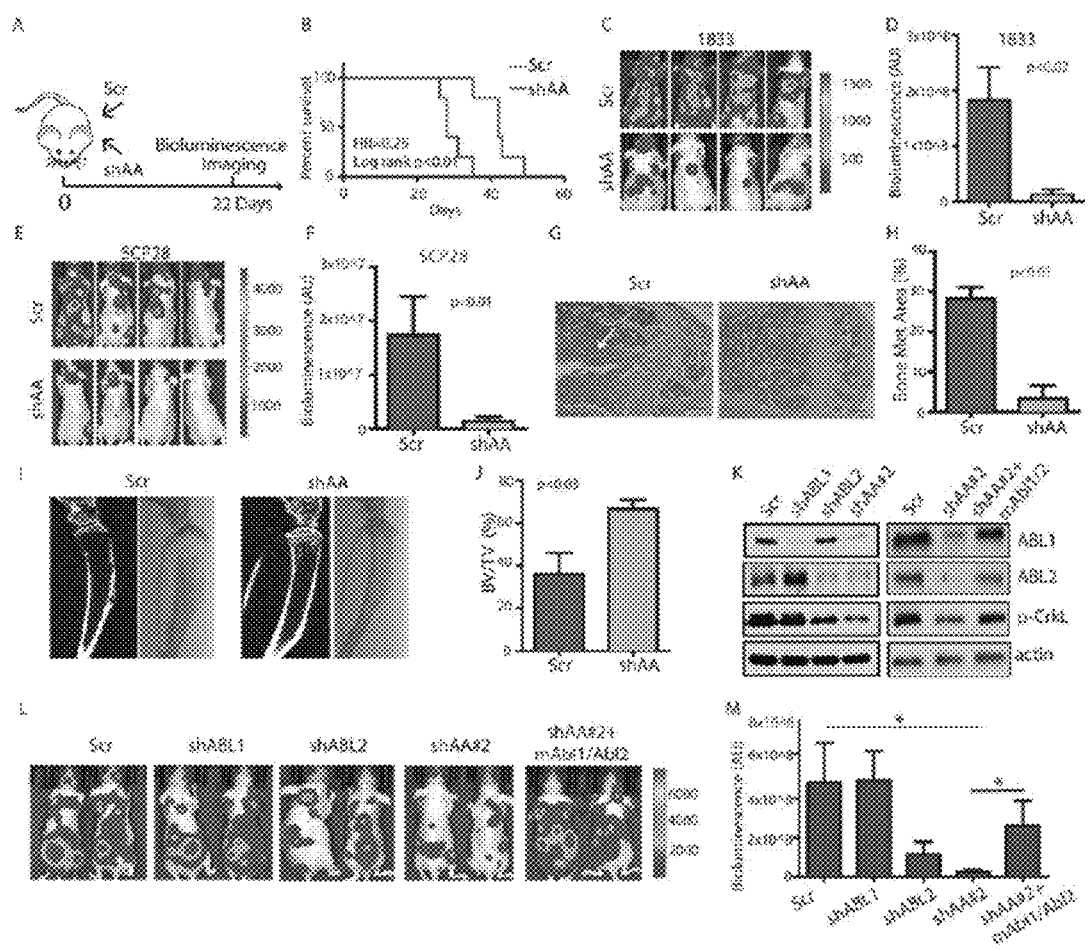
FIG. 4 demonstrates that knockdown of ABL kinases decreases breast cancer bone metastasis. (A) Experimental design. (B) Survival of mice after intra-cardiac injection of 1833 ($1\times10^5$) breast cancer cells transduced with control shRNA (Scr) or shRNAs against ABL1 and ABL2 (shAA); n=10 mice per group. (C to F) Bioluminescent images (C and E) of bone metastasis from representative mice at day 22 after inoculation with 1833 cells (n=10 mice per group) or day 35 after inoculation with SCP28 cells (n=8 mice per group). Quantification of bone metastases (D and F). (G and H) Representative H&E staining (G) and quantification of H&E-stained tumor area of bone lesions. Arrows indicate tumor. n=3 mice per group. Scale bar, 200 µm. Met, metastatic. (I and J) Representative x-ray and µCT reconstruction (I) and quantification of bone volume (BV)/total volume (TV) from µCT analysis of the mouse tibias. (J). n=3 mice per group. (K) Representative immunoblots of 1833 cells transfected with control shRNA, shRNA against ABL1 (shABL1), ABL2 (shABL2), and shRNA#2 against both ABL1 and ABL2 (shAA#2) and ABL1/ABL2 knockdown cells with overexpression of mouse ABL1/ABL2 (shAA+mABL1/Ab12). n=3 blots. p, phosphorylated. (L) Bioluminescent images of bone metastases from representative mice at day 18 after inoculation. n=8 mice per group. (M) Quantification of (L). *P<0.05, one-way analysis of variance (ANOVA) followed by Tukey's post hoc test.

ABL kinases regulate cancer cell invasion (Smith-Pearson et al., J. Biol. Chem., 2010), but it is unclear whether they play a role in the regulation of subsequent steps of the metastatic cascade. To investigate whether inhibition of ABL kinases interferes with metastatic processes other than invasion, ABL1 and ABL2 (ABL1/ABL2) were depleted in two bone metastatic breast cancer cell lines, 1833 and SCP28 (Sethi et al., Cancer Cell, 2011), and the metastatic potential of these cells was evaluated after intra-cardiac injection into immune-deficient mice. This mouse model bypasses the initial invasion step and allows the analysis of subsequent steps in the metastatic cascade. The 1833 and SCP28 breast cancer cells were engineered to express reporters with luciferase and green fluorescent protein to monitor metastatic progression by bioluminescence imaging (FIG. 4A). ABL kinase knockdown increased the survival of tumor-bearing mice (FIG. 4B) and markedly inhibited bone metastases by 1833 and SCP28 breast cancer cells as measured by bioluminescence imaging (FIGS. 4, C to F) and hematoxylin and eosin (H&E) staining (FIGS. 4, G and H). Decreased metastasis by ABL-deficient breast cancer cells was accompanied by a significant reduction in the extent of hind limb osteolytic lesions, as determined by x-ray and micro-computed tomography (μCT) imaging (FIGS. 4, I and J).

Example 3: Role of ABL1 and ABL2 in Promotion of Metastasis

To evaluate whether ABL1 and ABL2 are individually responsible for promoting metastasis, specific shRNA was used to silence either ABL1 or ABL2 in breast cancer cells. An ~90% knockdown of ABL1 alone resulted in enhanced ABL2 expression and did not produce a significant decrease in the phosphorylation of CrkL, a reporter for the activation state of the ABL kinases (FIG. 4K), and did not inhibit metastasis (FIGS. 4, L and M). Double knockdown of ABL1 and ABL2 was required to decrease the phosphorylation of CrkL by more than 90%, which indicates inactivation of the endogenous ABL kinases (FIG. 4K). Whereas knockdown of ABL2 alone decreased metastasis, knockdown of both ABL1 and ABL2 was required to significantly decrease metastasis (FIGS. 4, L and M). To further validate that the decreased metastasis induced by double knockdown of ABL1 and ABL2 was not due to off target effects of the lentivirus-encoded shRNAs, a second set of ABL shRNAs (shAA#2) we used and rescue experiments carried out by expressing mouse ABL1 and ABL2 constructs (mABL1/ABL2) that are resistant to shRNAs against human ABL1 and ABL2. Expression of murine ABL1 and ABL2 kinases in the knockdown cells reversed the decreased metastasis (FIG. 4, K to M). Loss of ABL1 and ABL2 in the lung metastatic 4175 breast cancer cell line did not significantly reduce metastasis (FIG. 13). These findings reveal a function for ABL kinases in the regulation of breast cancer bone metastasis and tumor-induced osteolysis in vivo.

Example 4: Allosteric Inhibition of the ABL Kinases Impairs Breast Cancer Bone Metastasis To date, few studies have directly evaluated the biological consequences of targeting the ABL kinases with selective inhibitors in solid tumors, including breast cancer in vivo. The adenosine triphosphate (ATP)-competitive kinase inhibitors imatinib (STI571; trade name: Gleevec), dasatinib, and nilotinib inhibit multiple tyrosine kinases in addition to ABL1 and ABL2 (Greuber et al., Nat. Rev. Cancer, 2013). Moreover, these ATP-competitive inhibitors induce the formation of B-RAF and C-RAF dimers, leading to extracellular signal-regulated kinase (ERK) activation in diverse cancer cell types (Packer et al., Cancer Cell, 2011). A different approach was therefore employed to evaluate a role for ABL kinases in breast cancer metastasis using the allosteric inhibitor GNF5, which targets the unique ABL myristate-binding site and functions as a non-ATP-site and selective inhibitor of the ABL kinases (Choi et al., J. Biol. Chem., 2009; Zhang et al., Nature, 2010). Notably, GNF5 does not activate the RAF-ERK pathway in breast cancer cells (Packer et al., Cancer Cell, 2011) (FIG. 14).

Figure 5:
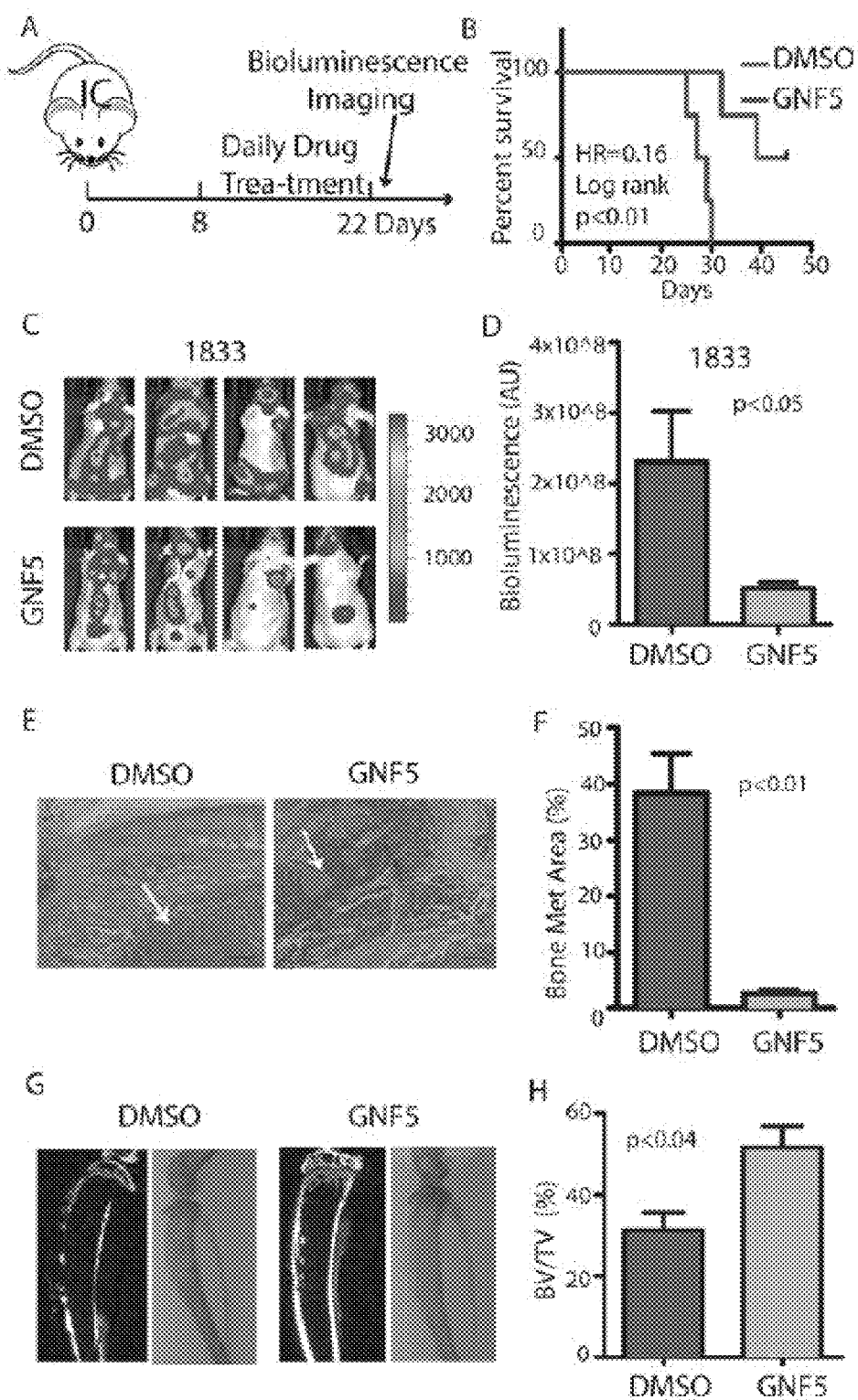
FIG. 5 demonstrates that allosteric inhibition of ABL kinases decreases breast cancer bone metastasis. (A) Experimental design. (B) Survival of mice after intra-cardiac injection of 1833 ($1\times10^5$) breast cancer cells and treatment with either dimethyl sulfoxide (DMSO) control or the allosteric ABL inhibitor GNF5. n=10 mice per group. (C) Bioluminescent images of representative mice at day 22 after inoculation. (D) Quantification of bone metastases. n=10 mice per group. (E and F) Representative H&E staining (E) and quantification (F) of H&E stained tumor area of bone lesions. Arrows indicate tumor. n=3 mice per group. Scale bar, 200 µm. (G and H) Representative x-ray and µCT reconstruction (G) of mouse tibias and quantification (H) of bone volume/total volume. n=3 mice per group.

Treatment of tumor-bearing mice with GNF5 starting on day 8 after intra-cardiac injection of breast cancer cells (FIG. 5A) resulted in a significant increase in survival (FIG. 5B) and a decrease in bone metastasis burden as measured by bioluminescence imaging (FIGS. 5, C and D). Similarly, histological analyses revealed a decrease in bone tumor burden in mice treated with the allosteric inhibitor of the ABL kinases (FIGS. 5, E, and F). Notably, bone destruction was decreased and the ratio of bone volume to total volume was increased in tumor-bearing mice treated with GNF5 (FIGS. 5, G and H). These results demonstrate that ABL kinase activity is required for osteolytic metastasis in breast cancer and suggest that pharmacological inhibition of the ABL kinases may be an effective treatment for bone metastasis.

Figure 6:
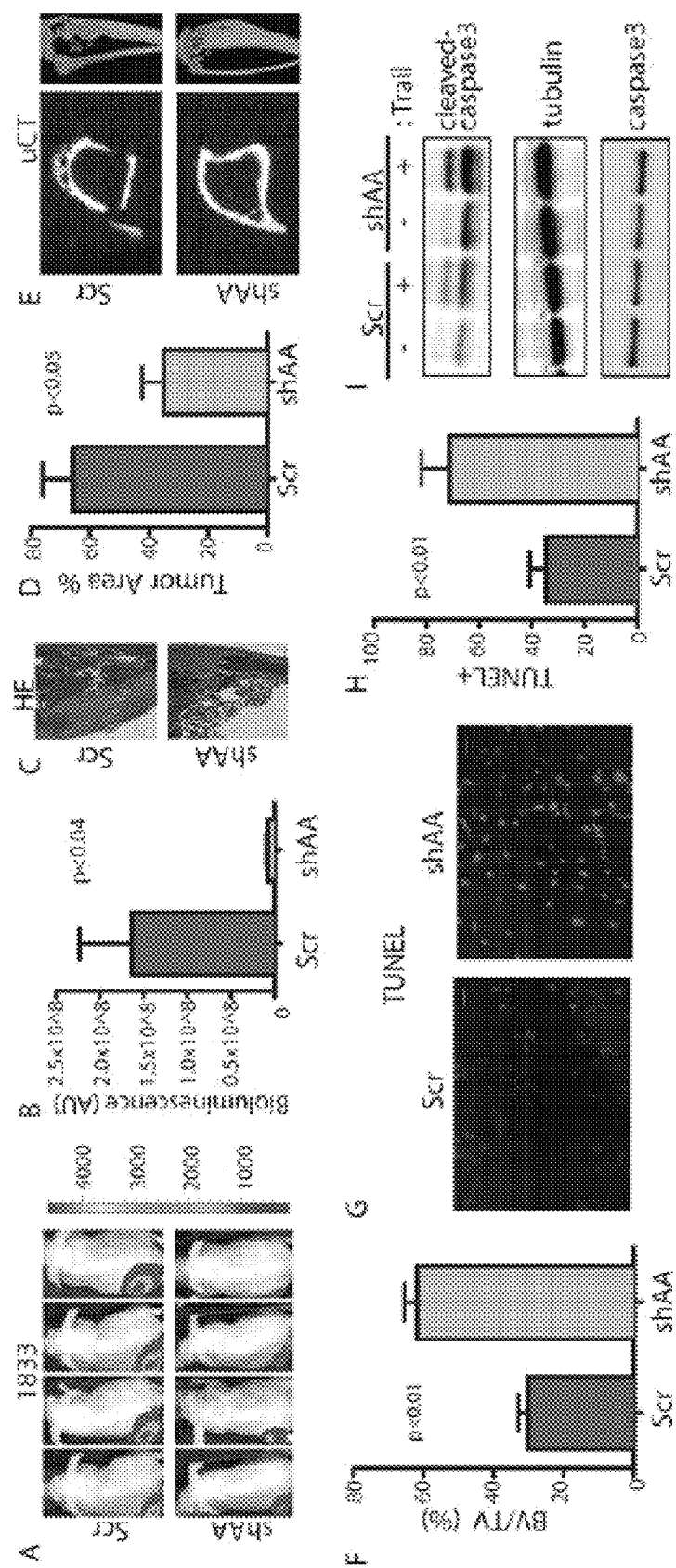
FIG. 6 demonstrates that ABL kinases are required for tumor survival and tumor-induced osteolysis in the bone microenvironment (A and B). Control or ABL1/ABL2 knockdown 1833 cells ($1\times10^5$) were injected directly into the tibias of the mice. Representative bioluminescent images (A) mice at day 21 after inoculation and quantification (B) of bone lesions are shown. n=5 mice per group. (C and D) Representative H&E staining (C) and quantification (D) of H&E-stained tumor area of mouse tibias from each group. n=3 mice per group. Scale bar, 500 µm. (E and F) Representative 30 µCT reconstruction of mouse tibias (E) and quantification (F) of bone volume/total volume from µCT analysis. n=3 mice. (G and H) Representative images (G) of TUNEL (terminal deoxynucleotidyl transferase-mediated deoxyuridine triphosphate nick end labeling) staining of cells treated with TRAIL and the indicated shRNA and quantification of the percent of TUNEL-positive cells (H). n=3 biological replicates. Scale bar, 100 µm (I) immunoblotting was performed using the indicated antibodies on whole-cell lysates from cells incubated or not with TRAIL. n=3 blots.

Example 5: ABL Kinases are Required for Tumor Cell Survival and Tumor-Induced Osteolysis in the Bone-Microenvironment To directly examine whether ABL kinases play a role in regulating the colonization and survival of breast cancer cells in the bone microenvironment, control or ABL1/ABL2 knockdown breast cancer cells were injected directly into the tibia of immuno-deficient mice. Depletion of the ABL kinases reduced tumor expansion in the tibia as measured by both F4 bioluminescence imaging (FIGS. 6, A and B) and histological staining (FIGS. 6, C and D). Moreover, three-dimensional 3D-μCT reconstruction of the tibia revealed that mice injected with control cells had a significantly higher degree of osteolysis with a decreased ratio of bone volume to total volume compared to mice injected with ABL1/ABL2 knockdown breast cancer cells (FIGS. 6, E and F). Depletion of the ABL kinases did not affect breast cancer cell proliferation or colony formation in vitro (FIG. 11). Therefore, these findings suggest that ABL1/ABL2-dependent expansion of breast cancer cells is mediated by factors present in the bone microenvironment.

Bone metastasis requires reciprocal interactions between tumor cells, stromal cells, and bone cells (Waning, et al., *Clin. Cancer Res.*, 2014; Roodman, *N. Engl. J. Med.*, 2004). Several soluble factors released by stromal cells within the bone microenvironment promote tumor growth and survival (Ell et al., *Cell*, 2012). These factors include chemokine (C-X-C motif) ligand 12 (CXCL12), a chemokine produced by bone marrow mesenchymal cells that functions as a chemoattractant and survival factor for cells bearing the chemokine (C-X-C motif) receptor 4 (CXCR4), and insulin-like growth factor 1 (IGF-1), a factor that is stored in the bone matrix and released during osteolysis (Zhang et al., *Cancer Cell*, 2009). It has been shown previously that ABL kinases are activated by the binding of CXCL12 and IGF-1 to their cognate receptors (Ganguly et al., *Genes Cancer*, 2012; Smith-Pearson et al., *J. Biol. Chem.*, 2010). Therefore, the effect of loss of ABL kinases on activation of AKT-mediated survival by these factors was examined. It was found that CXCL12- and IGF-1-induced activation of AKT is independent of ABL1 and ABL2 in 1833 breast cancer cells (FIGS. 15, A and B). In contrast, it was observed that ABL kinases protect breast cancer cells from TRAIL (tumor necrosis factor (TNF)-related apoptosis-inducing ligand)-induced cell death (FIG. 6, G to I). TRAIL is a pro-apoptotic member of the TNF family, which induces apoptosis by binding to the cell death receptors DR4 and DR5 (Ashkenazi, *Nat. Rev. Cancer*, 2002). TRAIL and DR5 are present in clinical breast cancer bone metastases specimens, and DR4 and DR5 are present in 80% of patient bone tumor biopsies (Zhang et al., *Cancer Cell*, 2009, Mitsiades et al., *Cancer Res.*, 2001). TRAIL enhanced apoptosis as measured by cleavage of caspase-3 (FIG. 6I), and knockdown of ABL kinases increased the sensitivity of 1833 breast cancer cells to the pro-apoptotic effects of TRAIL (FIG. 6, G to I). These data suggest that ABL kinases promote breast cancer metastasis to the bone in part by increasing tumor cell survival within the bone microenvironment.

Figure 7:
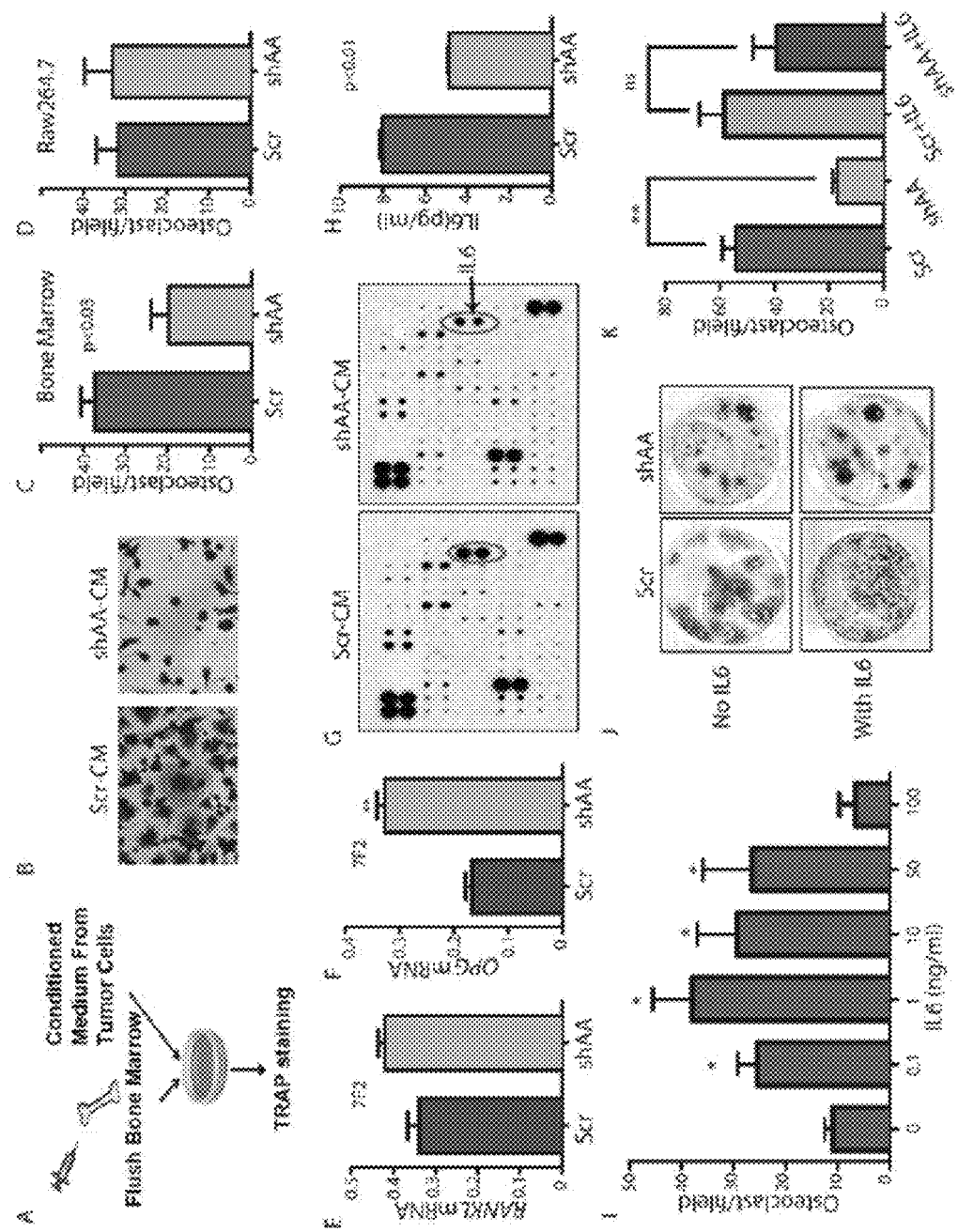
FIG. 7 demonstrates that depletion of ABL kinases impairs tumor-induced osteoclast activation in part by decreasing IL-6 secretion. (A) In vitro osteoclastogenesis assay. (B) TRAP staining of bone marrow cells treated with conditioned medium (CM) from 1833 breast cancer cells. Scale bar, 50 µm. (C) Quantification of TRAP$^+$ cells in (B). (D) Quantification of TRAP$^+$ cells derived from RAW264.7 cells; ns, not significant. (E and F) RANKL (E) and OPG (F) expression was detected by reverse transcription polymerase chain reaction (RT-PCR) of the osteoblast cell line 7F2 treated with conditioned medium harvested from the indicated 1833 cells. (G) identification of differentially expressed cytokines in the conditioned medium of 1833 cells using a cytokine antibody array. n=2 biological replicates. (H) ELISA quantification of IL-6 in conditioned medium of 1833 cells. (I) Quantification of TRAP$^+$ bone marrow-derived osteoclasts incubated with the indicated doses of IL-6. *Significantly different from O. P value was calculated using one-way ANOVA followed by Tukey's post hoc test. (J) TRAP staining of bone marrow treated with conditioned medium from 1833 cells with or without added IL-6. (K) Quantification of TRAP$^+$ osteoclasts in (J).

Example 6: Depletion of ABL Kinases Impairs Tumor-Induced Osteoclast Activation in Part by Decreased IL-6 Production Osteoclast activation plays a central role in the progression of breast cancer bone metastasis. To directly examine whether ABL kinases regulate tumor-induced osteoclast activation, an in vitro osteoclastogenesis assay was employed (FIG. 7A). Mouse primary bone marrow cells were treated (FIG. 7A) with conditioned medium from control or ABL1/ABL2 knockdown breast cancer cells and then stained for tartrate-resistant acid phosphatase (TRAP), an osteoclast marker. Bone marrow cells cultured with conditioned medium derived from ABL1/ABL2 knockdown 1833 and SKBR3 breast cancer cells had decreased numbers of TRAP+ cells compared to the control groups (FIGS. 7, B and C, and FIGS. 16, A and B). These data suggest that inactivation of the ABL kinases in breast cancer cells may impair the secretion of soluble factor(s) required for osteoclast activation. Because the bone marrow contains a heterogeneous population of cells, factors secreted in an ABL1/ABL2-dependent manner might interact directly with osteoclast progenitors and promote their differentiation or might instead function to regulate osteoclasts indirectly by modulating the activity of osteoblasts (Sethi et al., *Cancer Cell*, 2011). To test the first possibility, the osteoclastogenesis assay was carried out using the RAW264.7 murine pre-osteoclast cell line. Conditioned medium derived from ABL1/ABL2 knockdown 1833 breast cancer cells did not impair tumor-induced RAW264.7 pre-osteoclast differentiation (FIG. 7D). These findings suggest that ABL kinases regulate osteoclast maturation indirectly, possibly by modulating osteoblast function.

Osteoblasts modulate osteoclast activity through secretion of the TNF family member RANKL (receptor activator of nuclear factor kB ligand). Binding of RANKL to the RANK receptor on the surface of osteoclasts activates a pathway essential for osteoclast differentiation. Osteoprotegerin (OPG), a soluble decoy receptor for RANKL, is also produced by osteoblasts and antagonizes the activity of RANKL (Simonet et al., *Cell*, 1997). Several tumor-derived bone metastasis factors can increase RANKL production or decrease OPG secretion by osteoblasts, thereby promoting osteoclast differentiation and activation (Waning, et al., *Clin. Cancer Res.*, 2014; Lu et al., *Genes Dev.*, 2009). To evaluate whether ABL kinases might regulate the secretion of osteoblast-derived RANKL or OPG leading to osteoclast differentiation, RANKL and OPG mRNA abundance was analyzed in the murine osteoblast cell line 7F2 in response to conditioned medium from control and ABL1/ABL2 knockdown breast cancer cells. Whereas conditioned medium from ABL1/ABL2-depleted breast cancer cells did not affect RANKL abundance in osteoblasts compared with the cells treated with control conditioned medium (FIG. 7E), conditioned medium from breast cancer cells lacking ABL kinases increased OPG abundance in the osteoblast cell line (FIG. 7F). These findings suggest that ABL kinases promote tumor-induced osteoclast activation in part by increasing OPG abundance in osteoblasts.

To identify tumor-secreted cytokines regulated by the ABL kinases that promote breast cancer metastasis to the bone, a human cytokine antibody array was used to identify changes in cytokine concentrations in the conditioned medium from control and ABL1/ABL2 knockdown cells. It was determined that IL-6 concentrations were decreased in the conditioned medium derived from ABL1/ABL2 knockdown cells compared to that from control cells (FIG. 7G), results that were validated by enzyme-linked immunosorbent assay (ELISA) (FIG. 7H). IL-6 is a multifunctional cytokine with pleiotropic functions that include inducing osteoclast activation, enhancing bone resorption, and increasing metastasis (Tamura et al., *Proc. Natl. Acad. Sci. USA*, 1993; Udagawa et al., *J. Exp. Med.*, 1995; Yin et al., *Cell Res.*, 2005). Inhibition of the IL-6 receptor directly blocks osteoclast formation in vitro and in vivo (Axmann, et al., *Arthritis Rheum.*, 2009). Thus, addition of IL-6 was evaluated for the ability to in part rescue defective osteoclastogenesis induced by conditioned medium from breast cancer cells depleted of the ABL kinases. The optimal dose of IL-6 required to promote maturation of osteoclasts was added (FIG. 7I) to conditioned medium derived from ABL1/ABL2 knockdown breast cancer cells. Addition of IL-6 to reconstituted conditioned medium from ABL1/ABL2-depleted breast cancer cells partially restored osteoclast activation (FIGS. 7, J and K). IL-6 induced RANKL expression but suppressed OPG expression in the 7F2 osteoblast cell line (FIGS. 17, A and B). Thus, depletion of the ABL kinases in breast cancer cells and the accompanying decrease in IL-6 secretion result in enhanced OPG expression and reduced overall RANKL/OPG ratio, thereby decreasing osteoclast differentiation and bone destruction.

Example 7: Next-Generation Sequencing Reveals ABL1/ABL2-Regulated Genes in Breast Cancer Cells To gain insight into the signaling pathway(s) required for ABL1/ABL2-dependent bone metastasis, the consequences of single or double inactivation of ABL1 and ABL2 on the transcriptome of breast cancer cells was evaluated using next-generation sequencing (RNAseq) analysis (FIG. 8 and FIG. 18A). 180 genes showed significantly decreased expression and 40 genes showed significantly increased expression in ABL1/ABL2 knockdown cells (FIG. 18B and Table 2).

TABLE 2

| gene_id | status | Control (Scr) | ABL1/ABL2 knockdown (shAA) | log2_fold_change | p_value | significant |
|---|---|---|---|---|---|---|
| ABI3BP | OK | 1.77318 | 0.373013 | −2.24904 | 2.43E−05 | yes |
| ABL1 | OK | 14.5002 | 2.44777 | −2.56653 | 8.92E−10 | yes |
| ABL2 | OK | 22.2651 | 4.96249 | −2.16565 | 1.94E−07 | yes |
| ACTG2 | OK | 4.40434 | 14.5112 | 1.72016 | 0.000490382 | yes |
| ADAMTS6 | OK | 10.4481 | 3.55367 | −1.55586 | 1.95E−05 | yes |
| ADAMTS7 | OK | 1.90679 | 0.566666 | −1.75057 | 0.000786492 | yes |
| ADAMTSL4 | OK | 8.71378 | 1.91026 | −2.18953 | 1.21E−06 | yes |
| AFAP1L2 | OK | 4.00897 | 1.05156 | −1.9307 | 4.71E−05 | yes |
| ALDH3A1 | OK | 1.01348 | 0.15927 | −2.66977 | 0.000204128 | yes |
| ALPK1 | OK | 1.51232 | 0.273919 | −2.46494 | 4.67E−06 | yes |
| APOBEC3G | OK | 1.54296 | 0.297884 | −2.37287 | 0.00014069 | yes |
| APOE | OK | 2.55038 | 0.553793 | −2.2033 | 0.000621684 | yes |
| AQP11 | OK | 0.187638 | 0.938074 | 2.32175 | 0.000561313 | yes |
| ARHGAP30 | OK | 1.3869 | 0.396212 | −1.80752 | 0.000778843 | yes |
| ARL4C | OK | 50.6575 | 22.9726 | −1.14086 | 0.000510218 | yes |
| ATP2A3 | OK | 1.01172 | 0.240977 | −2.06984 | 0.000786882 | yes |
| BRMS1L | OK | 4.31437 | 13.2113 | 1.61455 | 0.000127499 | yes |
| C13orf15 | OK | 29.7258 | 10.2321 | −1.53861 | 0.00036022 | yes |
| C20orf4 | OK | 8.38864 | 23.1683 | 1.46564 | 0.000103674 | yes |
| CACNG7 | OK | 28.7262 | 9.11097 | −1.65669 | 3.54E−05 | yes |
| CCBL1 | OK | 12.9887 | 4.12341 | −1.65534 | 0.000277752 | yes |
| CCDC25 | OK | 20.4681 | 6.49377 | −1.65625 | 6.85E−06 | yes |
| CD59 | OK | 85.4344 | 36.4392 | −1.22933 | 0.00046364 | yes |
| CD74 | OK | 17.3265 | 2.30287 | −2.91147 | 1.49E−07 | yes |
| CDC42EP5 | OK | 9.27094 | 1.48041 | −2.64672 | 8.94E−06 | yes |
| CDH2 | OK | 0.287241 | 1.32663 | 2.20743 | 8.51E−05 | yes |
| CFB | OK | 2.34469 | 0.553321 | −2.08321 | 0.000135481 | yes |
| CGN | OK | 1.4361 | 4.22344 | 1.55627 | 0.000404816 | yes |
| CIITA | OK | 0.603533 | 0.132348 | −2.18909 | 0.000419877 | yes |
| CKAP4 | OK | 118.858 | 54.5961 | −1.12237 | 0.000522313 | yes |
| CNOT6 | OK | 9.02689 | 21.4854 | 1.25106 | 0.000220172 | yes |
| CNOT8 | OK | 34.2259 | 9.38441 | −1.86675 | 4.79E−07 | yes |
| COL1A1 | OK | 7.09801 | 18.2315 | 1.36095 | 0.000122524 | yes |
| COL1A2 | OK | 2.37285 | 7.8701 | 1.72976 | 3.26E−05 | yes |
| COL8A1 | OK | 70.1949 | 24.8006 | −1.50099 | 3.88E−05 | yes |
| COL8A2 | OK | 0.89169 | 0.124747 | −2.83753 | 5.08E−06 | yes |
| CREB3L3 | OK | 0.919189 | 0.111793 | −3.03953 | 2.15E−06 | yes |
| CSF1 | OK | 64.7765 | 26.2168 | −1.30498 | 0.000343084 | yes |
| CSPG4 | OK | 12.1314 | 4.67716 | −1.37505 | 0.000100085 | yes |
| CST1 | OK | 7.54343 | 0.989636 | −2.93025 | 1.28E−06 | yes |
| CTSC | OK | 145.661 | 55.1225 | −1.4019 | 0.000108986 | yes |
| CTSS | OK | 0.621009 | 0.124328 | −2.32046 | 0.000251768 | yes |
| CUL7 | OK | 21.1372 | 8.50282 | −1.31377 | 0.000570716 | yes |
| CXorf38 | OK | 13.8011 | 5.52116 | −1.32174 | 0.000367991 | yes |
| CYP27B1 | OK | 1.95382 | 0.45397 | −2.10563 | 0.000319559 | yes |
| DCAF7 | OK | 46.9894 | 17.4624 | −1.42808 | 1.15E−05 | yes |
| DMRT2 | OK | 0.104723 | 0.75773 | 2.85511 | 0.000486949 | yes |
| DRAM1 | OK | 17.7768 | 6.55735 | −1.43881 | 0.000145422 | yes |
| DUSP1 | OK | 163.8 | 52.8583 | −1.63173 | 6.33E−07 | yes |
| DYNLT1 | OK | 81.3758 | 24.6076 | −1.72549 | 1.25E−05 | yes |
| ECM1 | OK | 28.989 | 10.7592 | −1.42994 | 0.00020844 | yes |
| ELMO1 | OK | 0.272358 | 0.0463901 | −2.55362 | 0.000666803 | yes |
| EML2 | OK | 54.5349 | 16.9395 | −1.68679 | 1.05E−05 | yes |
| ENPP1 | OK | 39.1868 | 17.7103 | −1.14578 | 0.000410896 | yes |
| EREG | OK | 18.2475 | 7.85336 | −1.21632 | 0.000672304 | yes |
| EXD3 | OK | 1.88113 | 0.286666 | −2.71416 | 4.78E−06 | yes |
| FAM111B | OK | 3.66907 | 10.3264 | 1.49285 | 0.000198072 | yes |
| FAM133A | OK | 0.418568 | 0.0679606 | −2.62269 | 0.000446266 | yes |
| FAM46C | OK | 6.53543 | 2.0768 | −1.65392 | 6.39E−05 | yes |
| FBXO27 | OK | 26.1772 | 8.52605 | −1.61836 | 2.78E−05 | yes |
| FCGRT | OK | 9.75802 | 2.97668 | −1.71288 | 0.000549272 | yes |
| FOS | OK | 48.863 | 18.6579 | −1.38896 | 8.29E−05 | yes |
| FOSB | OK | 7.14909 | 2.2033 | −1.69809 | 0.000207336 | yes |
| FRAS 1 | OK | 3.47837 | 0.922834 | −1.91427 | 2.17E−06 | yes |

TABLE 2-continued

| gene_id | status | Control (Scr) | ABL1/ABL2 knockdown (shAA) | log2_fold_change | p_value | significant |
|---|---|---|---|---|---|---|
| FSTL1 | OK | 84.2835 | 34.9094 | −1.27163 | 9.08E−05 | yes |
| GBGT1 | OK | 0.899354 | 0.0636293 | −3.82113 | 6.11E−06 | yes |
| GBP2 | OK | 5.79671 | 1.14846 | −2.33554 | 1.38E−06 | yes |
| GCA | OK | 7.87002 | 2.46942 | −1.67219 | 0.000208199 | yes |
| GGT1 | OK | 5.91954 | 1.44058 | −2.03884 | 0.0007834 | yes |
| GIMAP2 | OK | 0.878286 | 0.129972 | −2.75649 | 0.000246358 | yes |
| GMFG | OK | 22.8122 | 4.58505 | −2.31479 | 6.19E−06 | yes |
| GMPR2 | OK | 62.1332 | 14.3958 | −2.10972 | 1.44E−07 | yes |
| GPR153 | OK | 9.91108 | 3.41476 | −1.53726 | 0.000331943 | yes |
| GRAMD3 | OK | 31.6943 | 12.9908 | −1.28673 | 0.000614673 | yes |
| GRPR | OK | 0.324088 | 0.0429749 | −2.91482 | 0.000703277 | yes |
| HAS2 | OK | 10.2357 | 2.85624 | −1.84142 | 3.64E−05 | yes |
| HDGF | OK | 157.824 | 41.0762 | −1.94194 | 1.13E−07 | yes |
| HEG1 | OK | 29.7432 | 12.1616 | −1.29022 | 7.10E−05 | yes |
| HES7 | OK | 7.75807 | 1.67422 | −2.21221 | 2.89E−05 | yes |
| HIST1H1C | OK | 46.5173 | 133.33 | 1.51916 | 3.04E−05 | yes |
| HIST1H2AC | OK | 15.5383 | 86.4435 | 2.47592 | 6.11E−08 | yes |
| HIST1H2BD | OK | 11.9815 | 62.1497 | 2.37494 | 4.04E−05 | yes |
| HIST1H2BE | OK | 1.03812 | 5.74736 | 2.46892 | 0.000506746 | yes |
| HIST1H2BJ | OK | 4.59929 | 21.5016 | 2.22496 | 7.16E−05 | yes |
| HIST1H2BK | OK | 95.196 | 347.602 | 1.86846 | 1.89E−08 | yes |
| HIST1H4H | OK | 1.49865 | 15.1955 | 3.34191 | 1.34E−06 | yes |
| HIST2H2AA3 | OK | 16.6082 | 51.0364 | 1.61963 | 0.000572231 | yes |
| HIST2H2BE | OK | 1.40623 | 5.22356 | 1.8932 | 0.000309176 | yes |
| HLA-DPA1 | OK | 0.836357 | 0.0659735 | −3.66416 | 0.000249169 | yes |
| HLA-DRA | OK | 2.36833 | 0.174254 | −3.76461 | 1.14E−07 | yes |
| HLA-DRB 1 | OK | 1.10537 | 0.0455755 | −4.60013 | 0.000484672 | yes |
| HOXB9 | OK | 43.6879 | 12.4656 | −1.80928 | 3.70E−07 | yes |
| HSPB8 | OK | 1.35821 | 7.82538 | 2.52645 | 5.84E−07 | yes |
| HSPG2 | OK | 10.6493 | 3.77694 | −1.49548 | 1.27E−05 | yes |
| ID1 | OK | 31.9426 | 9.10398 | −1.81091 | 7.25E−05 | yes |
| IFITM1 | OK | 57.7506 | 16.4692 | −1.81007 | 3.64E−05 | yes |
| IFITM2 | OK | 128.45 | 53.0937 | −1.2746 | 0.000587832 | yes |
| IGFBP3 | OK | 46.3828 | 15.4092 | −1.5898 | 8.28E−06 | yes |
| IL24 | OK | 10.2776 | 1.22748 | −3.06572 | 1.82E−05 | yes |
| ITGA10 | OK | 11.7989 | 1.65214 | −2.83624 | 8.23E−12 | yes |
| ITGB4 | OK | 20.721 | 6.00343 | −1.78724 | 8.28E−07 | yes |
| KAL1 | OK | 2.69715 | 0.814156 | −1.72806 | 0.00024116 | yes |
| KAZALD1 | OK | 6.58795 | 2.10993 | −1.64263 | 0.000719169 | yes |
| KIRREL3 | OK | 7.23959 | 1.72639 | −2.06815 | 0.000294897 | yes |
| KISS1 | OK | 136.972 | 30.9789 | −2.14452 | 4.06E−08 | yes |
| KRT15 | OK | 8.68815 | 2.50382 | −1.79492 | 0.000145767 | yes |
| KRT19 | OK | 361.238 | 153.83 | −1.23161 | 0.000152095 | yes |
| KRTAP2-1 | OK | 3.16418 | 0.497172 | −2.67001 | 0.000302386 | yes |
| KRTAP4-8 | OK | 2.22111 | 0.312518 | −2.82927 | 0.0001126 | yes |
| LAPTM5 | OK | 44.3401 | 14.3079 | −1.6318 | 6.75E−06 | yes |
| LAT2 | OK | 14.3369 | 3.15331 | −2.1848 | 2.66E−05 | yes |
| LIMA1 | OK | 67.8704 | 23.9495 | −1.50279 | 5.93E−06 | yes |
| LINC00261 | OK | 4.43113 | 14.5457 | 1.71484 | 4.19E−06 | yes |
| LOC100289187 | OK | 3.8872 | 0.573685 | −2.7604 | 5.62E−05 | yes |
| LOC100505622 | OK | 5.8395 | 1.10337 | −2.40393 | 9.92E−05 | yes |
| LOC100507127 | OK | 19.5235 | 7.67133 | −1.34766 | 0.000309407 | yes |
| LOC152225 | OK | 27.8011 | 10.6487 | −1.38447 | 0.000238641 | yes |
| LOC152742 | OK | 0.565455 | 0.0271403 | −4.3809 | 7.90E−05 | yes |
| LOC284751 | OK | 1.86434 | 0.478666 | −1.96157 | 0.00073505 | yes |
| LOC647946 | OK | 1.44766 | 0.251221 | −2.52669 | 3.62E−05 | yes |
| LOC728730 | OK | 8.35692 | 2.83655 | −1.55883 | 0.000500893 | yes |
| LOC730755 | OK | 45.0184 | 5.39706 | −3.06027 | 2.25E−10 | yes |
| MAGEC2 | OK | 2.71235 | 0.275769 | −3.29801 | 8.78E−08 | yes |
| MALL | OK | 13.7824 | 4.96951 | −1.47165 | 0.000374519 | yes |
| MAPK14 | OK | 44.6474 | 19.1939 | −1.21793 | 0.000286866 | yes |
| 4-Mar | OK | 15.2329 | 4.45124 | −1.77492 | 4.16E−06 | yes |
| MEGF6 | OK | 1.00404 | 0.273702 | −1.87514 | 0.000540393 | yes |
| MEIS3 | OK | 2.01826 | 0.375826 | −2.42497 | 0.000251761 | yes |
| MIR100HG | OK | 35.9188 | 12.9785 | −1.46862 | 3.20E−05 | yes |
| MORF4L1 | OK | 227.513 | 74.6733 | −1.60729 | 1.10E−06 | yes |
| MRC2 | OK | 14.173 | 4.10715 | −1.78694 | 1.58E−06 | yes |
| MSMO1 | OK | 102.552 | 40.0285 | −1.35726 | 0.000197116 | yes |
| MT1E | OK | 97.1589 | 305.348 | 1.65204 | 4.57E−06 | yes |
| MTRNR2L1 | OK | 50.4124 | 20.9275 | −1.26838 | 0.000452569 | yes |
| MTRNR2L2 | OK | 672.845 | 270.719 | −1.31348 | 0.000784507 | yes |
| MTRNR2L8 | OK | 394.109 | 155.52 | −1.3415 | 3.94E−05 | yes |
| MYH15 | OK | 0.897276 | 0.203375 | −2.14141 | 4.85E−05 | yes |
| NAT16 | OK | 0.960428 | 0.215133 | −2.15845 | 0.000707495 | yes |
| NEAT1 | OK | 43.694 | 170.974 | 1.96827 | 2.06E−09 | yes |

TABLE 2-continued

| gene_id | status | Control (Scr) | ABL1/ABL2 knockdown (shAA) | log2_fold_change | p_value | significant |
|---|---|---|---|---|---|---|
| NIPSNAP1 | OK | 50.0781 | 19.2022 | −1.38291 | 0.000542122 | yes |
| NKAPP1 | OK | 0.0761171 | 0.461006 | 2.59849 | 0.000622297 | yes |
| NMNAT2 | OK | 6.48564 | 1.94243 | −1.73939 | 3.63E−05 | yes |
| NNMT | OK | 5.6062 | 0.695152 | −3.01162 | 8.85E−08 | yes |
| NOTCH3 | OK | 2.23403 | 0.709619 | −1.65453 | 0.00064858 | yes |
| NPM2 | OK | 1.12447 | 0.115312 | −3.28563 | 4.62E−05 | yes |
| NPTN | OK | 28.5524 | 66.3047 | 1.2155 | 0.000788545 | yes |
| OAS1 | OK | 6.15395 | 1.49621 | −2.0402 | 0.000671787 | yes |
| OCEL1 | OK | 27.7982 | 8.92824 | −1.63854 | 0.000180319 | yes |
| OCRL | OK | 17.9785 | 6.46308 | −1.47598 | 0.000636423 | yes |
| OSBPL5 | OK | 8.49977 | 2.4869 | −1.77308 | 3.25E−05 | yes |
| OXTR | OK | 1.97638 | 0.442715 | −2.15841 | 5.46E−05 | yes |
| PAQR8 | OK | 6.28517 | 1.66226 | −1.91881 | 1.46E−05 | yes |
| PCSK9 | OK | 64.3228 | 8.57875 | −2.90649 | 4.44E−16 | yes |
| PDE3B | OK | 0.299156 | 1.63528 | 2.45057 | 4.81E−06 | yes |
| PDE9A | OK | 6.44286 | 1.43199 | −2.16967 | 0.000276155 | yes |
| PDIA4 | OK | 82.0461 | 22.6365 | −1.85779 | 1.84E−08 | yes |
| PHTF2 | OK | 8.93693 | 22.0664 | 1.304 | 0.000784105 | yes |
| PIGW | OK | 6.12765 | 19.7353 | 1.68737 | 5.32E−05 | yes |
| PIGZ | OK | 0.569224 | 0.0704711 | −3.01389 | 0.000103526 | yes |
| PLAT | OK | 345.287 | 68.3719 | −2.33632 | 9.85E−12 | yes |
| PLCH2 | OK | 1.78874 | 0.463838 | −1.94725 | 0.000244924 | yes |
| POLR2A | OK | 28.6069 | 65.4801 | 1.19469 | 0.000235766 | yes |
| POTEF | OK | 1.28954 | 5.2349 | 2.0213 | 7.07E−06 | yes |
| POTEKP | OK | 4.09351 | 16.3678 | 1.99945 | 5.81E−07 | yes |
| POTEM | OK | 0.485698 | 1.54849 | 1.67273 | 0.000715583 | yes |
| PPAP2B | OK | 8.90267 | 2.49706 | −1.83401 | 2.93E−05 | yes |
| PRICKLE2 | OK | 2.09826 | 0.651728 | −1.68685 | 0.000314251 | yes |
| PRKAG2 | OK | 39.0343 | 15.3784 | −1.34384 | 0.000306966 | yes |
| PTK2B | OK | 0.894681 | 0.143562 | −2.6397 | 0.000108282 | yes |
| PYCARD | OK | 12.2415 | 2.61528 | −2.22674 | 0.000117652 | yes |
| RAB38 | OK | 11.0276 | 3.39597 | −1.69922 | 0.000380073 | yes |
| RAP1GAP2 | OK | 17.0795 | 6.29121 | −1.44085 | 0.000210868 | yes |
| RASD1 | OK | 34.4324 | 9.85228 | −1.80524 | 7.22E−06 | yes |
| RCBTB2 | OK | 0.343453 | 1.72464 | 2.32811 | 4.40E−05 | yes |
| RIMS1 | OK | 2.66298 | 0.253422 | −3.39343 | 1.27E−07 | yes |
| ROBO2 | OK | 0.581676 | 0.121629 | −2.25773 | 6.92E−05 | yes |
| RPRD1B | OK | 24.6495 | 8.94044 | −1.46314 | 3.66E−05 | yes |
| SAT1 | OK | 178.671 | 64.5366 | −1.46911 | 2.65E−05 | yes |
| SCARB2 | OK | 34.6914 | 9.39402 | −1.88476 | 5.33E−08 | yes |
| SCG2 | OK | 3.35489 | 0.309104 | −3.4401 | 5.10E−10 | yes |
| SDC4 | OK | 100.839 | 34.8538 | −1.53267 | 3.22E−06 | yes |
| SEC16B | OK | 0.719453 | 0.165627 | −2.11896 | 0.000442121 | yes |
| SEZ6L2 | OK | 12.3669 | 4.34442 | −1.50924 | 0.00074365 | yes |
| SFPQ | OK | 60.2063 | 139.423 | 1.21148 | 0.000188023 | yes |
| SKAP1 | OK | 1.82404 | 0.345903 | −2.3987 | 0.000547967 | yes |
| SKP1 | OK | 115.59 | 42.1069 | −1.45689 | 1.30E−05 | yes |
| SLAMF7 | OK | 3.45169 | 19.6211 | 2.50703 | 7.94E−10 | yes |
| SLC25A4 | OK | 9.03451 | 21.9258 | 1.27911 | 0.000259235 | yes |
| SLC25A43 | OK | 9.89554 | 3.29292 | −1.58741 | 0.000336164 | yes |
| SLC2A10 | OK | 0.943429 | 0.238666 | −1.98292 | 0.0007881 | yes |
| SLC36A1 | OK | 2.4013 | 8.8694 | 1.88502 | 3.53E−06 | yes |
| SLFN5 | OK | 2.7288 | 0.618243 | −2.14202 | 1.74E−05 | yes |
| SNCAIP | OK | 4.0467 | 0.582107 | −2.79739 | 1.02E−07 | yes |
| SOX21 | OK | 0.82367 | 0.0379844 | −4.43859 | 1.92E−06 | yes |
| STAT5A | OK | 7.34484 | 2.50511 | −1.55186 | 0.000264618 | yes |
| STBD1 | OK | 5.16531 | 1.5711 | −1.71708 | 0.00051249 | yes |
| STC1 | OK | 74.2171 | 14.7418 | −2.33184 | 3.61E−12 | yes |
| STXBP6 | OK | 5.47816 | 1.30106 | −2.074 | 6.50E−05 | yes |
| SYT1 | OK | 3.9326 | 0.917351 | −2.09994 | 5.91E−06 | yes |
| SYT9 | OK | 0.386942 | 0.0436695 | −3.14742 | 2.36E−05 | yes |
| THSD4 | OK | 9.84323 | 2.85735 | −1.78445 | 9.75E−07 | yes |
| TIE1 | OK | 1.83322 | 0.273681 | −2.74381 | 1.26E−06 | yes |
| TM4SF1 | OK | 499.169 | 166.984 | −1.57982 | 1.93E−06 | yes |
| TMEM14C | OK | 106.141 | 28.2458 | −1.90988 | 1.81E−07 | yes |
| TMEM229B | OK | 1.70892 | 0.452357 | −1.91755 | 0.000504437 | yes |
| TMEM64 | OK | 3.9275 | 11.2021 | 1.51208 | 0.00030457 | yes |
| TMPRSS15 | OK | 1.23079 | 0.186765 | −2.72029 | 3.77E−06 | yes |
| TNC | OK | 9.00158 | 3.93382 | −1.19425 | 0.000645734 | yes |
| TNFRSF11B | OK | 1.17087 | 0.248287 | −2.2375 | 0.000301207 | yes |
| TNS4 | OK | 4.78056 | 1.44887 | −1.72225 | 0.000183089 | yes |
| TOMM34 | OK | 124.588 | 20.5255 | −2.60168 | 2.44E−14 | yes |
| TRPV2 | OK | 4.54026 | 1.01879 | −2.15591 | 2.22E−05 | yes |
| TSPAN1 | OK | 4.50344 | 1.15337 | −1.96517 | 0.000326507 | yes |
| TXNIP | OK | 322.237 | 59.356 | −2.44066 | 4.33E−13 | yes |

TABLE 2-continued

| gene_id | status | Control (Scr) | ABL1/ABL2 knockdown (shAA) | log2_fold_change | p_value | significant |
|---|---|---|---|---|---|---|
| VAMP5 | OK | 2.04949 | 0.307138 | −2.7383 | 0.000466612 | yes |
| WBSCR27 | OK | 7.08505 | 1.77504 | −1.99693 | 0.000394317 | yes |
| WNK4 | OK | 2.43988 | 0.625406 | −1.96395 | 0.000156328 | yes |
| WWTR1 | OK | 29.8543 | 12.5907 | −1.24558 | 0.000347804 | yes |
| ZBTB4 | OK | 22.7821 | 7.81093 | −1.54434 | 0.000164258 | yes |
| ZDHHC20 | OK | 12.1756 | 27.0512 | 1.1517 | 0.000557528 | yes |

Principal components analysis revealed that transcripts altered in breast cancer cells depleted of ABL1, ABL2, or both ABL1 and ABL2 were clustered and were distinct from the control group (FIG. 18C). This analysis indicated that the transcriptomes of single- and double-knockdown cells were similar to each other but different from that of the control cells, supporting the quality and validity of the RNAseq analysis. Comparison of the transcripts revealed that breast cancer cells with knockdown of ABL2 alone shared a similar gene expression pattern with that of the ABL1/ABL2 double knockdown cells (FIG. 8A and FIG. 18D). Notably, analysis of cell lysates from ABL2-depleted and ABL1/ABL2 double-knockdown breast cancer cells showed a greater reduction of the phosphorylation of CrkL compared to cells with knockdown of ABL1 alone (FIG. 4K). Thus, the altered gene expression profiles correlate with decreased ABL kinase activity in breast cancer cells.

Example 8: ABL Kinases Signal to TAZ and STAT5 to Promote Breast Cancer Bone Metastasis To identify the pathways affected by the inactivation of the ABL kinases in metastatic breast cancer cells, Gene Set Enrichment Analysis (GSEA) were conducted using multiple databases (Subramanianm et al., Proc. Natl. Acad. Sci. USA, 2005). In addition to the GSEA oncogenic signature database, the KEGG (Kyoto Encyclopedia of Genes and Genomes) database and published breast cancer metastasis data sets were used. A gene signature consisting of 273 genes important for breast cancer bone metastasis showed decreased expression in ABL1/ABL2 knockdown cells (FIG. 8B) (Vashisht et al., PLOS One, 2012). Further, inactivation of the ABL kinases resulted in decreased expression of the genes in the Hippo, Janus kinase (JAK)/STAT, and Cytokine/Cytokine receptor pathway signatures (FIG. 8B). To identify key molecular mediators of the ABL kinases implicated in the regulation of the ABL1/ABL2-dependent pathways, the expression of individual genes for transcripts altered by loss of the ABL kinases were analyzed. Among transcripts that were decreased in ABL1/ABL2 knockdown cells were TAZ (also known as WWTR1 (WW domain-containing transcription regulator protein 1)), which encodes a transcriptional coactivator in the Hippo pathway, and STAT5A, which encodes a transcription factor (FIG. 8C).

TAZ and the related YAP1 proteins are components of the Hippo pathway and have been implicated in breast cancer progression and metastasis (Cordenonsi et al., Cell, 2011; Azzolin et al., Cell, 2012). Knockdown of the ABL kinases decreased the mRNA expression of TAZ (FIG. 8C) and reduced the protein abundance of TAZ and its downstream target AXL (FIG. 9A and FIGS. 19, A and B). AXL encodes a receptor tyrosine kinase that promotes breast cancer bone metastasis in mouse models (Gjerdrum et al., Proc. Natl. Acad. Sci. USA, 2010). Knockdown of ABL2, but not of ABL1, reduced TAZ abundance to a similar extent as ABL1/ABL2 double knockdown (FIG. 19A), suggesting that ABL2 has a predominant role in regulating TAZ abundance. Overexpression of ABL1 and ABL2 in both 1833 and parental MDA-MB-231 breast cancer cells increased TAZ abundance (FIG. 19C). Further, immunofluorescence staining analysis indicated that the TAZ protein predominantly (~90%) localized in the nuclei of 1833 breast cancer cells (FIG. 20A), an effect decreased by double knockdown of ABL1 and ABL2 (FIG. 20B).

Similarly, inhibiting ABL kinase activity with the allosteric inhibitor GNF5 decreased TAZ protein abundance (FIG. 21). TAZ protein abundance was not decreased by GNF5 treatment in breast cancer cells expressing murine ABL2-E505K, a mutant that is resistant to the GNF5 allosteric inhibitor (FIG. 21). Moreover, ABL2 mRNA expression positively correlated with TAZ mRNA expression in a TCGA data set of 971 invasive breast cancer patients (FIG. 22).

To evaluate whether loss of ABL kinases affected TAZ activity, chromatin immunoprecipitation (ChIP) analysis was performed using primers for TAZ targets identified by ChIP sequencing analysis (Zanconato et al., Nat. Cell Biol., 2015). Depletion of the ABL kinases decreased TAZ binding to some of its target genes (FIG. 23). Whereas ABL1 has been reported to phosphorylate YAP1 in response to DNA damage (Levy et al., Mol. Cell, 2008), it was found that ABL1/ABL2 knockdown did not substantially alter YAP1 protein abundance (FIG. 9A), nuclear localization (FIGS. 24, A and B), phosphorylation of YAP at Tyr357 (FIG. 24C), or binding to some of its downstream targets (FIG. 23). However, the possibility that ABL kinases might regulate YAP1-mediated expression of other target genes in breast cancer cells cannot be ruled out. Regardless, this data supports a role for ABL kinases in the regulation of TAZ protein abundance and activity in breast cancer cells. Moreover, expression of a constitutively active TAZ S89A mutant in ABL1/ABL2 knockdown breast cancer cells (1833 and SCP28) restored the abundance of its target AXL (FIGS. 9, B and C). Together, these data reveal a functional link between the ABL kinases and TAZ signaling leading to increased AXL abundance in breast cancer cells, and identify a potentially druggable pathway for the treatment of breast cancer bone metastasis.

Inactivation of the ABL kinases in breast cancer cells also decreased STAT5A mRNA and downstream expression of STAT5 target genes, including Tenascin C (TNC) (FIG. 8D). STAT5 belongs to a family of transcription factors that regulate cytokine-induced gene expression and is constitutively activated in several human cancers including breast cancer, where it promotes the expression of genes encoding cell survival factors (Ferbeyre et al., Biochim. Biophys. Acta, 2011). STAT5 is also activated by the oncogenic B cell receptor (BCR)-ABL tyrosine kinase and contributes to the transformation of leukemia cells (de Groot et al., *Blood*, 1999). STAT5 promotes metastasis of human prostate cancer cells (Gu et al., *Endocr. Relat. Cancer*, 2010) and has been implicated in the resistance of metastatic breast cancer cells to targeted therapies (Britschgi et al., *Cancer Cell*, 2012). Moreover, ablation of a STAT5A allele reduces tumor incidence in a mouse model of breast cancer in which mammary epithelial cells express T antigen (Ren et al., *Oncogene*, 2002). Depletion of ABL kinases in breast cancer cells was determined to decrease STAT5A mRNA expression (FIG. 8D) without decreasing total STAT5 protein abundance as measured by Western blotting with antibodies that detect both STAT5A and STAT5B (FIG. 9D and FIGS. 19, A and B). However, depletion of ABL kinases decreased the phosphorylation of STAT5 (FIG. 9D and FIGS. 19, A and B). Conversely, overexpression of ABL kinases, predominantly ABL1, in both 1833 and parental MDA-MB-231 breast cancer cells increased STAT5 phosphorylation (FIG. 19C). Further, double knockdown of ABL1 and ABL2 decreased the abundance of various secreted proteins, including IL-6, TNC, and MMP1 (FIG. 9D). Both MMP1 and IL-6 have been linked to the regulation of osteoclast activation (Lu et al., *Genes Dev.*, 2009; Tamura et al., *Proc. Natl. Acad. Sci. USA*, 1993), and depletion of TNC decreases breast cancer metastasis (Oskarsson et al., *Nat. Med.*, 2011). Expression of a constitutively active STAT5A mutant (STAT5A*) reversed the reduction in MMP1, IL-6, and TNC abundance induced by depletion of both ABL kinases in breast cancer cells (FIGS. 9, E and F, and FIG. 25). These findings support a role for STAT5 in regulating the ABL1/ABL2-dependent secretome.

To evaluate whether the TAZ and STAT5 pathways promote breast cancer bone metastasis downstream of the ABL kinases, the constitutively active mutants TAZ S89A and STAT5* were expressed in ABL1/ABL2 knockdown cells. Expression of either TAZ S89A or STAT5* alone in ABL1/ABL2-depleted breast cancer cells only partially rescued bone metastasis, and expression of both STAT5* and TAZ S89A was required to fully rescue the impaired bone metastasis by ABL1/ABL2-depleted cells (FIGS. 9, G and H). To evaluate whether depletion of TAZ and STAT5 in breast cancer could phenocopy the reduced bone metastasis caused by depletion of ABL1 and ABL2, intra-cardiac injection of control or TAZ/STAT5 double-knockdown 1833 breast cancer cells was performed; cells depleted of TAZ and STAT5 exhibited markedly impaired metastasis that phenocopied the inhibitory effects of ABL1/ABL2 knockdown (FIG. 9, I to K). TAZ and STAT5 might regulate each other (FIG. 26). TAZ knockdown with two distinct shRNAs decreased the phosphorylation of STAT5 and, to a lesser extent, total STAT5 protein abundance (FIG. 26A). Moreover, knockdown of STAT5 with two different shRNAs slightly decreased TAZ protein abundance (FIG. 26B). However, these reciprocal decreases were much lower than those induced by knockdown of the ABL kinases (FIG. 9). Together, these findings suggest that ABL kinases activate the TAZ and STAT5 pathways and that co-activation of their downstream targets promotes the bone metastasis of breast cancer cells in mouse models. Using a TCGA data set with 971 invasive breast cancer patients, we found that patients with alterations in the expression of ABL2 and eight validated downstream targets (TAZ, AXL, CTGF, STAT5A, STAT5B, TNC, IL6, and MMP1) exhibited decreased disease-free survival (FIG. 10A).

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of the claimed embodiments. All of the various embodiments, aspects, and options disclosed herein can be combined in all variations. The scope of the compositions, formulations, methods, and processes described herein include all actual or potential combinations of embodiments, aspects, options, examples, and preferences herein.

All patents and publications cited herein are incorporated by reference herein for the specific teachings thereof as noted, unless other specific statements of incorporation are specifically provided.

What is claimed is:

1. A method of treating cancer in a subject suffering from a cancer associated with ABL kinase hyper-activation, the method comprising inhibiting ABL kinase activity by administering an ABL-specific inhibitor, provided that no non-specific ABL inhibitor is administered to the subject.

2. The method of claim 1, wherein the ABL-specific inhibitor is an allosteric inhibitor.

3. The method of claim 2, wherein the allosteric inhibitor binds to ABL1 and/or ABL2 kinases at the myristoyl binding site.

4. The method of claim 2, wherein the allosteric inhibitor of ABL1 and ABL2 kinases is GNF5 or ABL001.

5. The method of claim 1, wherein the non-specific ABL inhibitor is an ATP-competitive inhibitor.

6. The method of claim 1, wherein the non-specific ABL inhibitor is imatinib, dasatinib, or nilotinib.

7. The method of claim 1, wherein the cancer is characterized by solid tumors.

8. The method of claim 1, wherein the cancer is breast cancer.

9. The method of claim 8, wherein the breast cancer is HER2-positive or basal-like.

10. A method of treating breast cancer in a subject suffering from breast cancer, comprising inhibiting ABL kinase activity by administering an ABL-specific inhibitor.

11. The method of claim 10, wherein the ABL-specific inhibitor is an allosteric inhibitor.

12. The method of claim 11, wherein the allosteric inhibitor binds to ABL1 and/or ABL2 kinases at the myristate binding site.

13. The method of claim 11, wherein the allosteric inhibitor is GNF5 or ABL001.

14. A method of reducing bone metastasis associated with cancer in a subject suffering from cancer, comprising administering an ABL-specific inhibitor.

15. The method of claim 14, wherein the ABL-specific inhibitor is an allosteric inhibitor.

16. The method of claim 15, wherein the allosteric inhibitor binds to ABL1 and/or ABL2 kinases at the myristate binding site.

17. The method of claim 15, wherein the allosteric inhibitor is GNF5 or ABL001.

18. The method of claim 14, wherein the cancer is breast cancer.

19. The method of claim 18, wherein the breast cancer is HER2-positive or basal-like.

20. A method of reducing tumor-induced osteolysis associated with breast cancer in a subject suffering from breast cancer, comprising administering an ABL-specific inhibitor.

21. The method of claim 20, wherein the ABL-specific inhibitor is an allosteric inhibitor.

22. The method of claim 21, wherein the allosteric inhibitor binds to ABL1 and/or ABL2 kinases at the myristoyl binding site.

23. The method of claim 21, wherein the allosteric inhibitor is GNF5 or ABL001.

24. The method of claim 20, provided that no non-specific ABL inhibitor is administered.

25. The method of claim 24, wherein the non-specific ABL inhibitor is a ATP-competitive inhibitor.

26. The method of claim 24, wherein the ATP-competitive inhibitor is imatinib, dasatinib, or nilotinib.

27. A method of determining whether a subject suffering from breast cancer is likely to develop related bone metastasis, comprising:
determining expression levels of at least one gene selected from the group consisting of ABL2, TAZ, AXL, STAT5A, STAT5B, TNC, MMP1, CTGF, and IL6 in a biological sample,
wherein a level of expression of the at least one gene at least 3-fold greater than normal tissue indicates that the subject has an increased risk of developing breast cancer-related bone metastasis.

28. The method of claim 27, wherein expression levels of at least four genes selected from the group consisting of ABL2, TAZ, AXL, STAT5A, STAT5B, TNC, MMP1, CTGF, and IL6 are determined.

29. The method of claim 27, wherein the at least one gene is selected from the group consisting of ABL2, TAZ, AXL, STAT5A, and TNC.

30. The method of claim 27, wherein the at least one gene comprises ABL2, TAZ, and AXL.

31. The method of claim 27, wherein expression levels are determined by rtPCR.

32. A method of treating breast cancer in a subject suffering from breast cancer, comprising:
ordering a test which determines expression levels of at least one gene selected from the group consisting of ABL2, TAZ, AXL, STAT5A, STAT5B, TNC, MMP1, CTGF, and IL6 in a biological sample;
selecting subjects having a level of expression of the at least one gene at least 3-fold greater than normal tissue; and,
administering an ABL-specific inhibitor to the subjects.

33. The method of claim 32, wherein expression levels of at least four genes selected from the group consisting of ABL2, TAZ, AXL, STAT5A, STAT5B, TNC, MMP1, CTGF, and IL6 are determined.

34. The method of claim 32, wherein the at least one gene is selected from the group consisting of ABL2, TAZ, AXL, STAT5A, and TNC.

35. The method of claim 32, wherein the at least one gene comprises ABL2, TAZ, and AXL.

36. The method of claim 32, wherein the ABL-specific inhibitor is an allosteric inhibitor.

37. The method of claim 36, wherein the allosteric inhibitor binds to ABL1 and/or ABL2 kinases at the myristoyl binding site.

38. The method of claim 36, wherein the allosteric inhibitor is GNF5 or ABL001.

39. The method of claim 36, provided that no non-specific ABL inhibitor is administered.

40. The method of claim 39, wherein the non-specific ABL inhibitor is a ATP-competitive inhibitor.

41. The method of claim 40, wherein the ATP-competitive inhibitor is imatinib, dasatinib, or nilotinib.

42. A method of reducing bone metastasis associated with cancer in a subject suffering from cancer, comprising:
ordering a test which determines expression levels of at least one gene selected from the group consisting of ABL2, TAZ, AXL, STAT5A, STAT5B, TNC, MMP1, CTGF, and IL6 in a biological sample;
selecting subjects having a level of expression of the at least one gene at least 3-fold greater than normal tissue; and,
administering an ABL-specific inhibitor to the subjects.

43. The method of claim 42, wherein expression levels of at least four genes selected from the group consisting of ABL2, TAZ, AXL, STAT5A, STAT5B, TNC, MMP1, CTGF, and IL6 are determined.

44. The method of claim 42, wherein the at least one gene is selected from the group consisting of ABL2, TAZ, AXL, STAT5A, and TNC.

45. The method of claim 42, wherein the at least one gene comprises ABL2, TAZ, and AXL.

46. The method of claim 42, wherein the ABL-specific inhibitor is an allosteric inhibitor.

47. The method of claim 46, wherein the allosteric inhibitor binds to ABL1 and/or ABL2 kinases at the myristoyl binding site.

48. The method of claim 46, wherein the allosteric inhibitor is GNF5 or ABL001.

49. The method of claim 42, wherein the cancer is breast cancer.

50. The method of claim 42, wherein the breast cancer is HER2-positive or basal-like.

51. The method of claim 1, wherein the cancer is breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma or peripheral neuroepithelioma.

52. The method of claim 1, wherein the cancer is breast cancer, lung cancer, or colorectal cancer.

\* \* \* \* \*

UNITED STATES PATENT AND TRADEMARK OFFICE
CERTIFICATE OF CORRECTION

PATENT NO. : 9,931,342 B2
APPLICATION NO. : 15/422725
DATED : April 3, 2018
INVENTOR(S) : Ann Marie Pendergast Page 1 of 1

It is certified that error appears in the above-identified patent and that said Letters Patent is hereby corrected as shown below:

In the Specification

At Column 1, Lines 14-17, the text "This invention was made with Government Support under Federal Grant Nos. RO1 CA70940 and RO1 CA155160 awarded by the NIH. The Federal Government has certain rights in this invention." should be changed to --This invention was made with Government Support under Federal Grant Nos. TR001117, CA195549, RO1 CA70940 and RO1 CA155160 awarded by the NIH. The Federal Government has certain rights in this invention.--

Signed and Sealed this
Eighteenth Day of August, 2020

Andrei Iancu
*Director of the United States Patent and Trademark Office*